United States Patent
Bonnin

(10) Patent No.: US 8,378,072 B2
(45) Date of Patent: Feb. 19, 2013

(54) METHODS FOR DESIGNING AND SYNTHESIZING DIRECTED SEQUENCE POLYMER COMPOSITIONS VIA THE DIRECTED EXPANSION OF EPITOPE PERMEABILITY

(75) Inventor: Dustan Bonnin, Belmont, MA (US)

(73) Assignee: Declion Pharmaceuticals, Inc., Boxford, MA (US)

(

OTHER PUBLICATIONS

Iwai, L., et al. "T-cell molecular mimicry in Chagas disease: identification and partial structural analysis of multiple cross-reactive epitopes between *Trypanosoma cruzi* B13 and cardiac myosin heavy chain", Journal of Autoimmunity 24, 111-117, (2005).

Kosmopoulou, A., "T-cell Epitopes of the La/SSB Autoantigen: Prediction Based on the Homology Modeling of HLA-DQ2/DQ7 with the Insulin-B Peptide/HLA-DQ8 Complex", Journal of Computational Chemistry, vol. 27, No. 9, pp. 1033-1044, (2006).

Lin, M., et al., "Development and Characterization of Desmoglein-3 Specific T Cells from Patients and Pemphigus Vulgaris", J. Clin. Invest., vol. 99, No. 1, 31-40 (1997).

Loiseau, P., et al., "HLA class II polymorphism contributes to specify desmoglein derived peptides in *Pemphigus vulgaris* and *Pemphigus floiaceus*", Journal of Autoimmunity, 15, 67-73 (2000).

Lin, Q., et al., "Genetic dissection of the effects of stimulatory and inhibitory IgG Fc receptors on murine lupus", The Journal of Immunology, 177: 1646-1655 (2006).

Lu, Y., et al., "Identification of Kinectin as a Novel Behcet's Disease Autoantigen", Arthritis Res. Ther. 2005; 7(5):R1133-R1139, (2005).

Maynard, J., et al., "Structure of an Autoimmune T Cell Receptor Complexed with Class II Peptide-MHC: Insights into MHC Bias and Antigen Specificity", Immunity, vol. 22, 81-92 (2005).

Meinl, E., et al., "Myelin Basic Protein-specific T Lymphocyte Repertoire in Multiple Sclerosis", J. Clin. Invest., vol. 92, 2633-2643 (1993).

Minota, S., et al., "Autoantibodies to the constitutive 73-kD member of the hsp70 family of heat shock proteins in systemic lupus erythematosus", J. Exp. Med., vol. 168, 1475-1480, 1988.

Müller, R., et al., "IgG reactivity against non-conformational $NH_2$-terminal epitopes of the desmoglein 3 ectodomain relates to clinical activity and phenotype of *Pemphigus vularis*", Experimental Dermatology, 15: pp. 606-614, (2006).

O'Sullivan, D., et al., "On the interaction of promiscuous antigenic peptides with different dr alleles", The Journal of Immunology, vol. 147, No. 8, 2663-2669, (1991).

Pal, R., et al., "Evidence for multiple shared antigenic determinants within Ro60 and other Lupus-related ribonucleoprotein autoantigens in human autoimmune responses", The Journal of Immunology, 175: 7669-7677 (2005).

Papassavas, A.C., "HLA peptide-mediated strategies for modulation of cellular and humoral immune responses in transplantation", Current Pharmacogenomics, vol. 1, No. 1, 17-36 (2003).

Pedotti, R., et al., "Severe anaphylactic reactions to glutamic acid decarboxylase (GAD) self peptides in NOD mice that spontaneously develop autoimmune type 1 diabetes mellitus", BMC Immunology, 4:2 (2003).

Pinchuk, P., et al., "Antigenicity of polypeptides (poly alpha amino acids )", Microbiology Department, New Jersey College of Medicine and Dentistry, 673-679 (1965).

Pinilla, C., et al., "Advances in the use of synthetic combinatorial chemistry: Mixture-based libraries", Nature Medicine, vol. 9, No. 1, pp. 118-126, (2003).

Quintana, F., et al., "DNA fragments of the human 60-kDa heat shock protein (HSP60) vaccinate against adjuvant arthritis: identification of a regulatory HSP60 peptide", The Journal of Immunology, 171: 3533-3541 (2003).

Raz, R., et al., "B-cell function in new-onset type diabetes and immunomodulation with heat-shock protein peptide (DiaPep27): a randomised, double-blind, phase II trial", The Lancet, vol. 358, 1749-1753 (2001).

Rosloniec, E., et al., "HLA-DR1 (DRB1*0101) and DR4 (DRB1*0401) Use the Same Anchor Residues for Binding an Immunodominant Peptide Derived from Human Type II Collagen", The Journal of Immunology, 168:253-259, (2002).

Sakurai, Y. et al., "Analog Peptides of type II collagen can suppress arthritis in HLA-DR4 (DRB1*0401) transgenic mice", Arthritis Research & Therapy, 8:R150, (2006).

Schwarz, M., et al., "Antibodies to heat shock proteins in schizophrenic patients: Implications for the mechanism of the disease", Am J Psychiatry 156:7, 1103-1104 (1999).

Sekiguchi, M., et al., "Dominant Autoimmune Epitopes Recognized by Pemphigus Antibodies Map to the N-Terminal.Adhesive Region of Desmogleins", The Journal of Immunology, 167:5439-5448 (2001).

Ulmansky, R., et al., "Resistance to adjuvant arthritis is due to protective antibodies against heat shock protein surface epitopes and the induction of IL-10 secretion", The Journal of Immunology, 168: 6463-6469 (2002).

Van Roon, J., et al., "Stimulation of suppressive T cell responses by human but not bacterial 60-kD heat-shock protein in synovial fluid of patients with rheumatoid arthritis", J. Clin. Invest., vol. 100, No. 2, 459-463 (1997).

Veldman, C., et al., "Detection of Low Avidity Desmoglein 3-reactive T cells in *Pemphigus vulgaris* using HLA-DR-beta*0402 tetramers", Clinical Immunoloyg, 1-8 (2006).

Veldman, C., et al., "T Cell Recognition of Desmoglein 3 peptides in Patients with *Pemphigus vulgaris* and Healthy Individuals", The Journal of Immunology, 172: 3883-3892 (2004).

Wilson, D., "GAD-about BDC2.5: Peptides that stimulate BDC2.5 T cells and inhibit IDDM", Journal of Autoimmunity 20, 199-201 (2003).

Wilson, D. et al, "Specificity and degeneracy of T cells", Molecular Immunology 40:1047-1055, (2004).

Wucherpfennig, K., et al., "Structural basis for major histocompatibility complex (MHC)-linked susceptibility to autoimmunity: Charged residues of a single MHC binding pocket confer selective presentation of self-peptides in *Pemphigus vulgaris*", Proc. Natl. Acad. Sci. USA, vol. 92, 11935-11939 (1995).

Wucherpfennig, K., et al., "Structural requirements for binding of an immunodominant myelin basic protein peptide to DR2 isotypes and for its recognition by human T cell clones" J. Exp. Med., vol. 179, 279-290 (1994).

Yurasov, S., et al., "Persistent expression of autoantibodies in SLE patients in remission", The Journal of Experimental Medicine, vol. 203, No. 10, 2255-2261 (2006).

Alexander, J. et al., "Linear PADRE T Helper Epitope and Carbohydrate B Cell Epitope Conjugates Induce Specific High Titer IgG Antibody Responses", The Journal of Immunology, 200, 164: 1625-1633.

Anderson, "Overcoming original (antigenic) sin" Clinical Immunology, Academic Press, US, vol. 101, No. 2, pp. 152-157 (2001).

Bianchi, E., et al., "Universal Influenza B Vaccine Based on the Maturational Cleavage Site of the Hemagglutinin Precursor", Journal of Virology, vol. 79, No. 12, pp. 7380-7388, Jun. 2005.

Carlos, M., et al., "Immunogenicity of a Vaccine Preparation Representing the Variable Regions of the HIV Type 1 Envelope Glycoprotein", Aids Research and Human Retroviruses, vol. 16, No. 2, pp. 153-161, 2000.

Hoogenboom, H., "Selecting and screening recombinant antibody libraries", Nature Biotechnology, vol. 23, No. 9 1105-1116 2005.

Hust, M., et al., "Mating antibody phage display with proteomics", TRENDS in Biotechnology, vol. 22 No. 1, 8-14 2004.

Kim, et al., "Persistence of Immune Responses to Altered and Native Myelin Antigens in Patients with Multiple Sclerosis Treated with Altered Peptide Ligand", Clinical Immunology, 104:2, 105-114 (2002).

Kirsch, M., et al., "Parameters affecting the display of antibodies on phage", Journal of Immunological Methods, 301,173-185, 2005.

Knappik, A., et al., "Fully Synthetic Human Combinatorial Antibody Libraries (HuCAL) Based on Modular Consensus Frameworks and CDRs Randomized with Trinucleotides", J. Mol. Biol. 296 57-86, 2000.

Konthur, Z., et al., "Perspectives for systematic in vitro antibody generation", Gene, 364, 19-29,2005.

Laurie et al., "CD4+ T cells from Copolymer-1 immunized mice protect dopaminergic neurons in the 1-methyl-4-phenyl-1,2,3,6-tetrahydropyridine model of Parkinson's disease", Journal of Neuroimmunology, 183:60-8 (2007).

Lustgarten et al: "Identification of cross-reactive pepides using combinatioral libraries circumvents tolerance against Her-21neu-immunodominant epitope", Journal of Immunology, vol. 176, No. 3, 1796-1805 (2006).

Meyer, D., et al., "Hypervariable Epitope Constructs Representing Variability in Envelope Glycoprotein of SIV Induce a Broad Humoral Immune Response in Rabbits and Rhesus Macaques", Aids Research and Human Retroviruses, vol. 14, No. 9, pp. 751-760, 1998.

Meyer, D., et al., "Induction of Cytotoxic and Helper T Cell Responses by Modified Simian Immunodeficiency Virus Hypervariable Epitope Constructs", Viral Immunology, vol. 12, No. 2, pp. 117-129, 1999.

Morrison K L et al.: "Combinatorial alanine-scanning" Current Opinion in Chemical Biology, Current Biology Ltd, London, GB, vol. 5, No. 3, Jun. 1, 2001, pp. 302-307.

Olszewska, W., et al., "Nasal delivery of epitope based vaccines", Advanced Drug Delivery Reviews, 51:161-171 (2001).

Osbourn, J., et al., "Current methods for the generation of human antibodies for the treatment of autoimmune diseases", DDT, vol. 8, No. 18,845-851 2003.

Pantophlet, R., et al., "Improved design of an antigen with enhanced specificity for the broadly HIV-neutralizing antibody b12", Protein Engineering, Design & Selection, vol. 17, No. 10, pp. 749-758, 2004.

Pons J et al., "Energetic analysis of an antigen/antibody interface: alanine scanning mutagenesis and double mutant cycles on the HyHEL-10/lysozyme interaction." Protein Science o A Publication of the Protein Society May 1999, vol. 8, No. 5, May 1999, pp. 958-968.

Tam, J. et al., "Incorporation of T and B Epitopes of the Circumsporozoite Protein in a Chemically Defined Synthetic Vaccine Against Malaria", J. Exp. Med., 171:299-306 (1990).

Tsai, S.-J., "Glatiramer acetate could be a potential therapeutic agent for Parkinson's disease through its neuroprotectiev and anti-inflammatory effects", Medical Hypotheses, 69:1219-21 (2007).

Estaquier, J., et al., "Combinatorial Peptide Library as an Immunogen," Methods in Molecular Biology, 87:281-296 (1998).

Estaquier, Jerome, et al., "A Combinatorial Peptide Library Around Variation of the Human Immunodeficiency Virus (HIV-1) V3 Domain Leads to Distinct T Helper Cell Responses," Journal of Peptide Science, 2:165-175 (1996).

Gras-Masse, H., et al., "Confronting the degeneracy of convergent combinatorial immunogens, or 'mixotopes', with the specificity of recognition of the target sequences," Vaccine, 15(14):1568-1578 (1997).

Gras-Masse, Helene, et al., "Convergent peptide libraries, or mixotopes, to elicit or to identify specific immune responses," Immunology, 11:223-228 (1999).

Tranchand-Bunel D, et al., "Evaluation of an Epstein-Barr Virus (EBV) Immunoglobulin M Enzyme-Linked Immunosorbent Assay Using a Synthetic Convergent Peptide Library, or Mixotope, for Diagnosis of Primary EBV Infection," J Clin Microbiol., 37(7):2366-2368 (Jul. 1999).

Macklin, Kevin D., et al "Binding of Single Substituted Promiscuous and Designer Peptides to Purified DRB1*0101," Biochemical and Biophysical Research Communications vol. 242, No. 2, 1998, Received Aug. 21, 1997, pp. 322-326.

Jardetzky, T.S., et al "Peptide binding to HLA-DR1: a peptide with most residues substituted to alanine retains MJC binding," The EMBO Journal, vol. 9, No. 6, pp. 1797-1803 (1990).

* cited by examiner

Directed Sequence Polymer Creation

Steps for Creation of Directed Sequence Polymer

Figure 4

Preferred Defined Substitutive Rules for Directed Expansion of Epitope Permeability

| Amino Acid groupings used for exchanging amino acids during the creation of rules for the solid phase synthesis of DSP. Amino Acids grouped together are interchangeable. | | | | |
|---|---|---|---|---|
| | a | b | c | d |
| I | | R,H | | K |
| II | | W | | |
| III | | F,Y | | |
| IV | | | V,I,L,M | |
| V | | | C | |
| VI | T,S,G,P | | | |
| VII | | | | E,D,Q,N |
| Alanine | Alanine can be substituted for any amino acid | | | |

Figure 5

Generic Rule Structure and Ranges of Substitutions of DSP Synthesis

| | Sequence of amino acids to be synthesized (Amino Acid Sequence Synthesis Block $y_N$) | | | | | | Input Ratio |
|---|---|---|---|---|---|---|---|
| Base (a) | $x_1$ | $x_2$ | $x_3$ | $x_4$ | $x_5$ | $x_N$ | a = 0.0 - 80 |
| 1° Change (b)_ | $1°x_1$ | $1°x_2$ | $1°x_3$ | $1°x_4$ | $1°x_5$ | $1°x_N$ | b = 0.0 - 80 |
| 2° Change (c) | $2°x_1$ | $2°x_2$ | $2°x_3$ | $2°x_4$ | $2°x_5$ | $2°x_N$ | c = 0.0 - 80 |
| 3° Change (d) | $3°x_1$ | $3°x_2$ | $3°x_3$ | $3°x_4$ | $3°x_5$ | $3°x_N$ | d = 0.0 - 80 |
| Alanine (e) | Ala | Ala | Ala | Ala | Ala | Ala | e = 20 - 100 |

Full Length Order of DSP

| | N-terminal Modifier | Amino Acid Sequence Synthesis Block | | | | | | C-terminal Modifier |
|---|---|---|---|---|---|---|---|---|
| DSP | MN | $y_1$ | $y_2$ | $y_3$ | $y_4$ | $y_5$ | $y_n$ | MC |

Figure 6

Example of mock-source peptide DSP Synthesis Rules

| Rules of Defined Amino Acid Incorporation | | | | | | | | | | | |
|---|---|---|---|---|---|---|---|---|---|---|---|
| Input Ratios | y1 Amino Acid (% of total at position) | | | | | Input Ratios | y2 Amino Acid (% of total at position) | | | | |
| a(35) | T(35%) | H(45%) | M(40%) | C(50%) | E(35%) | a(4) | P(4%) | W(34%) | K(34%) | N(24%) | A(34%) |
| b(5) | S(5%) | R(5%) | V(5%) | | D(5%) | b(10) | T(10%) | | | Q(10%) | |
| c(5) | G(5%) | | I(5%) | | Q(5%) | c(10) | S(10%) | | | | |
| d(5) | P(5%) | | | | N(5%) | d(10) | G(10%) | | | | |
| e(50) | A(50%) | A(50%) | A(50%) | A(50%) | A(50%) | e(66) | A(66%) | A(66%) | A(66%) | A(66%) | A(66%) |

| Rules of Synthesis Block Combination and Modification | | | | | | | | | |
|---|---|---|---|---|---|---|---|---|---|
| N- Terminal Modification | Body of a Directed Epitope Peptide Mixture or Directed Sequence Polymer (DSP) | | | | | | | | C-Terminal Modification |
| RGDS | y1 | y1 | y2 | y2 | y1 | y1 | y2 | y2 | AKAVAAWTLK AAA |

Figure 7A

Example of MBP(83-99) source peptide DSP Synthesis Rules

| Input Ratios | | | Rules of Defined Amino Acid Incorporation — y1, y2, y3 Peptide Sequence — Amino Acid (% of total at position) | | | | | | | | | | | | | | | | |
|---|---|---|---|---|---|---|---|---|---|---|---|---|---|---|---|---|---|---|---|
| y1 | y2 | y3 | | | | | | | | | | | | | | | | | |
| a(19) | a(12) | a(1) | E | N | P | V | V | H | E | F | K | N | I | V | T | P | R | T | P |
| b(1) | b(9) | b(13) | D | E | T | I | I | R | D | Y |  | E | V | I | S | T | H | S | T |
|  | c(9) | c(13) | Q | D | S | L | L | Q |  |  |  | D | L | M | G | S |  | G | S |
|  |  | d(13) | N |  |  | M | M |  |  |  |  | Q | M | P |  |  |  | P | G |
| e(80) | e(70) | e(60) | A | A | A | A | A | A | A | A | A | A | A | A | A | A | A | A | A |

Figure 7B

Example of MBP(83-99) source peptide DSP Synthesis Rules

| Full Length Order of DSP | | |
|---|---|---|
| N-terminal Modifier | Amino Acid Sequence Synthesis Block | C-terminal Modifier |
| DSP | $y_1, y_1$ | $y_2, y_2$ |

| Full Length Order of DSP | | |
|---|---|---|
| N-terminal Modifier | Amino Acid Sequence Synthesis Block | C-terminal Modifier |
| DSP | $y_1, y_1$ $\mid$ $y_2$ | $y_3, y_3$ |

| Full Length Order of DSP | | |
|---|---|---|
| N-terminal Modifier | Amino Acid Sequence Synthesis Block | C-terminal Modifier |
| DSP | $y_1, y_1, y_1$ | |

| Full Length Order of DSP | | |
|---|---|---|
| N-terminal Modifier | Amino Acid Sequence Synthesis Block | C-terminal Modifier |
| DSP | $y_2$ $\mid$ $y_3, y_3$ | |

Figure 8A

Example of Multi-epitope HLA-derived source peptide DSP Synthesis Rules

| | Rules of Defined Amino Acid Incorporation | | | | | | | | | | | | | |
|---|---|---|---|---|---|---|---|---|---|---|---|---|---|---|
| | y1, y2, y3 Peptide Sequence Amino Acid (% of total at position) | | | | | | | | | | | | | |
| Input Ratio y1 | | | | | | Input Ratio y2 | | | | | | Input Ratio y3 | | | | |
| a(17) | K | D | I | L | E | a(94.5) | D | E | R | A | A | a(17) | V | D | T | Y | C |
| b(1) | E | V | V | V | D | b(0.5) | E | D | H | A | A | b(1) | I | E | S | F | |
| c(1) | Q | L | I | Q | | c(0.5) | Q | Q | A | A | A | c(1) | L | Q | G | | |
| d(1) | N | M | M | N | | d(0.5) | N | N | A | A | A | d(1) | M | N | P | | |
| e(80) | A | A | A | A | A | e(5) | A | A | A | A | A | e(80) | A | A | A | A | A |

Figure 8B

Example of Multi-epitope HLA-derived source peptide DSP Synthesis Rules

Rules of Defined Amino Acid Incorporation y4, y5 Peptide Sequence

Amino Acid (% of total at position)

| Input Ratio y4 | | | | | | Input Ratio y5 | | | | | | | | | |
|---|---|---|---|---|---|---|---|---|---|---|---|---|---|---|---|
| a(94.5) | Q | K | R | A | A | a(17) | Y | D | Y | G | H | A | A | F | E |
| b(0.5) | E |   | H | A | A | b(1)  | F | E | F | T | R | A | A | Y | D |
| c(0.5) | D |   |   | A | A | c(1)  |   | Q |   | S |   | A | A |   | Q |
| d(0.5) | N |   |   | A | A | d(1)  |   | N |   | P | A | A | A |   | N |
| e(5)   | A | A | A | A | A | e(80) | A |   | A | A | A | A | A | A | A |

Figure 8C

Example of Multi-epitope HLA-derived source peptide DSP Synthesis Rules

| Full Length Order of DSP | | |
|---|---|---|
| N-terminal Modifier | Amino Acid Sequence Synthesis Block | C-terminal Modifier |
| DSP | $y_1\ y_2\ y_3$ | $y_1\ y_2\ y_3$ |

| Full Length Order of DSP | | |
|---|---|---|
| N-terminal Modifier | Amino Acid Sequence Synthesis Block | C-terminal Modifier |
| DSP | $y_1,y_2,y_3$ | $y_4,y_5$ |

| Full Length Order of DSP | | |
|---|---|---|
| N-terminal Modifier | Amino Acid Sequence Synthesis Block | C-terminal Modifier |
| DSP | $y_4,y_5$ | $y_4,y_5$ |

Figure 9A

Example: GAD65. Empirically derived rules of amino acid incorporation

Ligands for BDC2.5 T cells

| Peptide | Sequence (Percent of total appearances at position) | | | | | | | | | |
|---|---|---|---|---|---|---|---|---|---|---|
| P1040-79 | A | V | R | P | L | W | V | R | M | E |
| P1040-31 | Y | V | R | P | L | W | V | R | M | E |
| P1040-63 | R | T | R | P | L | W | V | R | M | E |
| P1040-51 | R | V | L | P | L | W | V | R | M | E |
| P1040-35 | Y | T | L | P | L | W | V | R | M | E |
| Ratio in pooled sequences | A(20), Y(40) R(40) | V(60) T(40) | R(60) L(40) | 100 | 100 | 100 | 100 | 100 | 100 | 100 |

Figure 9B

Example: GAD65. Empirically derived rules of amino acid incorporation

| Ligands for BDC2.5 T cells | | | | | | | | | | |
|---|---|---|---|---|---|---|---|---|---|---|
| | Amino Acid Synthesis Block y1 (% of total at position) | | | | | | | | | |
| Empirically derived Ratios | A(10)<br>Y(20)<br>R(20) | V(30)<br>T(20) | R(30)<br>L(20) | P(50) | L(50) | W(50) | V(50) | R(50) | M(50) | E(50) |
| Alanine | A(50) | A(50) | A(50) | A(50) | A(50) | A(50) | A(50) | A(50) | A(50) | A(50) |
| | | Rules of Synthesis Block Combination and Modification | | | | | | | | |
| N-Terminal Modificatoin | | DSP Synthesis Block | | | | | | | C-Terminal Modificaiton | |
| | | y1 | y1 | y1 | y1 | y1 | y1 | y1 | | |

METHODS FOR DESIGNING AND SYNTHESIZING DIRECTED SEQUENCE POLYMER COMPOSITIONS VIA THE DIRECTED EXPANSION OF EPITOPE PERMEABILITY

RELATED APPLICATIONS

This application claims the benefit of U.S. Provisional Application 60/792,085, filed Apr. 13, 2006.

FIELD OF INVENTION

This application provides methods of making improved compositions of immunomodulatory peptide mixtures and provides methods of modulating unwanted immune responses.

BACKGROUND OF THE INVENTION

Immunomodulation.

Many disease conditions are, at least in part, a result of an unwanted or excessive immune response within an organism. The rejection of a transplanted organ is axiomatic example of an unwanted immune response. The rejection of the graft is emblematic of a condition in which an organism's inability to control an immune response results in a pathology. In organ transplantation, the unwanted immune response that results in graft rejection is triggered by: (1) "direct recognition," where the T cells of the graft recipient recognize foreign major histocompatibility complex ("MHC") molecules on the graft tissue, already presenting some peptides, via their T-cell receptor ("TCR") directly, or "indirect recognition," where the recipient T cells recognize the antigenic determinants derived from the graft after the determinants are processed and presented by recipient MHC; (2) the generation of antibodies directed against the graft, more specifically, the human leukocyte antigens ("HLA") molecules present on the cells of the graft tissue, caused by the exposure of the recipient to the graft; and (3) binding of preformed anti-graft antibodies in the circulation of the recipient to the graft. Studies have shown that these immune responses are directed to three types of donor derived antigens: MHC (through direct or indirect recognition), minor histocompatibility antigens ("mH"), and organ derived antigens.

Successful transplantation depends on preventing the unwanted immune responses, inducing sustained chimerism. Sustained chimerism is a phenomenon in which the recipient develops tolerance for a foreign graft, enabling the grafted tissue to survive in the recipient without being subjected to immune responses. Under experimental conditions, sustained chimerism can be induced by peptides that are closely related to those that stimulate graft-rejecting immune responses, albeit for short periods of time. (B. Murphy et al., *J. Am. Soc. Nephrol.,* 2003, 14:1053-1065; C. LeGuern, *Trends Immunol.,* 2003, 24:633-638). The difficulty lies with the likelihood of the broadening of the offending epitopes via the process of epitope spreading (N. Suciu-Foca et al., *Immunol. Rev.,* 1998, 164:241).

Transplant physicians have long recognized the need both to inhibit the immune response generated by the presence of what the recipient's immune system views as foreign, without also compromising the patient's ability to fight opportunistic infection. Currently, transplantation patients are often treated with immunosuppressive therapies that depress the overall immune response and reactivity in a patient. Immunosuppressive therapies attempt to attenuate the reaction of the body to an already-triggered immune response, and are accompanied by numerous undesirable side effects. Because of the significant undesirable side effects, a single immunosuppressant cannot be used continuously to treat a transplant recipient, and a course of treatment comprises using one immunosuppressant having one set of side effect, changing to second immunosuppressant with a different set of side effect, and to third, and so on, to limit the exposure of the recipient to each immunosuppressant and its side effects. For example, steroids such as prednisone or methylprednisone are powerful immunosuppressants but can induce cataracts, hyperglycemia, hirstutism, bruising, acne, bone growth suppression, and ulcerative oesophagitis. Long term use of steroids has also been associated with bone loss. Cyclosporin A (CsA), a widely used immunosuppressant, is nephrotoxic, and often replaced with tacrolimus (TAC) after a period of treatment. For the treatment of non-acute rejection, azathioprine is used, the side effect of which include leucopenia, anemia, fever, chills, nausea and vomiting. Regardless of what immunosuppressant is used, one of the most substantial side effects related to longer term treatment with immunosuppressives in addition to the general compromise of the immune system leaving the patient vulnerable to any type of infections, is the generation of transplant related malignancies such as Kaposi's sarcoma. There is a strong desire on the part of physician and patient to decrease or cease the use of these current front line therapies. (Pharmacotherapy: A pathophysiologic Approach, Fifth Edition. 2002, McGraw Hill.) It would be difficult to state that they have met the clinical goal of sustained chimerism without ongoing immunosuppressive therapy.

Immunomodulation, in contrast to immunosuppression, targets the cause of unwanted immune responses. Immunomodulation can be attempted in an antigen/epitope non-specific fashion by targeting the body's mechanism for immunity, or in an antigen/epitope specific manner. As an example of antigen/epitope non-specific treatment, therapies directly targeted at controlling T lymphocytes or their functions have been developed using biotechnological tools. The therapeutic agents useful for such treatment include Muromonab-CD3 (OKT3), antilymphocyte globulin (ALG), antithymocyte globulin (ATG), or interleukin-2 receptor monoclonal antibody ("mAb") daclizumab or basiliximab. Other agents include soluble CTLA-4, an anti-CD154 mAb; anti-CD11a; a humanized mAb which inhibits VLA-4; anti-CD2, 3, or 4 antibodies; and anti-CD152 antibodies (J. B. Matthews et al., *Amer. J. Transplantation,* 2003, 3: 794-80). While all of these therapeutic agents may induce a state of non-responsiveness of the recipient's immune system to the transplanted tissue with a reduction in side effects, as compared to e.g. prednisone, the therapies still do not meet the clinical goal of sustained chimerism without ongoing immunosuppressive therapy, except for limited reports, such as immunosuppressive withdrawal after combination therapy of total lymphoid irradiation followed by ATG administration (S. Strober et al., *Transplantation,* 2004 Mar. 27; 77(6): 932-936). Further, these therapies also suffer from the unattractive side effects of compromised overall immune function.

In contrast to the antigen non-specific immunomodulatory approach, the immune system can also be retuned, or modulated in an antigen/epitope specific manner. Such a type of immunomodulation is the process of increasing or decreasing the immune system's ability to mount a response against a particular antigenic determinant through either the TCR's recognition of complexes formed by MHC and antigens, or through the B cell receptor's ("BCR") recognition of the epitope itself. Because of the specificity of the process toward a particular antigenic determinant and not toward the immune system as a whole, antigen specific immunomodulation has advantages such as fewer undesirable side effects compared to current treatment modalities such as immunosuppressive therapies, which affects the overall immune system.

Antigenic determinant-specific immunomodulatory treatments can help establish such sustained chimerism by inducing donor-specific tolerance in host T lymphocytes. Immunomodulation of the reaction toward any and all of these antigens help attenuate or alleviate graft rejection and establish sustained chimerism. Studies indicate that one mechanism of action of immunomodulation by certain immunomodulatory peptides may be through their binding to T cells that would otherwise bind to the donor-derived antigens and resulting in differential activation of T cell functions. This mechanism has been suggested to be centrally induced tolerance involving the thymus (G. Benichou et al. *Immunol. Today*, 1997, 18(2):67-72). The demonstration of achieving sustained chimerism without immunosuppressive treatment via induction of donor-specific tolerance in host T lymphocytes through immunomodulation was performed by a group of investigators who, using mice, induced tolerance to the subsequent graft by intrathymic injection of a series of determinants from 3M KCl-extracted donor MHC-derived peptides. Two doses of anti-T cell antibody were given first to eliminate circulating T cells. Then eight peptide sequences extracted from the donor MHC were delivered in combination. The treated mice tolerated subsequent transplants. As a control, the investigators performed thymectomy, which caused graft rejection. The study is an example of importance of centrally-induced tolerance (T. Hamashima et al., *Transplantation*, 1994 Jul. 15; 58(1):105-7). Thus, designing appropriate peptides similar to T cell-stimulating antigens that bind to the T cells is beneficial to achieving sustained chimerism.

However, the difficulty lies with the likelihood of the broadening of the offending epitopes via the process of epitope spreading. (N. Suciu-Foca et al., *Immunol. Rev.* 1998, 164:241). Thus, in transplantation, the axiomatic example where certain immune response is unwanted, it is clear that, in the absence of the ability to modulate the relevant antigenic determinants over time, the only alternatives are non-specific immunomodulatory, or immunosuppressive therapies.

Other examples of unwanted immune responses are autoimmune diseases. One important contextual difference between autoimmune diseases and transplantation rejection is that the offending antigenic determinant(s) is/are generally more restricted and definable. While the trigger of an autoimmune disease is undefined and may be dictated by pre-existing and/or environmental factors, the direct causes of the pathological condition have been identified in many autoimmune diseases. An autoimmune disease results from an inappropriate immune response directed against a self antigen (an autoantigen), which is a deviation from the normal state of self-tolerance. Self-tolerance arises when the generation of T cells and B cells capable of reacting against autoantigens has been prevented or altered centrally by events that occur either in their early development or after maturation in the periphery. The cell surface proteins that play a central role in regulation of immune responses through their ability to bind and present processed peptides to T cells via the T cell receptor (TCR) are class I and class II MHC (J. B. Rothbard et al., *Annu. Rev. Immunol.*, 1991, 9:527).

Thus, an attractive point of intervention for the amelioration of an autoimmune response is via the set of lymphocyte surface protein MHC molecules for example, HLA-DR, -DQ and -DP, themselves or in combination with the peptides they present. Different HLA alleles generate a diversity of responses via antigenic-determinant specificities by variable affinities for protein fragments found in the extra- and intracellular milieu because of differences in the amino acids which are directly involved in the binding of the peptides. There are large numbers of alternative or allelic forms within a mammalian population, but only a few of these allelic forms are associated with disease-related antigenic determinants. It is well understood to one with ordinary skill in the art the genomes of subjects affected with certain autoimmune diseases, for example MS and RA, are more likely to carry one or more such characteristic MHC class II alleles, to which that disease is linked. For example, HLA-DR2 (DRB1*1501) is associated with multiple sclerosis and HLA-DR1 (DRBI*0101) or HLA-DR4 (DRB1*0401) are associated with rheumatoid arthritis.

The disease-related antigenic determinants derive from proteins which have been described as being simply associated with an autoimmune response, or as being part of the pathogenesis of the disease process itself. There are highly conserved sequences within HLA that may play a role in either the generation or regulation of immunologic tolerance when processed into peptides and presented by intact HLA (reviewed in B. Murphy and A. M. Krensky, *J. Am. Soc. Nephroi.*, 1999, 10:1346-55). A. Snijders et al. discuss one particular sequence (KDILEDERAAVDTYC) (SEQ ID NO: 206) presented by HLA-DRB1 as being protective against rheumatoid arthritis, with the most relevant portion of the peptide being DERAA (SEQ ID NO: 207) (*J. Immunol.*, 2001, 166:4987-93), while others have promoted what is known as the 'shared epitope hypothesis' (P. K. Gregersen et al., *Arthritis Rheumatism* 1987 November; 30(11):1205-13) where those individuals that carry HLA-DRB1 alleles having the sequence QKRAA (SEQ ID NO: 208) are predisposed to rheumatoid arthritis. Other investigators have demonstrated that heat shock proteins (hsp) and the peptides derived from them can have immunomodulatory properties (S. M. Anderton et al., *J. Exp. Med.*, 1995, 181:943-952; J. A. van Roon et al., *J. Clin. Invest.*, 1997, 100:459-063). One peptide in particular, dubbed p277, derives from hsp60, VLGGGVALL-RVIPALDSLTPANED (SEQ ID NO: 147), has demonstrated apparent activity in the context of Type I diabetes (I. Raz et al., *Lancet*, 2001, 358:1749-52). Further sources of epitope sequence may be derived from a pathogen-derived mimic of a sequence within mammalian MHC proteins such as the DNAjP1 peptide, or related peptides (QKRAAY-DQYGHAAFE (SEQ ID NO: 209); *Proc. Nat. Acad. Sci. USA*, 101:4228-33; U.S. Pat. No. 6,989,146). Other proteins and the peptides that derive from them having disease association are: glutamate decarboxylase (GAD) with diabetes (M. A. Atkinson et al. *J. Clin. Invest.*, 1994, 94:2125-29; D. B. Wilson *J. Autoimmun.*, 2003, 20:199-201); myelin associated proteins such as myelin basic protein (MBP), myelin-associated glycoprotein (MAG), proteolipid protein (PLP), and myelin oligodendrite glycoprotein (MOG) with multiple sclerosis (reviewed in P. Fontoura et al., *Int. Rev. Immunol.*, 2005, 24:415-46); Ro60, SmD and other ribonucleoprotein antigens with lupus (R. Pal, et al., *J. Immunol.*, 2005, 175: 7669-77; Seshmukh et al., *J. Immunol.*, 2000, 164:6655-61; R. R. Singh, *Mol. Immunol.*, 2004, 40:1137-45); or the acetylcholine receptor (AChR) with myasthenia gravis (MG) (S. L. Kirshner, et al. *Scand. J. Immunol.*, 1996, 44:512-21); or desmoglein 3 (DsG3) with pemphigus vulgaris (PV) (Wucherpfennig et al., *Proc. Nat. Acad. Sci. USA*, 1995, 92:11935-9; Lin et al., *J. Clin. Invest.*, 1997, 99:31-40; Veldman et al., *J. Immunol.*, 2004 172:3883-92; Angelini et al., *J. Translational Med.*, 2006, 4:43; U.S. Pat. No. 5,874,531; U.S. Pat. No. 7,084,247).

Despite the attraction of using HLA alleles and their associated antigenic determinants that have been linked to many autoimmune diseases as a point of intervention, therapeutic agents based on this knowledge have not been developed fully. Instead, a number of immunomodulatory therapeutic agents that are not specific to any particular antigenic determinant have been developed and being used to treat autoimmune diseases, including general anti-inflammatory drugs such as cyclooxygenase-2 (COX-2) inhibitors that can prevent formation of low molecular weight inflammatory compounds; inhibitors of a protein mediator of inflammation such as tumor necrosis factor (TNF), such as an anti-TNF specific monoclonal antibody or antibody fragment, or a soluble form of the TNF receptor that sequester TNF; and agents that target a protein on the surface of a T cell and generally prevent interaction with an antigen presenting cell (APC), for example by inhibiting the CD4 receptor or the cell adhesion receptor ICAM-1. However, these types of antigenic-determinant non-specific immunomodulatory therapeutic agents have residual immunosuppressive-like side-effects which diminish their attractiveness as chronic first line therapies. Additionally, compositions having natural folded proteins (such as antibodies) as therapeutic agents can encounter problems in production, formulation, storage, and delivery. Several of these problems necessitate delivery to the patient in a hospital setting.

Strategy for Creating Synthetic Therapeutic Peptides

Drug discovery can be generalized into two major elements, lead generation and lead optimization. The development and exploitation of combinatorial chemistry (CC) has seen the divergence of the uses of rational design versus random generation on a very fundamental level. On one side we find the use of CC to assist a researcher in the rational design of molecules. An example of which can be seen in the discovery of structure/activity relationships (SAR) between two or more active molecules of therapeutic interest. On the other side we find researchers using CC to define for them the design of new molecules discovered based on a specific activity. An example of which would be the generation of random libraries used in lead generation, whereby the lead is singled out and further optimized.

The level of expertise in the state of the art of combinatorial chemistry as applied to the synthesis of peptide libraries has risen, producing highly reliable and pure mixtures of peptides of great diversity. The use of these diverse peptide libraries has focused on lead generation and optimization. This strategy entails screening the vast numbers of individual peptide sequences in the library against a target of interest with the intention of defining a single, or limited set of peptides which demonstrate a particular activity. That single peptide, or the limited set of peptides, then become candidates which are modified to increase activity against the target. This process is schematically represented in FIG. 1A.

The challenge for practitioners in this art has been to deconvolute, or accurately define the single or limited set of peptides that were responsible for the observed activity. The difficulties associated with deconvolution have spawned great efforts on the part of practitioners to create synthesis methods which inherently increase the resolution of individual peptides, as well as the identity of individual amino acids within peptides.

In order to efficiently identify the target peptide from myriad of candidates presented by a library created by combinatorial chemistry, a variety of synthesis methods and approaches have been developed. These synthesis methods aim to provide a large number of candidates, and yet when a positive result is obtained, to quickly determine the identity of the peptide without having to laboriously isolate the positive species from the rest. The effort put forth by practitioners in this art in this regard is an indication of the industry-wide vision of the method's ultimate utility, which is to allow the random complexity of these libraries perform the screening process for the desired activity.

Examples of the resulting evolution of subtypes of combinatorial methods include: multiple synthesis, iterative synthesis, positional scanning, and one-compound-one-bead post assay identification design.

Multiple synthesis" provides for any method whereby distinct compounds are synthesized simultaneously to create a library of isolated compounds. The identity of these compounds would be known from the rules of the synthesis. H. M. Greysen et al., *Proc. Nat. Acad. Sci. USA*, 1984, 81:3998, used the multiple synthesis method to identify peptides that bound to an antibody raised against VPI protein of foot-and-mouth disease virus. The investigators identified GDLQVL (SEQ ID NO: 210) as the epitope recognized by the antibody. In this case the authors synthesized 108 overlapping peptides representing the VPI sequence on pins in a 96-well microplate array.

"Iterative synthesis/screening" involves methods of peptide synthesis which allow for a determination of the identity of individual residues within peptide sequences. An example of iterative synthesis can be seen in R. A. Houghten et al., *Nature*, 1991, 354:84-86, also to determine antibody binding epitopes. These investigators identified the sequence YPYDVPDYASLRS (SEQ ID NO: 211) using an ELISA type assay format. The first library consisted of 324 pools of peptides with the first two residues fixed, which peptides can be shown as $O_1O_2XXXX$, wherein O1 and O2 are the fixed residues and X is randomly selected. The process identified DV as the fix residues. The next step was to do the same for position three, by synthesizing peptides that can be shown as DV $O_1XXX$, wherein O1 again is a fixed residue. When the process identified which residue at the third position would elicit the desired binding, that residue was adopted as the unchanging third residue, and the fourth position was explored in a similar manner. The process continued until the native sequence DVPDYA (SEQ ID NO: 212) was identified.

"Positional scanning" is a synthesis method producing complex mixtures of peptides that allows for the determination of the activity of each individual peptide. Based on the screening results, the derived peptide can then be separately synthesized for optimization. As seen in C. Pinilla et al., *Biochem J.*, 1994, 301:847-853, positional scanning libraries were used to identify decapeptides which bound the same YPYDVPDYASLRS-binding (SEQ ID NO: 211) antibody. In this case ten different libraries each containing 20 pools with a defined amino acid at each of the ten positions in the peptide. Fifteen peptides were identified.

Each of the above methods were also employed to identify enzyme substrates (J. H. Till et al., *J. Biol. Chem.*, 1994, 269:7423-7428, J. Wu et al, *Biochemistry*, 1994, 33:14825-14833, W. Tegge et al., *Biochemistry*, 1995, 34:10569-10577), or enzyme inhibitors (M. Bastos et al., *Proc. Nat. Acad. Sci. USA*, 1995, 92:6738-6742, Meldal et al., *Proc. Nat. Acad. Sci. USA*, 1994, 91:3314-3318), R. A. Owens et al., *Biomed Biophys. Res. Commun.*, 1994, 181:402-408, J. Eichler. et al., *Pept. Res.*, 1994, 7:300-7). These powerful tools allow investigators to rationally design combinatorial peptide libraries to identify a single species which has a desired activity.

As powerful and clear cut the identification of a specific peptide from a combinatorial library may be, it may only serve as a starting point and identification of a lead peptide that is not itself therapeutically useful. The identified epitope may be ignored by the immune system if it resembles a self protein or possibly exacerbate the very condition that the therapy aims to relieve. Such peptide is not directly therapeutically useful. However, one may create, based on such peptide, epitope reactive analogs that would act as modifiers of the unwanted immune response.

One such approach is creation of altered peptide ligands (APL). This approach is schematically represented in FIG. 1B. An APL is defined as an analog peptide which contains a small number of amino acid changes from the native immunogenic peptide ligand. Some of such APLs act as an antagonist to the T cell receptor, blocking the stimulating binding by the antigens causing the unwanted immune effect. Evabold et al., *Proc. Nat. Acad. Sci. USA*, 1994 Mar. 15; 91(6):2300-4. However, while recognition of the native response may induce an angonist like reaction, an APL might induce a partial agonist response, or induce a state of energy in the reactive T cell population. In discussing APL in the context of allograft rejection therapy, Fairchild et al., *Curr. Topics Peptide Protein Res.*, 2004, 6:237-44, note that an APL acting as an antagonist for one TCR, may become an agonist for another, complicating the rational design of an APL. Compounding the obstacle of the development of APL is the difficulty in translating a response developed in an animal system into human.

Despite these challenges, MPB83-99 (ENPVVHEFKNIVTPRTP) (SEQ ID NO: 213) was made into an APL and placed into limited human trials by replacing the bold and underlined amino acid residues "E", "N", "E" and "K," resulting in a single peptide sequence consisting of AKPVVHLF ANIVTPRTP (SEQ ID NO: 214), Kim et al. *Clinical Immunology*, 2002, 104:105-114. The authors describe the long term immune reactivity against the peptide, but the treatment has been deemed clinically ineffective by evaluation using MRI. Thus an APL, once identified, can be used as a therapeutic agent; however, its effectiveness may be limited in terms of clinical efficacy.

It has been observed for some time that in the course of development of multiple sclerosis, the reactive epitope does not stay constant. That is, the self recognition associated with the development of MS is a developmental process characterized by autoreactive diversity, plasticity, and instability, wherein the target epitope changes over time, typically from one epitope on a myelin proteolipid protein to one overlapping the amino acid residues but shifting by one or few amino acids to either side of the original epitope. The consequence of this phenomenon is that if an immunotherapeutic drug was targeted at the original epitope, over time, it becomes ineffective, not because of resistance to the mechanism of the drug, but simply because the target is no longer valid. *J. Clin. Invest.*, 1997, 99:1682-1690.

A method conceived to make an investigational concept like a mixture of peptides into a drug is peptide dendrimer structures. Peptide dendrimers solve certain manufacturing issue of soluble peptide mixtures, in part by the promise of delivering to a patient a consistent ratio and quantity of each of the peptides in the mixture. This approach is schematically represented in FIG. 1C.

Dendrimers are diverse. They can range in size from 2 kDa to greater than 100 kDa. The design of dendrimers intends to mimic two traits of naturally occurring biological structures: a globular structure and polyvalency. As described in two comprehensive reviews (P. Niederhafier et al., *J Peptide Sci.* 11:757-788; K. Sadler and J. P. Tam, *Rev. Mol. Biotechnol.*, 2002, 90:195-229), they are complex compounds that contain highly branched components organized in a radial or wedge-like fashion, and are intended to have an extensive three-dimensional structure. They have three distinct structural features: a central core surface functionalities and branching units that link the two. Peptide dendrimers are designed as vehicles for delivery of: RNA and DNA as gene expression therapeutics, biosensor systems as diagnostics, inhibitors of autoimmune diseases or cancer metastasis. The strategy behind each of these applications is to use the globular, polyvalent structure to amplify the ligand:substrate interaction (D. Zanini and R. Roy, *J. Org. Chem.*, 1998, 63:3468-3491; J. Haensler and F. C. Szoka, *Bioconjug Chem.*, 1993, 4:372-379).

Dendrimers have been made using amino, hydroxyl, carboxy, poly(propylenimine), silicone and polyamino amine cores (G. M. Dykes et al., *J. Chem. Technol. Biotechnol.*, 2001, 76:903-918, P. Sadler and J. Jezek, *Rev. Mol. Biotechnol.*, 2002, 80:195-229, and J. P. Tam, *Methods Org. Chemistry*, 2004, Vol E22d 129-168. Peptide dendrimers can be divided into three types: grafted peptide dendrimers, branching polyamino acids and multiple antigen peptides (MAPs).

The branching strategies in MAPs vary widely. The majority of first generation branches have used lysine. Second generation solid phase synthesis of MAPs has seen an interest in proline. The interest is said to come from both the properties of its secondary amine which decreases the reactivity during production, as well as its role in many cellular functions.

Simple MAPs have been synthesized using solid phase chemistry, with this type of synthesis strategy called divergent. Synthesis methods have been described which involves a two-step iterative reaction sequence producing concentric shells of dendritic beta-alanine units covalently linked in the second step to various functional groups (Kojima et al., *Bioconjugate Chem.*, 2000, 11:910-17). These types of MAPs, which are synthesized using the divergent strategy, by necessity have simple branching schemes with few distinct members, as the purification and characterization are untenable with more complex MAPs. The end-product needs to be purified away from deletion compounds having similar characteristics to the end-product. Purifications have been described using gel filtration chromatography, reverse phase high-performance liquid chromatography (HPLC), or electromigration methods.

For complex MAPs, for example, those having a multiplicity of branching moieties, convergent synthesis is the preferred synthesis strategy. Convergent synthesis can be performed using either fragment condensation or ligation of the pre-purified fragments. There are many types of ligations: natural (true peptide bond created), thiol, hydrazone, or other. MAPs prepared using convergent synthesis strategies are easier to purify, as the end-product will look distinctly different from the reaction byproducts. HPLC was first used to purify convergent MAPs (J. C. Spetzler et al., *Int. J. Pept. Protein Res.*, 1995, 45:78-85).

However, a high cost of manufacturing and the subsequent analytical development precludes this technology from being further currently developed commercially.

All of the above strategies, while recognizing the advantage of variations in the therapeutic peptide compositions, derive from the concept that there is one or more defined peptide sequence evoking a defined immunological response. These strategies have attempted to multiply and diversify modulatory peptides via the introduction of defined, single changes performed one at a time.

An entirely different approach which has evolved alongside the defined sequence peptide immunotherapy approach is the use of limited amino acid diversity, random epitope polymers. Random sequence polymers (RSP) can be described as a random order mixture of amino acid copolymers comprising two or more amino acid residues in various ratios, forming copolymers by random sequence bonding, preferably through peptide bonds, of these amino acid residues, which mixture is useful for invoking or attenuating certain immunological reactions when administered to a mammal. Because of the extensive diversity of the sequence mixture, a large number of therapeutically effective peptide sequences are likely included in the mixture. In addition, because of the additional peptides which may at any given time not be therapeutically effective, but may emerge as effective as the epitope shifting and spreading occurs, the therapeutic composition may remain effective over a time of dosing regimen. This approach is schematically represented in FIG. 1D.

Starting in 1959 (P. H. Maurer et al., *J. Immunol.*, 1959, 83:193-7) to 1988, (J. L. Grun, and P. H. Maurer, *Immunogenetics*, 1988, 28(1): 61-3) Maurer and colleagues investigated the immune responses to poly glutamic acid and other random sequence polymers such as those consisting of tyrosine, glutamate and alanine (YEA), phenylalanine, glutamate and alanine (FEA), and phenylalanine, glutamate and lysine (FEK). Teitelbaum et al., *Eur. J. Immunol.*, 1971, 1:242-8 was the initial report of work on random copolymer consisting of tyrosine, glutamate, alanine and lysine, that eventually culminated in an FDA approved therapy for multiple sclerosis using COP-1, described below. In 1978, Germain and Benacerraf, *J. Exp. Medicine* 148:1324-37, investigated suppressor T cell responses to YEA in what was to become Benacerrafs 1980 Nobel winning work on the role of MHC in the immune system and its relevance to alloreactivity (http://nobelprize.org/nobel_prizes/medicine/laureates/1980/ben-acerraf-lecture.html).

Copolymer-1 (also known as Copaxone, glatiramer acetate, COP-1, or YEAK (SEQ ID NO: 217) random copolymer), is used for the treatment of multiple sclerosis. Random copolymers are described in International PCT Publication Nos. WO 00/05250, WO 00/05249; WO 0/59143, WO 0027417, WO 96/32119, WO/2005/085323, in U.S. Patent Publication Nos. 2004/003888, 2002/005546, 2003/0004099, 2003/0064915 and 2002/0037848, in U.S. Pat. Nos. 6,514,938, 5,800,808 and 5,858,964.

SUMMARY OF THE INVENTION

The instant invention comprises a process for the solid phase synthesis of directed epitope peptide mixtures useful in the modulation of unwanted immune responses, such process defined by a set of rules regarding the identity and the frequency of occurrence of amino acids that substitute a base or native amino acid of a known epitope. A method of the instant invention uses a sequence of a known peptide epitope as a starting point. The amino acids that make up the epitope are sequentially modified via the introduction of different, related amino acids defined by a set of rules. The result is a mixture of related peptides useful in and of itself as a therapeutic, which is described herein as a composition comprising "directed-sequence polymers" or "DSP". Such composition is referred to as a "DSP composition." The method of synthesizing a DSP composition utilizes and maintains the natural order of amino acid residues of a defined peptide sequence of a specified length. Each amino acid position is subjected to change based on a defined set of rules. In a preferred embodiment the amino acids is substituted according to the methods seen in Table X of Kosiol et al., *J Theoretical Biol.*, 2004, 228:97-106). Alternatively, amino acids can be changed in accordance with the exemplary substitutions described in PCT/US2004/032598, page 10-11. For the solid phase synthesis procedure of the instant invention, the mixture of amino acids for a given position in the peptide is defined by a ratio one to another. Prior to starting the synthesis, such ratio is determined for each position along the peptide. The resulting directed order peptide mixture comprises a multiplicity of related peptide sequences.

The length of a DSP can be one of the original defined sequence peptide or 30 lengths of the original defined sequence peptide. The length of the combined sequence can be between 25 and 300 amino acids.

The percentage of alanine as compared to all of the other amino acids in the DSP combined will always be greater than 10%, and will not exceed 90%. Preferably, the alanine percentage is between 20% and 80%. More preferably the percentage of alanine is between 40% and 75%. The complexity of the mixture is greater than $5 \times 10^2$ different peptides. Preferably the complexity of the mixture is greater than $1 \times 10^{10}$ different peptides. More preferably the complexity of the mixture is greater than $1 \times 10^{15}$ different peptides.

In some embodiments, the base peptide sequence from which the DSP sequences are derived is selected from a group consisting of SEQ ID NO: 1 through 189 and 205 depicted in Table 1.

In other embodiments, such base peptide sequence is an epitope relevant to the pathology of an autoimmune disease selected from the group consisting of multiple sclerosis, systemic lupus erythematosus, type I diabetes mellitus, myasthenia gravis, rheumatoid arthritis, and pemphigus vulgaris. More particularly, the base peptide sequence is a partial sequence of a protein selected from the group consisting of: (a) osteopontin, an HLA protein, myelin oligodendrite glycoprotein, myelin basic protein (MBP), proteolipid protein, and myelin associated glycoproteins, S100Beta, heat shock protein alpha, beta crystallin, myelin-associated oligodendrocytic basic protein (MOBP), 2',3' cyclic nucleotide 3'-phosphodiesterase; (b) hsp60, hsp70, Ro60, La, SmD, and 70-kDa U1RNP; (c) glutamic acid decarboxylase (GAD65), insulinoma-antigen 2 (IA-2), insulin; (d) acetylcholine receptor (AChR) α-subunit and muscle-specific receptor tyrosine kinase (MuSK); (e) type II collagen; and (f) desmoglein 3 (Dsg3)

One aspect of the present invention is a pharmaceutical composition comprising a DSP composition, optionally as a pharmaceutically acceptable salt. In a preferred embodiment, such pharmaceutical composition comprising a DSP composition, when administered to a subject, causes a favorable modification of an unwanted immune response in the subject desirous of such an effect.

Another aspect of the present invention is a method of treating unwanted immune response by administering a DSP composition to a subject in need thereof. In preferred embodiments, the subject is in need of such administration because of acute inflammation, rheumatoid arthritis, transplant rejection, asthma, inflammatory bowel disease, uveitis, restenosis, multiple sclerosis, psoriasis, wound healing, lupus erythematosus, pemphigus vulgaris, and any other autoimmune or inflammatory disorder that can be recognized by one of ordinary skill in the art. In other embodiments, the subject is in need of such administration because of Host versus Graft Disease (HVGD) or Graft versus Host Disease (GVHD), in the case of organ transplantation.

BRIEF DESCRIPTION OF THE DRAWINGS

FIG. 4 shows the preferred defined substitutive rules for directed expansion of epitope permeability.

FIG. 5 shows a generic rule structure and ranges of substitutions of DSP synthesis.

FIG. 6 shows an example of the application of the DSP Synthesis Rules using a mock-source peptide. RGDS and AKAVAAWTLKAAA peptides disclosed as SEQ ID NO: 239 and 236, respectively.

FIG. 7A-B shows an example of the application of the DSP Synthesis Rules using myelin basic protein (a.a. residues 83-99) as a source peptide.

FIG. 8A-C shows examples of the application of the DSP Synthesis Rules using an HLA-derived peptide and an HLA mimic-derived peptide as source peptides.

FIGS. 9A-9B shows an example of the application of the DSP Synthesis Rules using a GAD65-derived epitope peptide as a source peptide and applying an emprirically determined substitution rule. FIG. 9A disclosed SEQ ID NOS 47, 240, 82, 83 and 91, respectively, in order of appearance.

DETAILED DESCRIPTION OF THE INVENTION

Figure 1:
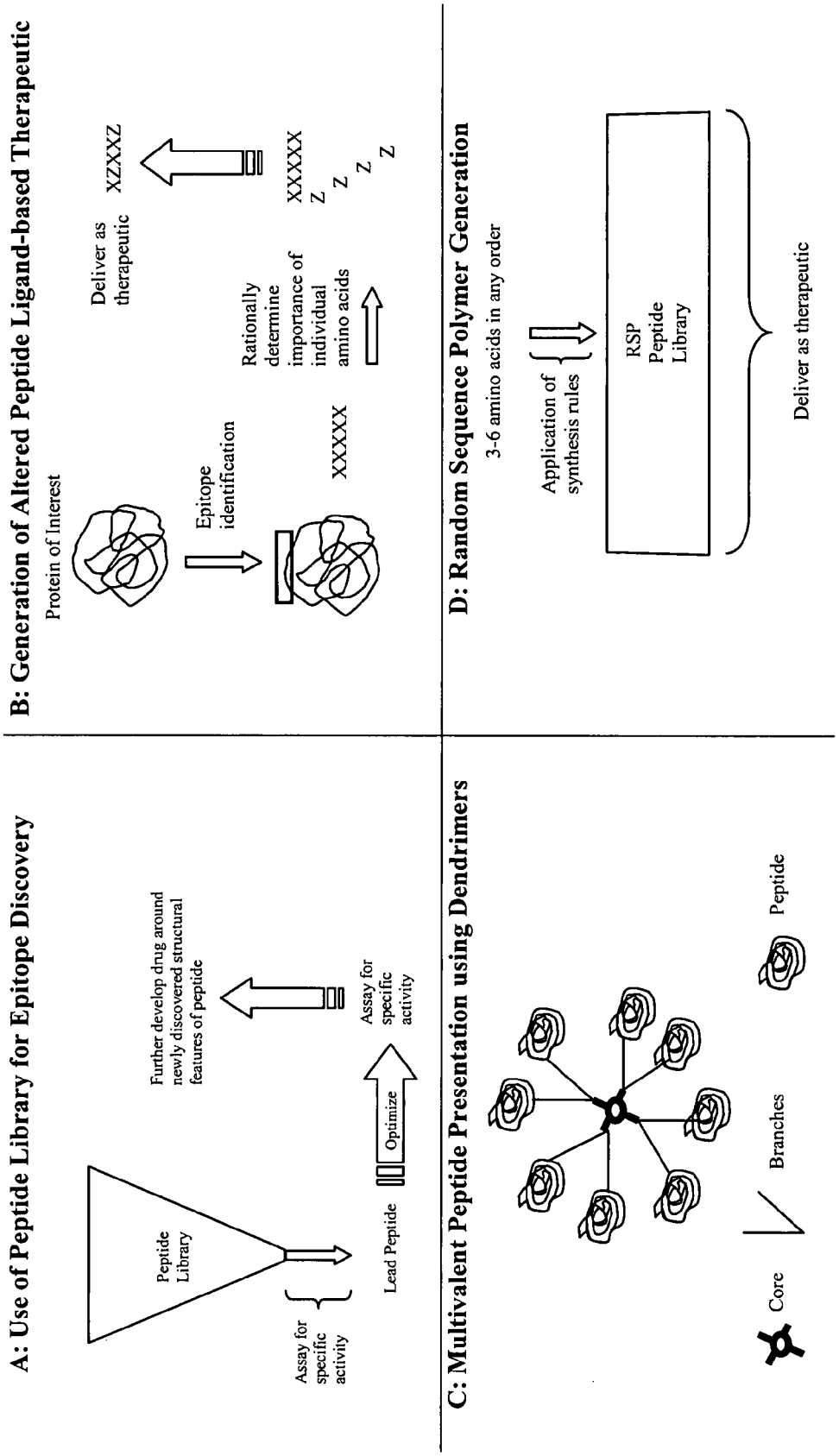
FIG. 1A-D is a schematic depicting methodologies for designing synthetic peptide-based therapeutics. Panel A: how a peptide library is used for epitope discovery; Panel B: conceptual steps for generating Altered Peptide Ligand-based therapeutic; Panel C: a schematic of a dendrimer for multivalent peptide presentation; Panel D: random sequence polymer generation.

It has previously been shown that mixtures of related peptides may be therapeutically more effective than a single peptide. Lustgarten et al., *J. Immunol.* 2006, 176: 1796-1805; Quandt et al., *Molec. Immunol.* 2003, 40: 1075-1087. The effectiveness of a peptide mixture as opposed to a single peptide is the likelihood of interaction with the broadening of the offending epitopes via the process of epitope spreading. (*Immunol. Rev.* 1998, 164:241) Therefore, to increase and maintain the effectiveness, these previous treatment modalities have been modified. For example, a therapeutic composition based on an APL may include multiple peptides created by the APL method in combination with the original peptide, or other APLs. Fairchild et al., *Curr. Topics Peptide & Protein Res.* 6, 2004. Each APL would have a defined sequence, but the therapeutic composition may be a mixture of APLs with more than one sequence. A reverse example involving conceptually similar altered peptide ligands involves an inventor's attempt to reduce the amount of variation created by pathogens to avoid immune recognition (viral alteration of immunogenic epitopes over time, eg the creation of altered peptide ligands), by using the very changes created by the pathogen in an epitope sequence to create a limited diversity pool of peptides potentially useful in vaccinations (U.S. Pat. No. 7,118,874).

There have also been approaches to improving RSP, most notably upon COP-1. One can be seen in the work originated by Strominger et al. (WO/2003/029276) and developed further by Rasmussen et al. (US 2006/0194725) using RSP consisting of the amino acids Y, F, A, and K. Other than the change in amino acid content, the differences between the composition reside in the length (YFAK (SEQ ID NO: 215) is shorter than COP-1), and alanine content (YFAK (SEQ ID NO: 215) is suggested to have between 60-80% alanine, compared to _% of COP-1), which show as differences in the animal model data (YFAK (SEQ ID NO: 215) has better efficacy in EAE, the animal model of multiple sclerosis). Regarding the alanine content, Maurer (Pinchuck and Maurer, *J. Exp Med* 122(4), 673-9, 1965) described how an EAK polymer with higher alanine content (10-60 mole percent) produced "better antigens", and Rasumussen et al. demonstrated that a YFAK (SEQ ID NO: 215) input ratio of 1:1:1:1 was not effective in eliciting a recall response as compared to a YFAK (SEQ ID NO: 215) preparation with an input ratio of 1:1:10:6.

Another attempt at improving upon COP-1 is described in WO/2005/032482 (the '482 publication). One interpretation of the '482 publication is that it is an attempt to make a more specific COP-1 by limiting the amount of diversity via the generation of 'therapeutic ordered peptides' for the treatment of multiple sclerosis. The '482 publication builds degenerate peptide sequences based not on actual peptide sequences, but on motifs. A preferred motif is [EYYK] (SEQ ID NO: 216), which is quite similar to the amino acid composition of COP-1 (YEAK) (SEQ ID NO: 217). The rationale for this motif teaches that the relative value placed on the inclusion of alanine as seen in the Maurer publication and Rasmussen et al. application discussed above is of a lesser importance The motifs are used as is, or can be altered by amino acid substitutions (defined on page 10-11 of the '482 publication). Much of the invention hinges on the presence of a D-amino acid at the amino terminal of the motif.

Yet another attempt at improving upon COP-1 is disclosed in WO/2005/074579 (the '579 publication). The application describes complex peptide mixtures containing A, E, K and Y of a length from 8-100 residues long. The disclosure contains preferred embodiments where the mixture also comprises AEKY (SEQ ID NO: 218), FLMY (SEQ ID NO: 219), IMQV (SEQ ID NO: 220), KRILV (SEQ ID NO: 221), FILMV (SEQ ID NO: 222), FWEF (SEQ ID NO: 223), EK, AEK, AKY, ANY, AINV (SEQ ID NO: 224), ASV, YEFW (SEQ ID NO: 225), Y, EFIVWY (SEQ ID NO: 226), EFKQ (SEQ ID NO: 227), AEKQ (SEQ ID NO: 228), AKQY (SEQ ID NO: 229), ANQY (SEQ ID NO: 230), AGNSY (SEQ ID NO: 231), AGINSV (SEQ ID NO: 232), AIQSV (SEQ ID NO: 233), IKRSVY (SEQ ID NO: 234), KHRV (SEQ ID NO: 235), HKR, PI, A, E, K, AE, AK, AY, EY, KY, AEY, EKY. The disclosure also contains diversity constraining mechanisms of defining amino acids at certain positions rather than being chosen by the random nature of the synthesis rules. The disclosure provides for a ratio of amino acids one to another for the AEKY (SEQ ID NO: 218) mixture as being similar to COP-1 at 1:1:6:3 YEAK (SEQ ID NO: 217).

The drawback of the these approaches is the undefined nature of what is effective in each motif, and quite possibly a large proportion of the peptides in the mixture may be inactive, lowering the concentration of the active components, or worse, adversely stimulating the immune system. Additionally, these compounds are difficult to manufacture and to obtain consistency from lot to lot.

Still another attempt at improving upon COP-1 can be seen in Strominger's efforts to design distinct, single 15mer peptide sequences who's amino acid composition resembles that of COP-1 and COP-1 related random sequence polymers. These single sequence fixed peptides were designed to increase an ability to compete for HLA-DR2 binding with the native myelin basic protein (MBP) peptide 85-99 (Stem et al., roc. *Nat. Acad. Sci. USA,* 102:1620-25). The drawback of this technology lies in the very nature of the attempt to determine discrete substitutes for the randomness that COP-1 encompasses.

Figure 2:
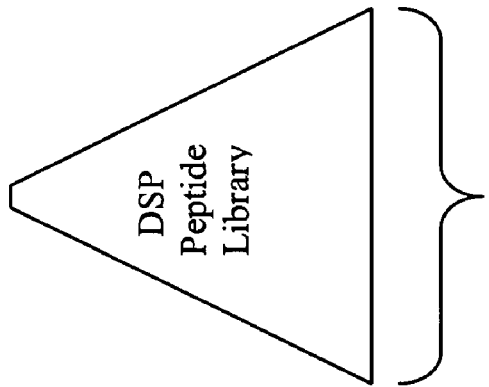
FIG. 2 is a schematic for conceptual steps for generating Directed Sequence Polymers.
Figure 3:
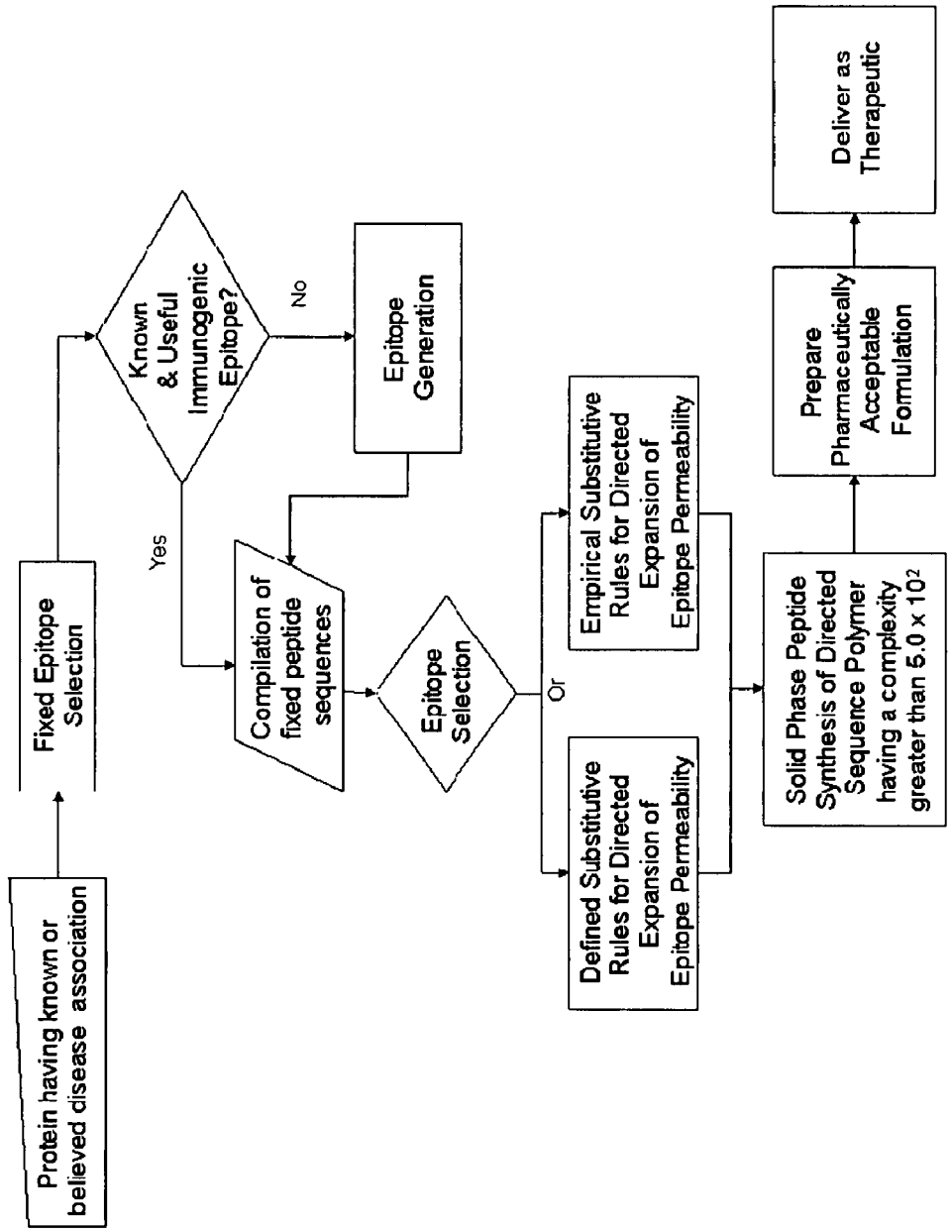
FIG. 3 shows the steps for preparing Directed Sequence Polymers.

The instant invention draws out the most useful properties of the previous treatment modalities yet removes the limitations of each. The instant invention utilizes: (1) the specific immunologic relevance of a defined epitope peptide, (2) the modulatory properties of an APL, (3) the multivalency of MAPs, (4) and the alanine content from RSP to generate a directed expansion via alteration and degeneration of epitope permeability that forms a complex yet directed peptide library useful for delivery as a therapeutic. The approach is schematically represented in FIG. 2.

The instant invention relates to a "Directed Sequence Polymer" (DSP). A DSP is a peptide having a sequence derived from a base peptide sequence, which may be but not limited to a native epitope associated with an unwanted immune response. A DSP has one or more amino acid residue that differs from that of the base peptide sequence, the substitution of which is determined by a defined rule. A DSP composition comprising multiple DSPs is synthesized by applying a set of synthesis rules that define the amino acid variations and the ratio of occurrence of introduction of such amino acid residues at any given position of the sequence to the base peptide sequence. Thus, a DSP is not synthesized as a single peptide, but is always synthesized as part of a composition comprising multiple related DSPs, the overall mixture of which is reproducible and consistent with the rules of synthesis that were applied. The schematic for the steps for creating a DSP composition, starting from the choice of a base peptide, is shown in FIG. 3.

I. Base Peptide Sequences

To create a meaningful DSP composition, one first needs to define the base peptide sequence to derive the DSPs from. The base peptide sequences can be derived in many ways. A peptide sequence useful for this purpose is a peptide sequence related to immune response in a mammal. These peptide sequences are, for example, partial sequences of certain heat shock proteins as an epitope, HLA derived peptide ligand sequences, organ-derived peptide sequences, and empirically derived peptide sequences, such as through screening of library created by a combinatory chemistry.

Heat Shock Protein-Derived Base Peptide Sequences.

A source of epitope sequence may be derived from heat shock proteins of any source or with the pathogen-derived mimic of a sequence within a mammalian heat shock protein (hsp). Mammalian heat shock proteins such as HSP-60 (Swiss-Prot primary accession number P10809), HSP-70 (Swiss-Prot primary accession number P08107), HSP-90 alpha (Swiss-Prot accession number P07900), HSP-90 beta (Swiss-Prot accession number P08238), or any protein having 75% homology to each are examples. Bacterial homologues of mammalian heat shock proteins include mycobacterial hsp65 (belonging to the hsp60 family)

Heat shock proteins as cellular chaperones that are known to be upregulated in response to stress signals have a high degree of potential pathophysiological disease mechanism involvement. Hsp, the peptides that derive from them, and their cross-species mimics have been implicated in central nervous system disease such as schizophrenia and multiple sclerosis (Schwarz et al., *Am. J. Psychiatry,* 1999, 156:1103-4; Battistine et al., *Mol. Medicine,* 1995, 1:554-62), atherosclerosis (Benagiano, et al., *J. Immunol.,* 2005, 174:6509-17), rheumatoid arthritis (Anderton et al., *J. Exp. Med.,* 1995, 181:943-52; van Roon et al., *J. Clin. Invest.,* 1997, 100:459-63; Quintana et al., *J. Immunol.,* 2003, 171:3533-41), systemic lupus erythematosus (Minota et al., *J. Exp. Med.,* 1988, 168:1475-80), and diabetes (Raz et al., *Lancet* 358:1749-53).

HLA Derived Base Peptide Sequences

Immunologically relevant in a transplantation setting, HLA represent a large percentage of proteins to which recipient antibodies are directed. The gene products of HLA are seen to function as transplantation antigens. For example, studies analyzing the occurrence of acute graft versus host disease (GVHD) in relation to mismatched HLA alleles implicate the roles of HLA-DRB1 and HLA-DQB1 disparity between the donor and the recipient of a graft. Petersdorf et al., *Proc. Nat. Acad. Sci. USA,* 1996, 93: 15358-15363. Conversely, multiple examples of MHC-derived peptides have been reported as useful for immunotherapy. A study indicates that a large percentage of peptides bound to MHC on resting antigen presenting cells are MHC derived, leading to postulation that, other than functioning as stabilizers for the MHC heterodimers, these peptides may have roles in immunomodulation by competing with antigenic peptides, thereby increasing the threshold for antigenic stimulation. Murphy et al., *J. Am. Soc. Nephrol.,* 2003, 14:1053-1065. Peptides derived from Class II MHC are indeed reported to act as T-cell regulatory factors. (LeGuern, *Trends Immunol.,* 2003, 24:633-638). Further, synthetic peptides from a conserved region of class II MHC was able to mediate APC apoptosis and T cell hyporesponsiveness. Murphy, ibid. Elsewhere, a peptide derived from the predicted alpha helical domain of class II bound to I-Ak and inhibited antigen-dependent T-cell activation. Williams et al., *Immunol. Res.,* 1992, 11:11-23. Peptides derived from Class I MHC are reported to exert effects on the immune system through various mechanisms, such as anergy, deletion, immune deviation, cell cycle prevention, disruption of antigen presentation, and inhibition of T cell activation. Murphy and Krensky, *J. Am. Soc. Nephrol.,* 1999, 10:1346-1355.

Therefore, attenuating the immunological response to MHC is expected to reduce the severity and occurrence of GVHD. The above examples in the art showed the immunomodulatory effects using peptides having various contiguous amino acid sequences of HLA molecules. DSP based on the amino acid composition of HLA are expected to overcome such shortcomings and function as broadly relevant immunomodulators.

In an embodiment of the present invention, one or more epitopes comprising a mature HLA molecule are incorporated into the DSP. In another embodiment, one or more epitopes comprising the beta sheet of HLA are incorporated into the DSP. Synthetic peptides derived from the beta sheet of HLA-B7 have been shown to be immunodominant T-cell epitopes regulating alloresponses in GVHD. Freese and Zavazava (2002) Blood 99:3286-3292. These HLA-B7 derived allopeptides interfered with T cell mediated cytotoxicity targeted to HLA-B7 in vitro, and HLA-A2 derived allopeptides interfered with the cytotoxicity targeted to HLA-A2 in vitro, indicating allospecificity of these peptides.

Examples of amino acid compositions of HLA are provided herein. Known amino acid sequences of HLA proteins were obtained from GenBank and Swiss-Prot/trEMBL and were analyzed by using the ProtScale functions of ExPASy found at http://ca.expasy.org/cgi-bin/protscale.pl. Exemplary HLA sequences are GenBank Accession No. AAA36281, AAC02715, P01903 (alpha chain precursor), AAA17992, AAA59622 (heavy chain precursor), and AAA76608.

Organ Derived Base Peptide Sequences

A further category of derivation epitopes that may be useful for inducing tolerance are antigens derived from an organ to be transplanted itself. "Organ derived epitopes," as defined herein, are: peptide epitopes comprising organ-specific proteins. These proteins are potentially important as antigens in a context of organ transplant. For example, it has been shown that donor allopeptides are continuously shed from grafts, resulting in indirect recognition of such donor allopeptides by the recipient T cells. This results in chronic organ transplant rejection and prevents sustained chimerism. For example, in cardiac allografts, chronic rejection is manifested as a diffuse and accelerated form of atherosclerosis, termed cardiac allograft vasculopathy. Lee et al. *Proc. Nat. Acad. Sci. USA*, 2001, 98: 3276-3281. Perhaps invoking the similar mechanism as that used by the MHC derived peptides, peptides derived from the transplanted organ may induce sustained chimerism by preventing the stimulation of immune response by the transplantation. The suppression of immunologic reaction to such allopeptide may contribute to preventing chronic rejection and aid to achieve sustained chimerism.

Hence, in another embodiment of the present invention, one or more epitopes comprising the organ-derived proteins of the organ subject to transplantation.

Other relevant organ-derived DSP may include the epitopes of proteins considered to be organ-specific. A DSP suitable for alleviating the immune reaction to transplantation of an organ and promoting sustained chimerism is designed based on the epitopes of organ-specific proteins for the organ being transplanted.

Liver: Organ specific antigens for liver includes bile salt export pump (GenBank accession number O95342), which is considered to be predominantly expressed on liver cells.

Heart: An example of a protein found specifically in heart is Atrial natriuteric peptide-converting enzyme (pro-ANP-converting enzyme) (Corin) (Heart specific serine proteinase ATC2) (Swiss-Prot Accession No. Q9Y5Q5).

Pancreas: An example of an organ-specific protein for human pancreas is carboxypeptidase B1 (GenBank Accession No. 32880163).

Kidney: An example of an organ-specific protein for kidney is chloride channel ClC-6c (GenBank Accession No. 1770380).

Spleen: An example of spleen specific protein is Spleen tyrosine kinase (SYK) (Swiss-Prot Accession No. P43405).

Lung: An example of lung specific protein is Plunc (Palate lung and nasal epithelium clone protein) (Lung specific X protein)(GenBank Accession No. 9801236).

Empirically Derived Base Peptide Sequences

As described in the above sections, peptide sequences with some significance to a disease state or an adverse reaction may be identified through experimental investigation of a relevant epitope. These sequences may include non-naturally occurring peptide sequences that proved to be useful in treating a disease or a condition, an example found in the international patent application publication WO 2006/031727, U.S. Pat. No. 6,930,168 and the related scientific publication Stem et al., *Proc. Nat. Acad. Sci. USA*, 2005, 102:1620-25.

Further, epitopes are empirically determined by identifying candidate sequences by positional scanning of synthetic combinatorial peptide libraries (see, for example, D. Wilson et al., above; R. Houghten et al., above; Hernandez et al., *Eur J. Immunol.*, 2004, 34:2331-41), or by making overlapping peptide sequences of the entire protein of interest, and testing those peptides for immune reactivity (using, for example, any readout assay useful for such purposes, described in Current Protocols in Immunology Edited by John E Coligan, Ada M Kruisbeek, David H Margulies, Ethan M Shevach, Warren Strober NIH, John Wiley & Sons) in an in vitro or in vivo assay system appropriate for the disease and species the epitope is sought for. For example, for the design of a multiple sclerosis drug, an example of an appropriate system uses cells that derive from human subjects with MS.

After identifying a candidate epitope, a probable set of additional related epitopes are generated using modeling and prediction algorithms described in readily available references, for example WO 2000/042559, align and analyze the predicted binding of these probable epitopes using available prediction methods described in, for example, WO 2005/103679, WO 2002/073193 and WO 99/45954. Selecting from the peptides having the highest predicted activity/binding, take 40% of the predicted sequences and acquire the percentage of any given amino acid at each position. Use those percentages to create the rules for amino acid incorporation into a DSP synthesis.

Other Sources of Base Peptide Sequences

In addition to methodology and results described in the above sections, epitope sequences may be used as base peptide sequences, that are identified and included in the Immune Epitope Database, (available at http://www.immuneepitope.org/home.do, led by Alex Sette funded by the National Institute of Allergy and Infectious Diseases of the National Institute of Health, USA) or any sequences identified by processes performed and disclosed by commercial entities such as Mixtures Sciences of San Diego, or by Algonomics of Ghent Belgium.

Examples of epitopes identified as part of a naturally occurring, full length protein or synthetic peptides that were identified to have similar activities as such epitopes are shown in the table below.

TABLE I

Examples of epitopes

| Representative Disease | Peptide Sequence | Source/ Original Protein | Residue Number | ref | SEQ ID NO: |
|---|---|---|---|---|---|
| Myasthenia gravis | KSYCEIIVTHFPFDEQNC-SMK | AChR | a125-163, a256-269 | 35 | 1 |
|  | LGTWTYDGSVVAINPESD MKSDQESNNAAAEWKY-VAM VMDHILL | AChR | a386-411, h | 35 | 2 |
| Rheumatoid Arthritis | FKGEQGPK Type II | 263-270 Collagen | 38 | 3 |
|  | PKGQTGEBGIAG-FKGEQGPK | Type II Collagen | 251-270 | 38 | 4 |
|  | GEBGIAGFKGEQGPKGE-BGP A | Type II Collagen | 256-276 | 38 | 5 |

TABLE I-continued

Examples of epitopes

| Representative Disease | Peptide Sequence | Source/ Original Protein | Residue Number | ref | SEQ ID NO: |
|---|---|---|---|---|---|
| Multiple sclerosis | EVGELSRGKLYSLGNGRWMLTLAKNMEVRAI | CNPase | 343-373 | 5 | 6 |
| | GNGRWMLTLAKN-MEVRAIFT GYYGKGKPVPTQG | CNPase | 356-388 | 5 | 7 |
| | ASQKRPSQRH | MBP | 1-10 | | 8 |
| | LSRFSWGAEGQRPGFGYGG | MBP | 111-129 | 5 | 9 |
| | ASDYKSAHKGFKGVD | MBP | 131-145 | | 10 |
| | ASDYKSAH-KGLKGVDAQGTL SKIFK | MBP | 131-155 | 5 | 11 |
| | KYLATASTMDHARHGFL-PRH | MBP | 13-32 | 5 | 12 |
| | KGFKGVDAQGTLSKI | MBP | 139-153 | 49 | 13 |
| | AQGTLSKIFKLGGRDSRSGSP-MARR | MBP | 146-170 | 5 | 14 |
| | GTLSKIFKLGGRDSR | MBP | 148-162 | 49 | 15 |
| | SHGRTQDENPWHFFK | MBP | 76-91 | 49 | 16 |
| | YGRTQDENPVVHFFKNIVTPRTPPP | MBP | 80-103 | 49 | 17 |
| | ENPVVHFFKNIVTPRTP | MBP | 83-99 | 5 | 18 |
| | DENPVVHFFKNIVTPRTPP | MBP | 84-102 | 49 | 19 |
| | ENPVVHFFKNIVTPR | MBP | 85-99 | 49 | 20 |
| | VVHFFKNIVTPRTPPPSQGK | MBP | 86-105 | 49 | 21 |
| | EKAKYEAYKAAAAAA | Empirical | | 1 | 205 |
| | FSIHCCPPFTFNNSKKEIV | MOBP | 21-39 | 5 | 22 |
| | FLNSKKEIVDRKYSICKSG | MOBP | 31-49 | 5 | 23 |
| | CQFRVIGPRHPIRALVGDEV | MOG | 1-20 | 5 | 24 |
| | PIRALVGDEVELPCRISPGK | MOG | 11-30 | 5 | 25 |
| | ELPCRISPGKNATG-MEVGWY | MOG | 21-40 | 5 | 26 |
| | MEVGWYRPPFSRVVHLYRNGK | MOG | 35-55 | 5 | 27 |
| | HSLGKWLGHPDKF | PLP | 139-151 | 28 | |
| | HCLGKWLGHPDKFVGI | PLP | 139-154 | 5 | 29 |
| | NTWTTCQSIAFPSKTSASIG | PLP | 178-197 | 5 | 30 |
| | SKTSASIGSLCA-DARMYGVL | PLP | 190-209 | 5 | 31 |
| | GFYTTGAVRQIFGDYKTT | PLP | 89-106 | 5 | 32 |
| Penphigus vulgaris | REWVKFAKPCRE | Dsg3 | 49-60 | 8 | 33 |
| | QATQKITYRISGVGIDQ | Dsg3 | 78-94 | 45 | 34 |
| | PFGIFVVDKNTGDINIT | Dsg3 | 96-112 | 45 | 35 |
| | HLNSKIAFKIVSQEPAG | Dsg3 | 189-205 | 45 | 36 |
| | GTPMFLLSRNTGEVRTL | Dsg3 | 205-221 | 45 | 37 |
| | QCECNIKVKDVNDNFPM | Dsg3 | 250-266 | 45 | 38 |
| | SVKLSIAVKNKAEFHQS | Dsg3 | 342-358 | 45 | 39 |
| | NVREGIAFRPASKTFTV | Dsg3 | 376-392 | 45 | 40 |
| | RDSTFIVNKTITAEVLA | Dsg3 | 483-499 | 45 | 41 |
| | SARTLNNRYTGPYTF | Dsg3 | 512-526 | 48 | 42 |
| | QSGTMRTRHSTGGTN | Dsg3 | 762-786 | 48 | 43 |
| Insulin Dependent Diabetes | AALGIGTDSVILIKCDERGK | GAD65 | | 10 | 44 |
| | AFTSEHSHFSLKKGAAALGI | GAD65 | | 10 | 45 |
| | ATHQDIDFLIEEIERLGQDL | GAD65 | | 10 | 46 |
| | AVRPLWVRME | GAD65 | | 46 | 47 |
| | AYVRPLWVRME | GAD65 | | 46 | 48 |
| | CGRHVDVFKLWLM-WRAKGT TG | GAD65 | | 10 | 49 |
| | DERGKMIPSDLERRILEAKQ | GAD65 | | 10 | 50 |
| | DICKKYKIWMH-VDAAWGGGLL MS | GAD65 | | 10 | 51 |
| | DMVGLAADWLTSTANT-NMFT | GAD65 | | 10 | 52 |
| | EEILMHCQTTLKYAIKTGHP | GAD65 | | 10 | 53 |
| | ELLQEYNWELADQPQN-LEEIL M | GAD65 | | 10 | 54 |

TABLE I-continued

Examples of epitopes

| Representative Disease | Peptide Sequence | Source/ Original Protein | Residue Number | ref | SEQ ID NO: |
|---|---|---|---|---|---|
| | ERANSVTWNPHKMMGVPLQC | GAD65 | | 10 | 55 |
| | EYGTTMVSYQPLGDKVNFFR | GAD65 | | 10 | 56 |
| | EYLYNIIKNREGYEMVFDGK | GAD65 | | 10 | 57 |
| | EYVTLKKMREIIGWPGGSGD | GAD65 | | 10 | 58 |
| | GGSGDGIFSPGGAISNMYAM | GAD65 | | 10 | 59 |
| | GLLMSRKHKWKLSGVERANS | GAD65 | | 10 | 60 |
| | GSGDSENPGTARAWCQVAQKFTG | GAD65 | | 10 | 61 |
| | HATDLLPACDGERPTLAFLQ | GAD65 | | 10 | 62 |
| | IPPSLRTLEDNEERMSRLSK | GAD65 | | 10 | 63 |
| | KGTTGFEAHVDKCLELAEYLYN | GAD65 | | 10 | 64 |
| | KHYDLSYDTGDKALQCGRHV | GAD65 | | 10 | 65 |
| | KPCSCSKVDVNYAFLHATDL | GAD65 | | 10 | 66 |
| | KTGHPRYFNQLSTGLDMVGL | GAD65 | | 10 | 67 |
| | KVAPVIKARMME | GAD65 | | 46 | 68 |
| | KVAPVWVARMME | GAD65 | | 46 | 69 |
| | KVAPVWVRME | GAD65 | | 46 | 70 |
| | LAFLQDVMNILLQYVVKSFDRS | GAD65 | | 10 | 71 |
| | LEAKQKGFVPFLVSATAGTT | GAD65 | | 10 | 72 |
| | LLYGDAEKPAESGGSQPPRA | GAD65 | | 10 | 73 |
| | LSKVAPVIKARMMEYG | GAD65 | 526-541 | 46 | 74 |
| | MASPGSGFWSFGSEDGSGDS | GAD65 | | 10 | 75 |
| | NMYAMMIARFKMFPEVKEKG | GAD65 | | 10 | 76 |
| | PEVKEKGMAALPRLIAFTSE | GAD65 | | 10 | 77 |
| | QHRPLWVRME | GAD65 | | 46 | 78 |
| | QKFTGGIGIGNKLCALLYGD | GAD65 | | 10 | 79 |
| | QNCNQMHASYLFQQDKHYDL | GAD65 | | 10 | 80 |
| | QPPRAAARKAACACDQKPCSC | GAD65 | | 10 | 81 |
| | RTRPLWVRME | GAD65 | | 46 | 82 |
| | RVLPLWVRME | GAD65 | | 46 | 83 |
| | SFDRSTKVIDFHYPNELLQE | GAD65 | | 10 | 84 |
| | SRLSKVAPVIKARMMEYGTT | GAD65 | 524-543 | 46 | 85 |
| | TAGTTVYGAFDPLLAVADICKK | GAD65 | | 10 | 86 |
| | TNMFTYEIAPVFVLLEYVTL | GAD65 | | 10 | 87 |
| | VFDGKPQHTMVCKWYIPPSL | GAD65 | | 10 | 88 |
| | VNFFRMVISMPAATHQDIDF | GAD65 | | 10 | 89 |
| | VPLQCSALLVREEGLMQNCNQ | GAD65 | | 10 | 90 |
| | YTLPLWVRME | GAD65 | | 46 | 91 |
| systemic lupus erythematosus | QCSDISTKQMFKAVSEVCRIPTHL | human Ro60 | 101-125 | 28 | 92 |
| | ETEKLLKYLEAVEKVKRTRDELEVI | human Ro60 | 221-245 | 28 | 93 |
| | KARIHPFHILIALETYKTGH | hRo60 | 316-335 | 15 | 94 |
| | FKTVEPTGKRFLLAVDVSASMNQRV | human Ro60 | 361-385 | 28 | 95 |
| | MNQRVLGSILNASTVAAAMCIKALDA | human Ro60 | 381-405 | 28 | 96 |
| | PCPVTTDMTLQQVLMAMSQI | human | 421-445 | 28 | 97 |

TABLE I-continued

Examples of epitopes

| Representative Disease | Peptide Sequence | Source/ Original Protein | Residue Number | ref | SEQ ID NO: |
|---|---|---|---|---|---|
| | PAGGT PAGGTDCSLPMIWAQKTNTPADVFI | Ro60 hRo60 | 441-465 | 15 | 98 |
| | KTNTPADVFIVFTDNETFAG | human Ro60 | 456-475 | 28 | 99 |
| | MAALEAKICHQIEYYF | La/SSB | 10-25 | 20 | 100 |
| | DEYKNDVKNRSVYIKGFPTDATLDDI | La/SSB | 102-127 | 20 | 101 |
| | RSVYIKGFPTDATLDD | La/SSB | 111-126 | 20 | 102 |
| | TLDDIKEWLEDKGQVL | La/SSB | 123-138 | 20 | 103 |
| | WLEDKGQVLNIQMRRT | La/SSB | 130-145 | 20 | 104 |
| | KGQVLNIQMRRTLHKAFKGSIFVVFDSIESAKKFVE | La/SSB | 134-169 | 20 | 105 |
| | MRRTLHKAFKGSIFVV | La/SSB | 142-157 | 20 | 106 |
| | SIFVVFDSIESAKKFV | La/SSB | 153-168 | 20 | 107 |
| | VVFDSIESAKKFVETP | La/SSB | 156-171 | 20 | 108 |
| | SIESAKKFVETPGQKY | La/SSB | 160-175 | 20 | 109 |
| | TDLLILFKDDYFAKKNE | La/SSB | 178-194 | 20 | 110 |
| | ILFKDDYFAKKNEERK | La/SSB | 182-197 | 20 | 111 |
| | CHQIEYYFGDFNLPRDKFLK | La/SSB | 18-37 | 20 | 112 |
| | EEDAEMKSLEEKIGCL | La/SSB | 218-233 | 20 | 113 |
| | LEEKIGCLLKFSGDLD | La/SSB | 226-241 | 20 | 114 |
| | YYFGDFNLPRDKFLKE | La/SSB | 23-38 | 20 | 115 |
| | SNHGEIKWIDFVRGAK | La/SSB | 254-269 | 20 | 116 |
| | GEIKWIDFVRGAKEGI | La/SSB | 257-272 | 20 | 117 |
| | ALKGKAKDANNGLNQLR | La/SSB | 282-297 | 20 | 118 |
| | FNLPRDKFLKEQIKLD | La/SSB | 28-43 | 20 | 119 |
| | AKDANNGNLQLRNKEV | La/SSB | 286-301 | 20 | 120 |
| | LQLRNKEVTWELVEGE | La/SSB | 294-309 | 20 | 121 |
| | NKEVTWELVEGEVEKE | La/SSB | 298-313 | 20 | 122 |
| | EGEVEKEALKKIIEDQ | La/SSB | 307-322 | 20 | 123 |
| | EKEALKKIIEDQQESL | La/SSB | 311-326 | 20 | 124 |
| | RDKFLKEQIKLDEGWV | La/SSB | 32-47 | 20 | 125 |
| | GKGKGNKAAQPGSGKG | La/SSB | 338-353 | 20 | 126 |
| | GSKGKGKVQFQGKKTK | La/SSB | 349-363 | 20 | 127 |
| | FQGKKTKFASDDEHDE | La/SSB | 357-372 | 20 | 128 |
| | DENGATGPVKRAREET | La/SSB | 377-389 | 20 | 129 |
| | EETDKEEPASKQQKTE | La/SSB | 387-402 | 20 | 130 |
| | GWVPLEIMIKFNRLNRLTTDFNV | La/SSB | 45-67 | 20 | 131 |
| | PLEIMIKFNRLNRLTT | La/SSB | 48-63 | 20 | 132 |
| | IMIKFNRLNRLTTDFN | La/SSB | 51-66 | 20 | 133 |
| | KFNRLNRLTTDFNVIV | La/SSB | 54-69 | 20 | 134 |
| | DFNVIVEALSKSKAEL | La/SSB | 64-79 | 20 | 135 |
| | LSKSKAELMEISEDKT | La/SSB | 72-87 | 20 | 136 |
| | SKAELMEISEDKTKIR | La/SSB | 75-90 | 20 | 137 |
| | RRSPSKPLPEVTDEY | La/SSB | 89-104 | 20 | 138 |
| | PSKPLPEVTDEYKNDV | La/SSB | 93-108 | 20 | 139 |
| | KFGADARALMLQGVDLLADA | human HSP60 | 31-50 | 34 | 140 |
| autoimmunity in general | LKVGLQVVAVKAPGF | human HSP60 | 291-305 | 12 | 141 |
| | GGAVFGEEGLTLNLE | human HSP60 | 321-335 | 12 | 142 |
| | TLNLEDVQPHDLGKV | human HSP60 | 331-345 | 12 | 143 |
| | VGAATEIEMKEKKDR | human HSP60 | 381-395 | 12 | 144 |
| | VGGTSDVEVNEKKDR | human HSP60 | 406-420 | 12 | 145 |
| | IVLGGGCALLRCIPA | human HSP60 | 436-450 | 12 | 146 |
| | VLGGGVALLRVIPALDSLTPANED | human HSP60 | 437-460 | 36 | 147 |
| | GCALLRCIPALDSLT | human HSP60 | 441-455 | 12 | 148 |
| | RCIPALDSLTPANED | human HSP60 | 446-460 | 12 | 149 |

TABLE I-continued

Examples of epitopes

| Representative Disease | Peptide Sequence | Source/ Original Protein | Residue Number | ref | SEQ ID NO: |
|---|---|---|---|---|---|
| | EIIKRTLKIPAMTIA | human HSP60 | 446-480 | 12 | 150 |
| | VEKIMQSSSEVGYDA | human HSP60 | 491-505 | 12 | 151 |
| | MAGDFVNMVEKGIID | human HSP60 | 506-520 | 12 | 152 |
| | VNMVEKGIIDPTKVV | human HSP60 | 511-525 | 12 | 153 |
| | VAVTMGPKGRTVIIE | human HSP60 | 51-65 | 12 | 154 |
| | KGIIDPTKVVRTALL | human HSP60 | 516-530 | 12 | 155 |
| | PTKWRTALLDAAGV | human HSP60 | 521-535 | 12 | 156 |
| | ASLLTTAEWVTEIP | human HSP60 | 536-550 | 12 | 157 |
| | GETRKVKAH | HLA-A2 | 62-70 | 18 | 158 |
| | RKVKAHSQTHRVDLG | HLA-A2 | 65-79 | 18 | 159 |
| | RVDLGTLRGYYNQSE | HLA-A2 | 75-89 | 18 | 160 |
| | DGRLLRGHDQYAYDG | HLA-B7 | 106-120 | 18 | 161 |
| | GPEYWDRNTQIYKA | HLA-B7 | 56-69 | 18 | 162 |
| | WDRNTQIYKAQAQTDR | HLA-B7 | 60-75 | 18 | 163 |
| | RNTQIYKAQ | HLA-B7 | 62-70 | 18 | 164 |
| | RESLRNLRGYYNQSE | HLA-B7 | 75-89 | 18 | 165 |
| | GSHTLQSMYGCDVGP | HLA-B7 | 91-105 | 18 | 166 |
| | LNEDLRSWTAAD | HLA-B7 | 150-161 | 19 | 167 |
| | LNEDLRSWTAABTAA | HLA-B7 | 150-164 | 19 | 168 |
| | DKGQVLNIQ | HLA-DQ2 | 133-142 | 20 | 169 |
| | LEDKGQVLNIQMRR | HLA-DQ2 | 131-144 | 20 | 170 |
| | AFKGSIFVVFDSIE | HLA-DQ2 | 149-162 | 20 | 171 |
| | ESAKKFVET | HLA-DQ2 | 162-170 | 20 | 172 |
| | IESAKKFVETPGQK | HLA-DQ2 | 161-174 | 20 | 173 |
| | AKDANNGNLQLR | HLA-DQ2 | 286-297 | 20 | 174 |
| | EALKKIIED | HLA-DQ2 | 311-324 | 20 | 175 |
| | EQIKLDEGW | HLA-DQ2 | 36-47 | 20 | 176 |
| | LKEQIKLDEGWV | HLA-DQ2 | 36-47 | 20 | 177 |
| | AELMEISED | HLA-DQ2 | 75-87 | 20 | 178 |
| | SKAELMEISEDKT | HLA-DQ2 | 75-87 | 20 | 179 |
| | KGSIFWFD | HLA-DQ2, DQ7 | 149-162 | 20 | 180 |
| | AKDANNGNLQLRNK | HLA DQ2, DQ7 | 286-299 | 20 | 181 |
| | DANNGNLQL | HLA-DQ2, DQ7 | 288-299 | 20 | 182 |
| | IVEALSKSKAEL | HLA DQ2, DQ7 | 66-80 | 20 | 183 |
| | AFKGSIFVVFDSI | HLA-DQ7 | 149-161 | 20 | 184 |
| | GSIFVVFDSIESAK | HLA-DQ7 | 152-165 | 20 | 185 |
| | IFWFDSIESAKKF | HLA-DQ7 | 154-167 | 20 | 186 |
| | WFDSIESA | HLA-DQ7 | 154-167 | 20 | 187 |
| | ELMEISEDKTKIR | HLA-DQ7 | 78-90 | 20 | 188 |
| | EALYLVCGE | HLA-DQ8 | 35-47 | 20 | 189 |

II. Rules of Synthesis for Directed Sequence Polymers

Steps in the creation of a DSP sequentially encompass the following:

(a) Identify a protein having known or believed association with a pathology.

(b) Select from within the protein a peptide or peptides, each having a fixed sequence, that are associated with the pathology and immunologically relevant. If no peptides have been described, then peptides useful in the treatment of the pathology of interest are created. One exemplary method is to create a library of peptides that collectively span the entire length of the protein of interest. This may be done by, for example, partial endopeptidase digestion or by peptide synthesis. The library is screened for immunologically relevant peptides using appropriate detection methods such as binding affinity determination using antibodies detected in the sera of patients with the target pathology. The peptides may be further examined for immunogenicity useful for the treatment of the pathology in an in vitro or in vivo experimental system.

(c) the amino acid substitutions are decided based on either of two sets of rules, defined or empirical and are set forth below;

(d) Solid phase synthesis of DSP according to the rules is performed, and pharmaceutically acceptable formulation the DSP is delivered as a therapeutic.

The rules of synthesis for a composition comprising DSPs are outlined below. Briefly, a DSP may be envisioned as a polypeptide having a defined length that is either the same length as or multiples of the length of the base peptide sequence. For each residue position of the base peptide sequence, one or more substitute residue is defined. The rule of synthesis defines the ratio among the original base peptide residue for that position, the first substitute residue, the second substitute residue, the third substitute residue, and an alanine, to occupy any given residue position.

The substitute residues are defined according either: (1) to a rational comparison and finding of similarities of relevant characteristics of the original residue with those of the substitute residue or (2) to a comparison of reported experimental results on the relative activities of actual peptides having slight variations from the base sequence. The substitute residues defined in either of these two approaches are termed "conserved substitution" herein.

An example of a rational comparison and findings of similarity is the methods described by Kosiol et al., *J. Theoretical Biol.*, 2004, 228:97-106. Amino acids are grouped together in a matrix, referred therein as PAM replacement matrix. FIG. 4 is a table showing the amino acid similarity and grouping, according to Kosiol, based on the characteristics of the residues such as size, charge, hydrophobicity, etc., as shown in Table X of the reference. In FIG. 4, amino acids grouped together are considered interchangeable, with high likelihood of retaining characteristics common among the group, A comparison of experimental results showing the relative activities of peptides having slight variations from the base sequence can also be used as a basis for the rule for substitution. The sequences of the peptides responsible for observed changes are aligned and the type and percent presence of the new amino acid are noted. If there is more than one amino acid substitution at any given position of the peptide, the frequency of occurrence of an amino acid and the magnitude of activity change compared to the original sequence are taken into account to determine the order of prevalent substitution. Examples of the overall process leading up to the rule generation for DSP synthesis can be found using libraries (*Molec. Immunol.* 40:1047-1055; *Molec. Immunol.* 40:1063-74; *J Autoimmunity* 20:199-201; and *J Immunol* 163:6424-34), by making altered peptide ligands of overlapping peptides representing the entire protein of interest (Atkinson et al., *J. Clin. Invest.* 94:2125-29; Meini et al., *J. Clin. Invest.* 92:2633-43) or de novo (U.S. Pat. Nos. 7,058,515; 6,376,246; 6,368,861; 7,024,312; 6,376,246; 7,024,312; 6,961,664; 6,917,882). Briefly, a cellular material of interest is chosen as the assay system to rank the immunoreactivity of the peptides to be interrogated. Such an assay system can be either an in vitro or in vivo system, and can comprise adaptive or innate immune reactivity. Readouts for the assay system can be the up- or down-regulation of the status of the activation state of a protein, a change in the localization of a protein, the expression of the mRNA encoding for the protein, the relative concentration of a protein, changes in the generation of specific cell types, changes in cellular phenotype, changes in cellular activation, changes in cell number, changes in organ size or function, changes in animal behavior or phenotype. Once the assay or assays are performed the results are analyzed to determine the prevalence of any particular amino acid as a conserved substitution. If more than three residues in a given position within the peptide sequence are identified as generating a change in immunologic function, the top three residues first by frequency of representation in the interrogated peptides, and second by the magnitude of changes elicited. Once chosen, the relative amounts of the residues are defined.

As depicted in FIG. 5, each cassette, "y", has a set of amino acid ratios one to another that have a range of about 0-100 for the base (a), the primary change (b), the secondary change (c), and the tertiary change (d), whereas alanine (e) has a ratio of about 5-1000. The rules for the DSP synthesis continue with the combination of the cassettes in the order prescribed. The same block can be repeated either sequentially or separated by another block. On either side of the cassette sequence are N- and C-terminal modifiers. The number of cassettes is dictated by the requirements of the end length of the DSP which is required to be longer than 25 amino acids and shorter than 300 amino acids.

As described in FIG. 6, the instant invention envisions multiple epitopes to be defined as separate cassettes and synthesized sequentially. Cassette ratios within the same DSP may have different ratios of amino acids. Further, if there is less than three non-alanine amino acid substitutions, the percentage of the 'missing' substitution is added to the base sequence. Further, a cassette may be placed in any order with multiple appearances in the overall DSP synthesis. The N- and C-terminal Modifications reside prior to and after the entirety of the DSP cassettes respectively. As seen in FIG. 7A, a single base peptide sequence may have more than one ratio defined as a separate cassette in this example y1, y2, and y3. The individual cassettes can be placed in any order with multiple appearances in the overall DSP synthesis as seen in FIG. 7B. The synthesis rules seen in FIGS. 8A and 8B describe a DSP of the instant invention having portions of a single base peptide sequence with more than one ratio defined as a separate cassette.

FIG. 9 demonstrates how the instant invention envisions empirically derived ratios of amino acids at a particular position. The example uses data derived from a T cell activation assay using diabetogenic T cells derived from transgenic NOD.BCD2.5 mice (*J. Immunol.* 166:908-17*; J Autoimmunity* 20:199-201). The cells re interrogated with a combinatorial decamer library which resulted in a number of different peptides with inhibitory activity. The peptides with the highest activity were used to generate the amino acids at each position, as well as the ratio of different amino acids one to another.

A cassette may be repeated more than once. After a desired number of multiples of the cassette, if the desired length of the DSP is not yet reached, the DSP sequence is further defined by applying the same process, possibly using different ratio among the original, substitute, second substitute, and alanine residues.

N or C-terminal DSP modifiers may be added to the synthesis rules. The purpose of such modifiers include but are not limited to enhancing binding to specific proteins as in the case of RDG-based amino acid sequences (U.S. Pat. No. 5,773,412; 5,770,565) used as targeting moieties, or peptides that are known to bind to a wide array of HLA-DR species, such as AKAVAAWTLKAAA (SEQ ID NO: 236) (U.S. App. Pub. No. 2006/0018915) as a DR-targeting moiety. Such modifiers may include moieties which enhance complexation to delivery systems including sustained release delivery systems. Modifiers can be resorbable matrix constructs/synthesizable backbones such as PLGA. Modifiers can be protease resistant moieties such as D-amino acids.

Thus, for any given base peptide sequence, a set of synthesis rules is applied to yield a composition comprising reproducible, consistent mixture of DSPs.

III. Peptide Synthesis Methods

Any known solid phase synthesis appropriate for peptide synthesis may be used to synthesize a composition comprising DSPs, for example as originally described by Merrifield (*J. Am. Chem. Soc.*, 1963, 85:2149) and any variation thereof. More specifically, the synthesis is done in multiple steps by the Solid Phase Peptide Synthesis (SPPS) approach using Fmoc protected amino acids. SPPS is based on sequential addition of protected amino acid derivatives, with side chain protection where appropriate, to a polymeric support (bead). The base-labile Fmoc group is used for N-protection. After removing the protecting group (via piperidine hydrolysis) the next amino acid mixture is added using a coupling reagent (TBTU). After the final amino acid is coupled, the N-terminus is acetylated.

The resulting peptides (attached to the polymeric support through its C-terminus) are cleaved with TFA to yield the crude peptide. During this cleavage step, all of the side chains protecting groups are also cleaved. After precipitation with diisopropyl ether, the solid is filtered and dried. The resulting peptides are analyzed and stored at 2-8° C.

Additionally, any peptide synthesis method that allows synthesis incorporating more than one amino acid species at a controlled ratio in any given position of the peptide sequence is suitable for use with this invention. Further, as described below, DSPs may be peptidomimetics or include unnatural or modified amino acid, necessitating the adaptation to allow addition of such chemical species to the polymers synthesized up to that point.

The synthesis may include unnatural amino acids, or amino acid analogs. In some embodiments, the DSPs are comprised of naturally occurring and synthetic derivatives, for example, selenocysteine. Amino acids further include amino acid analogs. An amino acid "analog" is a chemically related form of the amino acid having a different configuration, for example, an isomer, or a D-configuration rather than an L-configuration, or an organic molecule with the approximate size and shape of the amino acid, or an amino acid with modification to the atoms that are involved in the peptide bond, so as to be protease resistant when polymerized in a polypeptide.

The DSPs for use in the present invention can be composed of L- or D-amino acids or mixtures thereof. As is known by those of skill in the art, L-amino acids occur in most natural proteins. However, D-amino acids are commercially available and can be substituted for some or all of the amino acids used to make DSPs of the present invention. The present invention contemplates DSPs containing both D- and L-amino acids, as well as DSPs consisting essentially of either L- or D-amino acids.

In certain embodiments, the DSPs of the present invention include such linear DSPs that are further modified by substituting or appending different chemical moieties. In one embodiment, such modification is at a residue location and in an amount sufficient to inhibit proteolytic degradation of the DSPs in a subject. For example, the amino acid modification may be the presence in the sequence of at least one proline residue; the residue is present in at least one of carboxy- and amino termini; further, the proline can be present within four residues of at least one of the carboxy- and amino-termini. Further, the amino acid modification may be the presence of a D-amino acid.

In certain embodiments, the subject DSPs is a peptidomimetic. Peptidomimetics are compounds based on, or derived from, peptides and proteins. The DSP peptidomimetics of the present invention typically can be obtained by structural modification of one or more native amino acid residues, e.g., using one or more unnatural amino acids, conformational restraints, isosteric replacement, and the like. The subject peptidomimetics constitute the continuum of structural space between peptides and non-peptide synthetic structures.

Such peptidomimetics can have such attributes as being non-hydrolyzable (e.g., increased stability against proteases or other physiological conditions which degrade the corresponding peptide DSPS), increased specificity and/or potency. For illustrative purposes, peptide analogs of the present invention can be generated using, for example, benzodiazepines (e.g., see Freidinger et al. in "Peptides: Chemistry and Biology," G. R. Marshall ed., ESCOM Publisher: Leiden, Netherlands, 1988), substituted gamma lactam rings (Garvey et al. in "Peptides: Chemistry and Biology," G. R. Marshall ed., ESCOM Publisher: Leiden, Netherlands, 1988, p 123), C-7 mimics (Huffman et al. in "Peptides: Chemistry and Biology," G. R. Marshall ed., ESCOM Publisher: Leiden, Netherlands, 1988, p. 105), keto-methylene pseudopeptides (Ewenson et al. *J. Med. Chem.*, 1986, 29:295; and Ewenson et al. in "Peptides: Structure and Function (Proceedings of the 9th American Peptide Symposium)," Pierce Chemical Co. Rockland, Ill., 1985), β-turn dipeptide cores (Nagai et al., *Tetrahedron Lett.*, 1985 26:647; and Sato et al. *J. Chem. Soc. Perkin Trans.*, 1986, 1:1231), β-aminoalcohols (Gordon et al. *Biochem. Biophys. Res. Commun.*, 1985, 126:419; and Dann et al. *Biochem. Biophys. Res. Commun.*, 1986, 134:71), diaminoketones (Natarajan et al. *Biochem. Biophys. Res. Commun.*, 1984, 124:141), and methyleneamino-modified (Roark et al. in "Peptides: Chemistry and Biology," G. R. Marshall ed., ESCOM Publisher: Leiden, Netherlands, 1988, p 134). Also, see generally, Session III: Analytic and synthetic methods, in "Peptides: Chemistry and Biology," G. R. Marshall ed., ESCOM Publisher: Leiden, Netherlands, 1988.

The molecular weight of a DSP composition can be adjusted during polypeptide synthesis or after the DSPs have been synthesized. To adjust the molecular weight during polypeptide synthesis, the synthetic conditions or the amounts of amino acids are adjusted so that synthesis stops when the polypeptide reaches the approximate length which is desired. After synthesis, polypeptides with the desired molecular weight can be obtained by any available size selection procedure, such as chromatography of the polypeptides on a molecular weight sizing column or gel, and collection of the molecular weight ranges desired. The present polypeptides can also be partially hydrolyzed to remove high molecular weight species, for example, by acid or enzymatic hydrolysis, and then purified to remove the acid or enzymes.

In one embodiment, the DSPs with a desired molecular weight may be prepared by a process which includes reacting a protected polypeptide with hydrobromic acid to form a trifluoroacetyl-polypeptide having the desired molecular weight profile. The reaction is performed for a time and at a temperature which is predetermined by one or more test reactions. During the test reaction, the time and temperature are varied and the molecular weight range of a given batch of test polypeptides is determined. The test conditions which provide the optimal molecular weight range for that batch of polypeptides are used for the batch. Thus, a trifluoroacetyl-polypeptide having the desired molecular weight profile can be produced by a process which includes reacting the protected polypeptide with hydrobromic acid for a time and at a temperature predetermined by test reaction. The trifluoroacetyl-polypeptide with the desired molecular weight profile is then further treated with an aqueous piperidine solution to form a low toxicity polypeptide having the desired molecular weight.

In one preferred embodiment, a test sample of protected polypeptide from a given batch is reacted with hydrobromic acid for about 10-50 hours at a temperature of about 20-28° C. The best conditions for that batch are determined by running several test reactions. For example, in one embodiment, the protected polypeptide is reacted with hydrobromic acid for about 17 hours at a temperature of about 26° C.

IV. Pharmaceutical Composition

One aspect of the present invention is a pharmaceutical composition comprising a DSP composition. As described below in the method of treatment as an aspect of this invention, the DSP composition produced by the process of the invention is useful in treatment of unwanted immune response, such as autoimmune diseases and transplantation rejection in a subject.

The DSPs of the present invention may be administered to the subject as a composition which comprises a pharmaceutically effective amount of DSPs and an acceptable carrier and/or excipients. A pharmaceutically acceptable carrier includes any solvents, dispersion media, or coatings that are physiologically compatible. Preferably, the carrier is suitable for oral, rectal, transmucosal (including by inhalation), parenteral, intravenous, intramuscular, intraperitoneal, intradermal, transdermal, topical, or subcutaneous administration. One exemplary pharmaceutically acceptable carrier is physiological saline. Other pharmaceutically acceptable carriers and their formulations are well-known and generally described in, for example, *Remington's Pharmaceutical Science* (18$^{th}$ Ed., ed. Gennaro, Mack Publishing Co., Easton, Pa., 1990). Various pharmaceutically acceptable excipients are well-known in the art and can be found in, for example, *Handbook of Pharmaceutical Excipients* (4$^{th}$ ed., Ed. Rowe et al. Pharmaceutical Press, Washington, D.C.). The composition can be formulated as a solution, microemulsion, liposome, capsule, tablet, or other suitable forms. The active component which comprises the copolymer may be coated in a material to protect it from inactivation by the environment prior to reaching the target site of action. The pharmaceutical compositions of the present invention are preferably sterile and non-pyrogenic at the time of delivery, and are preferably stable under the conditions of manufacture and storage. When desirable, the composition further comprises components to enhance stability, permeability, and/or bioavailability, such as particulate forms protective coatings, protease inhibitors or permeation enhancers for various routes of administration, including parenteral, pulmonary, nasal and oral.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pre-gelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well-known in the art.

In one embodiment, the oral composition is enterically-coated. Use of enteric coatings is well known in the art. For example, Lehman (1971) teaches enteric coatings such as Eudragit S and Eudragit L. The Handbook of Pharmaceutical Excipients, 2$^{nd}$ Ed., also teaches Eudragit S and Eudragit L applications. One Eudragit which may be used in the present invention is L30D55. Preparations for oral administration may be suitably formulated to give controlled release of the active compound.

The compositions may also be formulated in rectal compositions such as suppositories or retention enemas, e.g., containing conventional suppository bases such as cocoa butter or other glycerides.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

The compositions may be formulated for administration by injection, e.g., by bolus injection or continuous infusion in a parenteral, intravenous, intraperitoneal, intramuscular, or subcutaneous manner. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile pyrogen free water, before use.

In a preferred embodiment, compositions comprising DSP compositions are formulated in accordance with routine procedures as pharmaceutical compositions adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together. Where the composition is to be administered by infusion, it can be dispensed with an infusion bottle containing sterile pharmaceutical grade water or saline, with the intervals between administrations being greater than 24 hours, 32 hours, or more preferably greater than 36 or 48 hours. Where the composition is administered by injection, an ampoule of sterile water or saline for injection can be provided so that the ingredients may be mixed prior to administration.

In other embodiments of the present invention, the pharmaceutical compositions are regulated-release or sustained release formulations. DSP compositions of the present invention may be admixed with biologically compatible polymers or matrices which control the release rate of the copolymers into the immediate environment. Controlled or sustained release compositions include formulation in lipophilic depots (e.g., fatty acids, waxes, oils). One embodiment of sustained release formulations is transdermal patches.

In some embodiments of the present invention, pharmaceutical compositions comprise DSPs formulated with oil and emulsifier to form water-in-oil microparticles and/or emulsions. The oil may be any non-toxic hydrophobic material liquid at ambient temperature to about body temperature, such as edible vegetable oils including safflower oil, soybean oil, corn oil, and canola oil; or mineral oil. Chemically defined oil substance such as lauryl glycol may also be used.

The emulsifier useful for this embodiment includes Span 20 (sorbitan monolaurate) and phosphatidylcholine. In some embodiments, a DSP composition is prepared as an aqueous solution and is prepared into an water-in-oil emulsion dispersed in 95 to 65% oil such as mineral oil, and 5 to 35% emulsifier such as Span 20. In another embodiment of the invention, the emulsion is formed with alum rather than with oil and emulsifier. These emulsions and microparticles reduce the speed of uptake of DSPs, and achieve controlled delivery.

In another embodiment, the controlled and/or sustained delivery is achieved by implantable medical devices coated with sustained-release formulations, or implantable pharmaceutical formulation suitable for sustained-release of the active components.

In some embodiments of the invention, pharmaceutical compositions comprise a set of nucleic acid vectors encoding a DSP composition, which is expressed as polypeptides within a subject. The vectors may comprise transcription- and/or translation-controlling elements such that the timing and level of the DSPs composition produced may be regulated.

In some embodiments, the vectors also comprise one or more additional coding sequences, which encodes a therapeutically beneficial polypeptide or a second, different composition of DSPs that is not a member of the first DSP composition. In alternative embodiments, a pharmaceutical composition comprises one or more vectors, each encoding either: the DNA sequences for the DSPs of a first DSP composition, or the DNA sequences for the DSPs of a second DSPs composition or a therapeutically beneficial polypeptide, that is not a member of the first DSP composition. Such therapeutically beneficial polypeptide may be, for example, an immunomodulatory cytokine or a growth factor.

Some embodiments of the invention are pharmaceutical compositions for targeted delivery of the DSP composition of the invention. In such embodiments, a pharmaceutical composition comprises a DSP composition that is complexed with a targeting moiety. The targeting moiety allows localized delivery of the DSP composition to a desired location or microenvironment within the subject. A targeting moiety include, and may be selected from, the group comprising a chemical group or functionality such as biotin or simple sugars, a single or double stranded DNA sequence of various lengths, a single or double stranded RNA sequence of various lengths, a peptide of various lengths, an antibody including single chain antibodies, Fab', or modified antibodies, a lipid, or a glycolipid. More than one of such moiety may be used at the same time in combination. For examples of targeting moieties, see U.S. Pat. No. 6,268,488; U.S. Appl. Pub. No. 2003/0190676; and see, for example, www.covx.com/tech_creating.html.

In one embodiment of the invention, the complex has characteristics of a prodrug, causing the DSP composition to exhibit no pharmaceutical activity of the present invention until the dissolution of the complex in the subject. In another embodiment, the complex does not affect the activity of the DSP composition.

Any methods generally known to one skilled in the art may be used to produce a complex of the instant invention and a targeting moiety. The target moiety may be complexed to the DSPs by a chemical bond, which may be covalent, ionic, hydrophobic, or van der Waals force, directly or through another chemical entity. Alternatively, the target moiety may be co-localized with the DSPs through common medium such as a biocompatible resin within which the DSP composition is included. The manner of forming a complex is chosen also based on the active state of the instant invention while existing in the combination and whether a permanent complex or a transitory complex is desired.

In some embodiments, the pharmaceutical compositions also include additional therapeutically active agents. Such additional ingredient can be at least an additional DSP composition that binds to a different target, an antibody which binds to an unwanted inflammatory molecule or cytokine such as interleukin-6, interleukin-8, granulocyte macrophage colony stimulating factor, and tumor necrosis factor-α; an enzyme inhibitor such as a protease inhibitor aprotinin or a cyclooxygenase inhibitor; an antibiotic such as amoxicillin, rifampicin, erythromycin; an antiviral agent such as acyclovir; a steroidal anti-inflammatory such as a glucocorticoid; a non-steroidal anti-inflammatory such as aspirin, ibuprofen, or acetaminophen; or a non-inflammatory cytokine such as interleukin-4 or interleukin-10. Other cytokines and growth factors such as interferon-β, tumor necrosis factors, antiangiogenic factors, erythropoietins, thrombopoietins, interleukins, maturation factors, chemotactic protein, and their variants and derivatives that retain similar physiological activities may also be used as an additional ingredient.

Further, a form of vitamin D that is or becomes biologically active within the body of the subject receiving such form of vitamin D may also be used as an additional ingredient. The two main forms of vitamin D are: vitamin D3 or cholecalciferol, which is formed in the skin after exposure to sunlight or ultraviolet light, and ergocalciferol or vitamin D2 which is obtained by irradiation of plants or plant materials or foods. The differences are situated in the side chain. Vitamin D3 may be obtained from natural sources such as fatty fish such as herring and mackerel. In the body, two other forms of vitamin D3 can be found. Vitamin D3 is hydroxylated in the liver into 25-hydroxyvitamin D3 (25(OH)D), and subsequently in the kidney into 1,25-dihydroxyvitamin D3 (1,25(OH)2D), which is the active metabolite that stimulates the calcium absorption from the gut (Feldman et al., 2005). When 1,25(OH)2D is sufficiently available, 24,25-dihydroxyvitamin D (24,25 (OH)2D) is formed in the kidney, which is further catabolized.

Another class of therapeutically active agents useful as an additional agent is immune boosters which increases the production of common lymphoid precursors (CLPs) from the multilineage potential cells. An example of such agent is PBI-1402 developed by ProMetic in Quebec, Canada.

In some embodiments, the additional active therapeutically active agent is selected from the group consisting of anti-psoriasis creams, Sulfasalazine, glucocorticoids, propylthiouracil, methimazole, $I^{131}$, insulin, IFN-β1a, IFN-β1b, glucocorticoids, ACTH, avonex, azathiopurine, cyclophosphamide, UV-B, PUVA, methotrexate, calcipitriol, cyclophosphamide, OKT3, FK-506, cyclosporin A, azathioprine, and mycophenolate mofetil.

Another class of therapeutic agents that are useful to combine with the DSP composition of the invention is anti-obesity drugs, for example Lipitor. Anti-obesity drugs include P-3 agonists, CB-1 antagonists, appetite suppressants, such as, for example, sibutramine (Meridia), and lipase inhibitors, such as, for example, or list at (Xenical). The subject copolymers may also be used in methods of the invention in combination with drugs commonly used to treat lipid disorders in diabetic patients. Such drugs include, but are not limited to, HMG-CoA reductase inhibitors, nicotinic acid, bile acid sequestrants, and fibric acid derivatives. Polypeptides of the invention may also be used in combination with anti-hypertensive drugs, such as, for example, β-blockers, cathepsin S inhibitors and ACE inhibitors. Examples of β-blockers are:

acebutolol, bisoprolol, esmolol, propanolol, atenolol, labetalol, carvedilol, and metoprolol. Examples of ACE inhibitors are: captopril, enalapril, lisinopril, benazepril, fosinopril, ramipril, quinapril, perindopril, trandolapril, and moexipril.

In a specific embodiment, the disease to be treated by administration of the pharmaceutical composition of the invention is selected from the group consisting of multiple sclerosis, type-I diabetes, Hashimoto's thyroiditis, Crohn's disease, rheumatoid arthritis, systemic lupus erythematosus (SLE), gastritis, autoimmune hepatitis, hemolytic anemia, autoimmune hemophilia, autoimmune lymphoproliferative syndrome (ALPS), autoimmune uveoretinitis, glomerulonephritis, Guillain-Barré syndrome, psoriasis, myasthenia gravis, autoimmune encephalomyelitis, Goodpasture's syndrome, Grave's disease, paraneoplastic pemphigus, autoimmune thrombocytopenic purpura, scleroderma with anti-collagen antibodies, mixed connective tissue disease, pernicious anemia, polymyositis, idiopathic Addison's disease, autoimmune-associated infertility, bullous pemphigoid, Sjogren's syndrome, idiopathic myxedema and colitis.

The invention further provides a kit comprising (i) a composition comprising a DSP composition or DNA delivery vehicle comprising DNA encoding DSPs and (ii) instructions for administering the composition to a subject in need thereof at intervals greater than 24 hours, more preferably greater than 36 hours, for the treatment of a disease, such as an autoimmune disease. In one embodiment, the autoimmune disorder is multiple sclerosis. In a preferred embodiment, the DSP composition is formulated in dosages for administration of greater than about 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours, or any intervening interval thereof. In another embodiment of the kits described herein, the instructions indicate that the DSP is to be administered every about 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours, or any interval in between. Kits may comprise additional components, such as packaging, instructions, and one or more apparatuses for the administration of the copolymer, such as a hypodermic syringe V. Methods of Treatment The instant invention provides for a further improvement on the need to improve the effectiveness of peptide immunotherapies. The improvement takes form in an ability to dynamically administer the compound based on the ability of the compound to achieve sustained chimerism, or immune regulation—either active or passive, while generating either a $T_H1$ immune posture, or a $T_H2$ immune posture, and while producing anti-compound antibodies at either a low or a high level. Dynamic administration of random sequence copolymer is comprised of any combination of dose, regimen, route of administration, and/or formulation. This dynamic immunomodulation provides for increased effectiveness at any of the multiple stages of a disease within a particular patient, as well as the ability to treat multiple, pathogenic antigenic-determinant unrelated diseases more effectively.

The invention provides methods for the treatment or prevention of a disease in a subject, preferably in a human, which subject is afflicted with or is suspected to be afflicted with the disease. Another embodiment of the present invention is a method for prophylactically treating a subject at risk of developing e.g., an autoimmune disease by administering a DSP composition. A subject at risk is identified by, for example, determining the genetic susceptibility to an autoimmune disease by testing for alleles of HLA that are associated with such autoimmune disease, and/or based on familial history, or other genetic markers that correlate with such autoimmune disease. Alternatively, the subject at risk is a subject that is scheduled to have or has had organ transplantation. Such prophylactic treatment may additionally comprise a DSP composition that binds to a second HLA molecule associated with the disease or condition to be treated. The second HLA molecule may be a HLA-DQ or HLA-DR molecule.

One aspect of the invention provides methods of treating or preventing a disease, the method comprising administering to said subject a dosing regimen of an effective amount of a DSP composition for the amelioration of a disease treatable with the DSP composition, said effective amount delivered to said subject at time intervals greater than 24 hours, 36 hours, or more preferably greater than 48 hours. A related aspect of the invention provides a method for the treatment of a subject in need thereof, comprising administering to said subject a dosing regimen of an effective amount of a DSP composition for the amelioration of a disease treatable with the DSP composition, said effective amount delivered to the subject using a sustained-release formulation which administers the DSP composition over a period of at least 2 days, at least 4 days, or at least 6 days, wherein the effective amount is an amount that is effective if delivered daily.

In a specific embodiment, the method of the invention is effective in treating a disease selected from the group consisting of multiple sclerosis, type-I diabetes, Hashimoto's thyroiditis, Crohn's disease, rheumatoid arthritis, systemic lupus erythematosus (SLE), gastritis, autoimmune hepatitis, hemolytic anemia, autoimmune hemophilia, autoimmune lymphoproliferative syndrome (ALPS), autoimmune uveoretinitis, glomerulonephritis, Guillain-Barré syndrome, psoriasis, myasthenia gravis, autoimmune encephalomyelitis, Goodpasture's syndrome, Grave's disease, paraneoplastic pemphigus, autoimmune thrombocytopenic purpura, scleroderma with anti-collagen antibodies, mixed connective tissue disease, pernicious anemia, polymyositis, idiopathic Addison's disease, autoimmune-associated infertility, bullous pemphigoid, Sjogren's syndrome, idiopathic myxedema and colitis.

In some embodiments, the disease of the methods of the present invention is mediated by T-cells, and in particular $T_H1$ cells or cells with $T_H1$ immune posture, or is a disease which is exacerbated by an excess of inflammatory cytokines. In one aspect the application relates to methods of modulating an immune response by administering a composition comprising a DSP composition as described above. In some embodiments, the disease include, without limitation, acute inflammation, rheumatoid arthritis, transplant rejection, asthma, inflammatory bowel disease, uveitis, restenosis, multiple sclerosis, psoriasis, wound healing, lupus erythematosus, allergies, atopic dermatitis, and neuroprotection and any other autoimmune or inflammatory disorder that can be recognized by one of ordinary skill in the art.

A preferred embodiment of the invention is a method for treating a disease treatable by administering to a subject in need thereof a composition comprising a DSP composition wherein the disease is selected from the group consisting of allergies, asthma, atopic dermatitis, and neuroprotection. The invention is not limited to any particular DSP composition or mode of administration.

One aspect of the invention provides methods of modulating the immune response for preventing, treating, or attenuating, Host versus Graft Disease (HVGD) or Graft versus Host Disease (GVHD), in the case of organ transplantation, and in preventing, treating, or attenuating autoimmune disorders, by administering a composition comprising a DSP composition as described above. Thus, in another aspect this application relates to methods of inducing sustained chimerism in case of organ transplantation. Additionally, the present application relates to methods of selectively inhibiting T-cell response to a graft, consequently, increasing the chances of survival of the graft.

Transplantation systems such as organ transplantations and bone marrow reconstitution have become important and effective therapies for many life threatening diseases. However, immune rejection is still the major barrier for successful transplantation. This is manifested in functional deterioration and graft rejection in the case of organ transplantation (host-versus-graft disease, or HVGD. Another manifestation of pathological immune reactivity is GVHD that occurs in approximately 30% of bone marrow recipients. Up to half of those patients who develop GVHD may succumb to this process. This high morbidity and mortality has led to continuous interest in the possibility of controlling or preventing GVHD. Clinicopathologically, two forms of GVHD have been recognized. Acute GVHD develops within the first 3 months after bone marrow transplantation and features disorders of skin, liver and gastrointestinal tract. Chronic GVHD is a multi-organ autoimmune-like disease emerging from 3 months up to 3 years post-transplantation and shares features common to naturally occurring autoimmune disorders, like systemic lupus erythematosus (SLE) and scleroderma. The methods described herein may be used to treat both acute and chronic GVHD.

In a specific embodiment of the methods described herein, the DSP composition based on applicable organ-derived or HLA-derived native peptide sequences may be used for prevention and treatment of GVHD in all cases of organ transplantation that develop GVHD. A particularly suitable application of the present invention is in allogeneic bone marrow transplantation. A treatment regimen may comprise administrations of the random copolymer at intervals greater than 24, 30, 36, 42, or 48 hours, for up to 60 days, starting from 2 days prior to the graft. Other immunosuppressive drugs, such as cyclosporine, methotrexate and prednisone, may be administered with the DSP composition.

The method of the invention may also be applied to the prevention and treatment of GVHD in the course of bone marrow transplantation in patients suffering from diseases curable by bone marrow transplantation, including leukemias, such as acute lymphoblastic leukemia (ALL), acute nonlymphoblastic leukemia (ANLL), acute myelocytic leukemia (AML) and chronic myelocytic leukemia (CML), severe combined immunodeficiency syndromes (SCID), osteopetrosis, aplastic anemia, Gaucher's disease, thalassemia and other congenital or genetically-determined hematopoietic or metabolic abnormalities.

One aspect of the invention is the administration of a DSP composition to a subject in need there of, as described above, in combination with other therapeutic agents that are effective in treating the conditions that are treated by administration of the DSP, or conditions that accompany or occur concurrently with the conditions that are treated by administration of the DSP. The additional therapeutically active agents may treat the same or related disease as the DSP composition, or may be intended to treat an undesirable side effect of administration of the DSP composition, such as to reduce swelling at a site of intradermal injection. Alternatively, the other therapeutic agents enhance the activity of DSP compositions. Such additional therapeutic agents are, by way of example, antibodies, cytokines, growth factors, enzyme inhibitors, antibiotics, antiviral agents, anti-inflammatory including steroids, immune boosters, antimetabolites, soluble cytokine receptors, and vitamin D or agents that increase the level of circulating vitamin D. Additional therapeutically active agents also include copolymers which bind to a HLA molecule associated with the disease such as Copolymer-1, or another DSP composition. The HLA molecule may be an HLA-DQ molecule or an HLA-DR molecule. The enzyme inhibitor may be a protease inhibitor or a cyclooxygenase inhibitor. Examples of the therapeutically active agents to be administered in conjunction with the DSP composition are recited in Section IV, "Pharmaceutical Composition" section, though the administration of these agents are not limited to co-administration as a single composition. The additional therapeutic agents may be administered before, concomitantly with, or after the administration of the DSP composition, at such time that the effect of the additional therapeutic agents and the effect of the DSP composition overlap at some time point.

In particular, the method of present invention further comprises administering to said subject an anti-lymphocyte therapies. In such embodiments, the DSP composition of the present invention are administered to a patient with an autoimmune disease following an anti-lymphocyte therapy (e.g., anti-T cell or anti-B cell). In one embodiment, anti-T cell therapies may use antibodies, such as Campath-1H® (alemtuzumab; anti-CD52), OKT3 (anti-CD3), thymoglobulin (anti-thymocytic globulins), or anti-IL2R antibodies (e.g., daclizumab and basiliximab). Alternatively, anti-T cell therapies may use chemotherapy agents such as fludarabine, external-beam radiation therapy (XRT), and cyclophosphamide. In one embodiment, the anti-lymphocyte therapy agent selected from the group consisting of a polyclonal antibody or a monoclonal antibody. In certain embodiments, the polyclonal antibody is antithymocyte gamma globulin (ATGAM). In other embodiment, the antibody is a monoclonal antibody selected from the group consisting of alemtuzumab (Campath®), muromonab (OKT®3), daclizumab, and basiliximab. In another embodiment, the method of the invention comprises administering to said subject an anti B-cell therapy. In one embodiment, the anti-B-cell therapy anti CD-20 antibody such as the antibody Rituxan (Rituximab). The dosage of the above additional treatments to be administered to a subject varies with the precise nature of the condition being treated and the recipient of the treatment. The scaling of dosages for human administration can be performed according to art-accepted practices. For example, the dose for Campath-1H® will generally be in the range 1 to about 100 mg for an adult patient, usually administered daily for a period between 1 and 30 days. The preferred daily dose is 1 to 10 mg per day although in some instances larger doses of up to 40 mg per day may be used (see, e.g., U.S. Pat. No. 6,120,766). Although not wishing to be bound by any particular mechanism or theory, it is believed that such combination therapy can enhance the therapeutic efficacy without any potential long-term toxicity. To illustrate, Campath-1H® is introduced in a patient for initial induction immunosuppression. Then, the patient is administered a copolymer of the present invention in the absence of Campath-1H®

In a preferred embodiment, the DSP composition of the present invention can be administered with a form of vitamin D that is or becomes biologically active within the body of the subject receiving such form of vitamin D. The classical role of vitamin D that of an involvement in the regulation of calcium homeostasis. After the discovery of a vitamin D receptor (VDR) on peripheral blood mononuclear cells, interest in its role in the etiopathogenesis of certain autoimmune diseases increased. Vitamin D deficiency has been shown in increase susceptibility to experimental models of multiple sclerosis (MS), while vitamin D treatment suppressed these experimental models of MS. Further studies have shown that limiting the VDR signaling on T cells increases Th1 effector cells, while augmenting VDR signaling increases T regulatory cells. Thus, any increase in Vitamin D during the course of immunomodulatory therapy, such as those described herein, would have a potentially synergistic effect leading to increased efficacy of treatment as the vitamin D will assist in increasing the regulatory component of the treatment, while the peptide based immunotherapy will provide an epitope specific direction to the adaptive immune response In particular, for the role vitamin D plays in immunological phenomena, see M. T. Cantorna, *Progress in Biophys. Molec. Biol.* 2006 September; 92(1):60-4. Epub 2006 Feb. 28.) and Spach and Hayes, *J. Immunol.* 2005, 175:4199-4126.

In one embodiment of the methods described herein, the route of administration can be oral, intraperitoneal, transdermal, subcutaneous, by intravenous or intramuscular injection, by inhalation, topical, intralesional, or by infusion; liposome-mediated delivery; intrathecal, gingival pocket, rectal, intravaginal, intrabronchial, nasal, transmucosal, intestinal, ocular or otic delivery, or any other methods known in the art as one skilled in the art may easily perceive. Administration can be systemic or local. In the event more than one DSP composition is being administered to a subject during the same or overlapping time period, such additional therapeutic agent may be administered by a route different from that for the administration of the DSP composition.

In general, an embodiment of the invention is to administer a suitable dose of a therapeutic DSP composition that will be the lowest effective dose to produce a therapeutic effect, for example, mitigating symptoms. The therapeutic DSP compositions are preferably administered at a dose per subject, which corresponds to a dose per day of at least about 2 mg, at least about 5 mg, at least about 10 mg, or at least about 20 mg as appropriate minimal starting dosages, or about x mg, wherein x is an integer between 1 and 20. In one embodiment of the methods described herein, a dose of about 0.01 to about 500 mg/kg can be administered. In general, the effective dosage of the DSP composition of the present invention is about 50 to about 400 micrograms of the composition per kilogram of the subject per day. In one specific embodiment, the equivalent dosage per day, regardless of the frequency with which the doses are administered, is from about 5 to 100, or more preferably, from about 10 to 40, or more preferably about 20 mg/day. In another specific embodiment, each individual dosage in the treatment regimen is from about 5 to 100, or more preferably from about 10 to 40, or more preferably about 20 mg/dose.

However, it is understood by one skilled in the art that the dose of the DSP composition of the invention will vary depending on the subject and upon the particular route of administration used. It is routine in the art to adjust the dosage to suit the individual subjects. Additionally, the effective amount may be based upon, among other things, the size of the DSPs, the biodegradability of the DSPs, the bioactivity of the DSPs and the bioavailability of the DSPs. If the DSPs does not degrade quickly, such as is expected when the DSPs comprise unnatural amino acids or are peptidomimetics, is bioavailable and highly active, a smaller amount will be required to be effective. The actual dosage suitable for a subject can easily be determined as a routine practice by one skilled in the art, for example a physician or a veterinarian given a general starting point. For example, the physician or veterinarian could start doses of the DSP composition of the invention employed in the pharmaceutical composition at a level lower than that required in order to achieve the desired therapeutic effect, and increase the dosage with time until the desired effect is achieved. The dosage of the DSP composition may either be increased in the event the patient does not respond significantly to current dosage levels, or the dose may be decreased if an alleviation of the symptoms of the disorder or disease state is observed, or if the disorder or disease state has been ablated, or if an unacceptable side effects are seen with the starting dosage.

In one embodiment, a therapeutically effective amount of the DSP composition is administered to the subject in a treatment regimen comprising intervals of at least 36 hours, or more preferably 48 hours, between dosages. In another embodiment, the DSP composition is administered at intervals of at least 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours, or the equivalent amount of days. In some embodiments, the DSP composition is administered every other day, while in other embodiments it is administered weekly. If two different DSP compositions, or DSP composition with another therapeutic agent, are administered to the subject, such administration may take place at the same time, such as simultaneously, or essentially at the same time, such as in succession. Alternatively, their administration may be staggered. For example, two DSP compositions which are each administered every 48 hours may both be administered on the same days, or one may be administered one day and the other on the next day and so on in an alternating fashion.

Treatment regimens with longer dosing intervals, consequently often with lower total exposure of DSPs, are expected to induce lower titers of antibodies against DSPs themselves, while still inducing desired protective effects. Such reduction of neutralizing antibodies are desirable because it is considered likely to help DSP compositions to retain its effectiveness without being neutralized, and it is associated with reduced risk of anaphylactic shocks, providing safer treatments of diseases. Longer interval regimens are also desirable in treatment of some of the diseases, because they strengthen the bias for $T_H2$ responses, which is considered to be the mode of action for the treatment of these diseases by DSPs.

In other embodiments, the DSP composition is administered in a treatment regimen which comprises at least one uneven time interval, wherein at least one of the time intervals is at least 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours, or the equivalent amount of days.

In one embodiment, the DSP composition is administered to be subject at least three times during a treatment regimen, such that there are at least two time intervals between administrations. These intervals may be denoted $I_1$ and $I_2$. If the DSP composition is administered four times, then there would be an additional interval between the third and fourth administrations, $I_3$, such that the number of intervals for a given number "n" of administrations is n−1. Accordingly, in one embodiment, at least one of the time intervals between administrations is greater than about 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours. In another embodiment, at least 1%, 2%, 3%, 4%, 5%, 10%, 15%, 20%, 25%, 30%, 40%, 50%, 60%, 70%, 80%, 90% or 95% of the total number n−1 of time intervals are at least about 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours.

In yet another embodiment, the average time interval between administrations $((I_1+I_2+\ldots+I_{n-1})/n-1)$ is at least 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours, or at least two weeks.

In another embodiment, the dosage regimen consists of two or more different interval sets. For example, a first part of the dosage regimen is administered to a subject daily, every other day, or every third day, for example, at about 22 mg copolymer/m$^2$ body surface area of the subject, wherein the subject is a human. In some embodiment of the invention, the dosing regimen starts with dosing the subject every other day, every third day, weekly, biweekly, or monthly. The dosage for administration every other day or every third day may be up to about 65 mg/m$^2$ and 110 mg/m$^2$ respectively. For a dosing regimen comprising dosing of the random copolymer every week, the dose comprises up to about 500 mg/m$^2$, and for a dosing regimen comprising dosing of the random copolymer every two weeks or every month, up to 1.5 g/m$^2$ may be administered. The first part of the dosing regimen may be administered for up to 30 days, for example, 7, 14, 21, or 30 days. A subsequent second part of the dosing regimen with a different, longer interval administration with usually lower exposure (step-down dosage), administered weekly, every 14 days, or monthly may optionally follow, for example, at 500 mg/m$^2$ body surface area weekly, up to maximum of about 1.5 g/m$^2$ body surface area, continuing for 4 weeks up to two years, for example, 4, 6, 8, 12, 16, 26, 32, 40, 52, 63, 68, 78, or 104 weeks. Alternatively, if the disease goes into remission or generally improves, the dosage may be maintained or kept at lower than maximum amount, for example, at 140 mg/m$^2$ body surface area weekly. If, during the step-down dosage regimen, the disease condition relapses, the first dosage regimen may be resumed until effect is seen, and the second dosing regimen may be implemented. This cycle may be repeated multiple times as necessary.

In other embodiments of the invention, any of the methods of the invention may be practiced using sustained release formulation comprising a DSP composition. When administering a DSP composition of the invention using a sustained release formula, the overall exposure to the DSP is generally lower than in bolus administration. For example, a first part of the dosage regimen is administered to a subject daily, every other day, or every third day, for example, at about 22 mg DSP/m$^2$ body surface area of the subject, wherein the subject is a human. In some embodiment of the invention, the dosing regimen uses sustained release formula, dosing the subject every other day, every third day, weekly, biweekly, or monthly so that the copolymer is released during the interval. The dosage for administration every other day or every third day may be up to about 35 mg/m$^2$ and 65 mg/m$^2$ respectively. For a dosing regimen comprising dosing of the DSP composition every week, the dose comprises up to about 140 mg/m$^2$, and for a dosing regimen comprising dosing of the DSP composition every two weeks or every month, up to 750 mg/m$^2$ may be administered. The first part of the dosing regimen may be administered for up to 30 days, for example, 7, 14, 21, or 30 days. A subsequent second part of the dosing regimen with a different, longer interval administration with usually lower exposure (step-down dosage), administered weekly, every 14 days, or monthly may optionally follow, for example, at 140 mg/m$^2$ body surface area weekly, up to maximum of about 1.5 g/m$^2$ body surface area, continuing for 4 weeks up to two years, for example, 4, 6, 8, 12, 16, 26, 32, 40, 52, 63, 68, 78, or 104 weeks. Alternatively, if the disease goes into remission or generally improves, the dosage may be maintained or kept at lower than maximum amount, for example, at 140 mg/m$^2$ body surface area weekly. If, during the step-down dosage regimen, the disease condition relapses, the first dosage regimen may be resumed until effect is seen, and the second dosing regimen may be implemented. This cycle may be repeated multiple times as necessary.

For such sustained release administration, such method comprises applying a sustained-release transdermal patch or implanting a sustained-release capsule or a coated implantable medical device so that a therapeutically effective dose of the copolymer of the present invention is delivered at defined time intervals to a subject of such a method. The DSP composition of the subject invention may be delivered via a capsule which allows regulated-release of the DSPs over a period of time. Controlled or sustained-release compositions include formulation in lipophilic depots (e.g., fatty acids, waxes, oils). Also comprehended by the invention are particulate compositions coated with polymers (e.g., poloxamers or poloxamines). In certain embodiments, a source of a DSP composition is stereotactically provided within or proximate to the area of autoimmune attack, for example, near the pancreas for the treatment of IDDM.

An improvement in the symptoms of a subject afflicted with a disease as a result of administration of the DSP composition may be noted by a decrease in frequency of recurrences of episodes of the disease symptoms, by decrease in severity of symptoms, and by elimination of recurrent episodes for a period of time after the start of administration. A therapeutically effective dosage preferably reduces symptoms and frequency of recurrences by at least about 20%, for example, by at least about 40%, by at least about 60%, and by at least about 80%, or by about 100% elimination of one or more symptoms, or elimination of recurrences of the autoimmune disease, relative to untreated subjects. The period of time can be at least about one month, at least about six months, or at least about one year.

For example, an improvement in the symptoms of a subject afflicted with arthritis or any other autoimmune disorder which results in inflammation of the joints may be noted by a reduction in edema of one or more joints, by a reduction in inflammation in one or more joints, or by an increase in mobility in one or more joints. A therapeutically effective dosage preferably reduces joint inflammation and edema and improves mobility by at least about 20%, more preferably by at least about 40%, even more preferably by at least about 60%, and even still more preferably by at least about 80%, relative to untreated subjects.

DEFINITIONS

The term "associated with" means "coexistent with" or "in correlation with." The term does not necessarily indicate causal relationship, though such relationship may exist.

The term "binding" refers to a direct association between two molecules, due to, for example, covalent, electrostatic, hydrophobic, ionic and/or hydrogen-bond interactions under physiological conditions, and including interactions such as salt bridges and water bridges.

The term "HLA molecule" means any class II major histocompatibility complex glycoproteins.

The term "immunomodulation" means the process of increasing or decreasing the immune system's ability to mount a response against a particular antigenic determinant through the T-cell receptor ("TCR")'s recognition of complexes formed by major histocompatibility complex ("MHC") and antigens.

The term "immunosuppression" means the depression of immune response and reactivity in recipients of organ or bone marrow allotransplants.

The term "MHC activity" refers to the ability of an MHC molecule to stimulate an immune response, e.g., by activating T cells. An inhibitor of MHC activity is capable of suppressing this activity, and thus inhibits the activation of T cells by MHC. In preferred embodiments, a subject inhibitor selectively inhibits activation by a particular class II MHC isotype or allotype. Such inhibitors may be capable of suppressing a particular undesirable MHC activity without interfering with all MHC activity in an organism, thereby selectively treating an unwanted immune response in an animal, such as a mammal, preferably a human, without compromising the animal's immune response in general.

The term "organ-specific protein" or "organ-specific antigen" means proteins that are expressed predominantly or exclusively by cells comprising a certain organ.

The term "patient" refers to an animal, preferably a mammal, including humans as well as livestock and other veterinary subjects.

The terms "peptide", "polypeptide" and "protein" are used interchangeably herein. These terms refer to unmodified amino acid chains, and also include minor modifications, such as phosphorylations, glycosylations and lipid modifications. The terms "peptide" and "peptidomimetic" are not mutually exclusive and include substantial overlap.

A "peptidomimetic" includes any modified form of an amino acid chain, such as a phosphorylation, capping, fatty acid modification and including unnatural backbone and/or side chain structures. As described below, a peptidomimetic comprises the structural continuum between an amino acid chain and a non-peptide small molecule. Peptidomimetics generally retain a recognizable peptide-like polymer unit structure. Thus, a peptidomimetic may retain the function of binding to a HLA protein forming a complex which activates autoreactive T cells in a patient suffering from an autoimmune disease.

The term "amino acid residue" is known in the art. In general the abbreviations used herein for designating the amino acids and the protective groups are based on recommendations of the IUPAC-IUB Commission on Biochemical Nomenclature (see *Biochemistry* (1972) 11:1726-1732). In certain embodiments, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.

The term "amino acid residue" further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject compound can include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

Most of the amino acids used in the DSPs of the present invention may exist in particular geometric or stereoisomeric forms. In preferred embodiments, the amino acids used to form the subject DSPs are (L)-isomers, although (D)-isomers may be included in the DSPs such as at non-anchor positions or in the case of peptidomimetic versions of the DSPs.

"Prevent", as used herein, means to delay or preclude the onset of, for example, one or more symptoms, of a disorder or condition.

"Treat", as used herein, means at least lessening the severity or ameliorating the effects of, for example, one or more symptoms, of a disorder or condition.

"Treatment regimen" as used herein, encompasses therapeutic, palliative and prophylactic modalities of administration of one or more compositions comprising one or more DSP compositions. A particular treatment regimen may last for a period of time at a particular dosing pattern, which will vary depending upon the nature of the particular disease or disorder, its severity and the overall condition of the patient, and may extend from once daily, or more preferably once every 36 hours or 48 hours or longer, to once every month or several months.

The terms "structure-activity relationship" or "SAR" refer to the way in which altering the molecular structure of drugs alters their interaction with a receptor, enzyme, etc.

The practice of the present invention will employ, where appropriate and unless otherwise indicated, conventional techniques of cell biology, cell culture, molecular biology, transgenic biology, microbiology, virology, recombinant DNA, and immunology, which are within the skill of the art. Such techniques are described in the literature. See, for example, Molecular Cloning: A Laboratory Manual, 3rd Ed., ed. by Sambrook and Russell (Cold Spring Harbor Laboratory Press: 2001); the treatise, Methods In Enzymology (Academic Press, Inc., N.Y.); Using Antibodies, Second Edition by Harlow and Lane, Cold Spring Harbor Press, New York, 1999; Current Protocols in Cell Biology, ed. by Bonifacino, Dasso, Lippincott-Schwartz, Harford, and Yamada, John Wiley and Sons, Inc., New York, 1999; and PCR Protocols, ed. by Bartlett et al., Humana Press, 2003; PHARMACOLOGY A Pathophysiologic Approach Edited by Josehp T. DiPiro, Robert Talbert, Gary, Yee, Gary Matzke, Barbara Wells, and L. Michael Posey. 5th edition 2002 McGraw Hill; Pathologic Basis of Disease. Ramzi Cotran, Vinay Kumar, Tucker Collins. 6th Edition 1999. Saunders.

Example 1

Preparation of a DSP Composition from Fictitious Base Peptides

For ease of understanding, as an illustration, preparation of a DSP composition deriving from two fictitious peptide sequences, representing a known epitope, is described and shown in the table depicted in FIG. 6. In this illustration, the cassettes consist of five amino acids each, (x1, x2, x3, x4, x5=THMCE (SEQ ID NO: 237) in $y_1$ and PWKNA (SEQ ID NO: 238) in $y_2$). THMCE (SEQ ID NO: 237) is defined as having an input ratio of a=7, b=1, c=1, d=1, e=10. PWKNA (SEQ ID NO: 238) is defined as having an input ratio of a=1, b=3, c=3, d=3, e=20. For synthesis, the identity of group of amino acids occupying each amino acid position for each peptide is determined using the preferred method of amino acid substitution described by Kosiol et al., *J. Theoretical Biol.* 228:97-106, 2004, as shown in FIG. 4 (or less preferably an equivalent means of systematically altering amino acids), and the overall ratio of amino acids that occupy each of such positions in the resulting collective DSP composition is given above. Each cassette, $y_1$ and $y_2$, will twice be repeated two times, generating an order of $y_1 y_1 y_2 y_2 y_1 y_1 y_2 y_2$. $N_n$ are the number of times the sequence within the cassette is to be repeated, and in our fictitious example N=2. MN can be any type of modifying moiety. MN must be amenable to solid phase synthesis methods. For this fictitious example, a modifying moiety of amino acids that would target the DSP to a certain location within a subject is chosen, such as an RGD-based sequence motif on a particular integrin such as alphaV-beta3. In this example the C-terminal modifier will also be an RGD-based motif, but comprised of D-amino acids.

The DSP composition as described above is prepared using a solid phase peptide synthesis method as described elsewhere in this disclosure.

Example 2

Preparation of a DSP Composition from MBP(83-99)

Myelin basic protein is implicated in the pathology of multiple sclerosis, and several epitopes have been identified and proven to be relevant in the disease symptoms and progression. One such epitope spans amino acid residues 83 to 99 of myelin basic protein (MBP(83-99). COP-1 is thought to target the same binding pocket of HLA as MBP(83-99) does. A DSP composition is defined and prepared using MBP (83-99) as the base peptide sequence.

The methods and rules to define the identity of amino acids for each position of the resulting peptides are described above in Example 1. The actual application of such rules are illustrated in the tables of FIG. 8A-B. As with Example 1, the DSP composition is synthesized using a solid phase peptide synthesis method.

The following references are exemplary sources of epitopes useful as base peptide sequences. Numbers to the left are the reference numbers of Table I.
1 U.S. Pat. No. 6,930,168—issued Aug. 16, 2005 to Strominger et al.
2 U.S. Pat. No. 7,118,874—issued Oct. 10, 2006 to Torres
3 U.S. Publ. No.: 2006/0045888A1—published Mar. 2, 2006 to Punnonen et al.
4 WO 2005/032482—published Apr. 14, 2005 in the name of Bayhill Therapeutics, Inc.
5 WO 2005/074579—published Aug. 18, 2005 in the name of Mixture Sciences, Inc.
6 WO 2006/031727—published Mar. 23, 2006 in the name of President and Fellows of Harvard College
7 ANDERTON, S., et al., "Activation of T Cells Recognizing Self 60-kD Heat Shock Protein Can Protect Against Experimental Arthritis", J. Exp. Med. Vol. 181, 943-952 (1995).
8 ANGELINI, G., et al. "Preliminary Data on *Pemphigus Vulgaris* Treatment by a Proteomics-defined peptide: a case report", Journal of Translational Medicine", 4:43, 1-7 (2006).
9 ATASSI, M Z, et al., "On the initial trigger of myasthenia gravis and suppression of the disease by antibodies against the MHC peptide region involved in the presentation of a pathogenic T-cell epitope", Crit. Rev Immunol. 21(1-3): 1-27 (2001) (Abstract).
10 ATKINSON, M., et al., "Cellular immunity to a determinant common to glutamate decarboxylase and coxsackie virus in insulin dependent diabetes", J Clin Invest., Vol. 94, 2125-2129 (1994).
11 BENACERRAF, B., "The role of MHC gene products in immune regulation and its relevance to alloreactivity", Nobel Lecture, Harvard Medical School, 597-623 (1980).
12 BENAGIANO, M., et al., "Human 60-kDa heat shock protein is a target autoantigen of T cells derived form atherosclerotic plaques", The Journal of Immunology, 174: 6509-6517, (2005).
13 BIAN, H., etl al., "The use of bioinformatics for identifying class II-restricted T-cell epitopes", Methods 29, 299-309, (2003)
14 BOOG, C., et al., "Two monoclonal antibodies generated against human hsp60 show reactivity with synovial membranes of patients with juvenile chronic arthritis", J. Exp. Med., Vol. 175, 1805-1810, (1992).
15 DESHMUKH, U., et al., "Ro60 peptides induce antibodies to similar epitopes shared among lupus-related autoantigens", The Journal of Immunology, 164: 6655-6661 (2000).
16 EREZ-ALON, N., et al., Immunity to p53 induced by an idiotypic network of anti-p53 antibodies: generation of sequence-specific anti-DNA antibodies and protection form tumor metastasis", Cancer Research, 58, 5447-5452 (1998).
17 FRANCIS, J., et al., "Peptide-based vaccination: where do we stand", Curr Opin Allergy Clin Immunol 5:537-543 (2005).
18 FREESE, A., et al., "HLA-B7 B-pleated sheet-derived synthetic peptides are immunodominant T-cell epitopes regulating alloresponces", Blood, Vol. 99, No. 9, 3286-3292 (2002).
19 GODKINS, A., et al., "Use of eluted peptide sequence data to identify the binding characteristics of peptides to the insulin-dependent diabetes susceptibility allele HLA-DQ8 (DQ 3.2)", International Immunology, Vol. 9, No. 6, pp 905-911, (1997)
20 KOSMOPOULOU, A., "T-cell Epitopes of the La/SSB Autoantigen: Prediction Based on the Homology Modeling of HLA-DQ2/DQ7 with the Insulin-B Peptide/HLA-DQ8 Complex", Journal of Computational Chemistry, Vol 27, No. 9, pp 1033-1044, (2006)
21 LIN, M., et al., "Development and Characterization of Desmoglein-3 Specific T Cells from Patients and Pemphigus Vulgaris", J. Clin. Invest., Vol. 99, No. 1, 31-40 (1997).
22 LIN, Q., et al., "Genetic dissection of the effects of stimulatory and inhibitory IgG Fc receptors on murine lupus", The Journal of Immunology, 177: 1646-1655 (2006).
23 LU, Y., et al., "Identification of Kinectin as a Novel Behcet's Disease Autoantigen", Arthritis Res. Ther. 2005; 7(5): R1133-R1139, (2005),
24 MAYNARD, J., et al., "Structure of an Autoimmune T Cell Receptor Complexed with Class II Peptide-MHC: Insights into MHC Bias and Antigen Specificity", Immunity, Vol. 22, 81-92 (2005).
25 MEINL, E., et al., "Genetic dissection of the effects of stimulatory and inhibitory IgG Fc receptors on murine lupus", J. Clin. Invest., Vol. 92, 2633-2643 (1993).
26 MINOTA, S., et al., "Autoantibodies to the constitutive 73-kD member of the hsp70 family of heat shock proteins in systemic lupus erythematosus", J. Exp. Med., Vol. 168, 1475-1480 (1988).
27 MÜLLER, R., et al. "IgG reactivity against non-conformational NH$_2$-terminal epitopes of the desmoglein 3 ectodomain relates to clinical activity and phenotype of pemphigus vularis", Experimental Dermatology, 15: pp. 606-614, (2006)
28. PAL, R., et al., "Evidence for multiple shared antigenic determinants within Ro60 and other Lupus-related ribonucleoprotein autoantigens in human autoimmune responses", The Journal of Immunology, 175: 7669-7677 (2005).
29. PAPASSAVAS, A. C., "HLA peptide-mediated strategies for 29 modulation of cellular and humoral immune responses in transplantation", Current Pharmacogenomics, Vol. 1, No. 1, 17-36 (2003).
30. PEDOTTI, R., et al., "Severe anaphylactic reactions to glutamic acid 30 decarboxylase (GAD) self peptides in NOD mice that spontaneously develop autoimmune type 1 diabetes mellitus", BMC Immunology, 4:2 (2003).
31. PINCHUK, P., et al., "Antigenicity of polypeptides (poly alpha amino acids)", Microbiology Department, New Jersey College of Medicine and Dentistry, 673-679 (1965).
32. PINILLA, C., et al., "Advances in the use of synthetic combinatorial chemistry: Mixture-based libraries", Nature Medicine, Vol. 9, No. 1, pp. 118-126, (2003).
33. QUANDT, J. S. et al., "Peptidic complex mistures as therapeutic agents in CNS autoimmunity", Molecular Immunology, 40:1075-1087, (2004).
34. QUINTANA, F., et al., "DNA fragments of the human 60-kDa heat shock protein (HSP60) vaccinate against adjuvant arthritis: identification of a regulatory HSP60 peptide", The Journal of Immunology, 171: 3533-3541 (2003).
35. RAGJEB, et. al., "Myasthenia gravis patients, but not healthy subjects, recognize epitopes that are unique to the epsilon-subunit of the acetylcholine receptor." J. Neuroimmunol. 2005 February; 159(1-2): 137-45. Epub 2004 Nov. 23
36. RAZ, R., et al., "B-cell function in new-onset type diabetes and immunomodulation with heat-shock protein peptide (DiaPep27): a randomised, double-blind, phase II trial", The Lancet, Vol. 358, 1749-1753 (2001).
37. ROSLONIEC, E., et al., "HLA-DR1 (DRB1*0101) and DR4 (DRB1*0401) Use the Same Anchor Residues for Binding an Immunodominant Peptide Derived from Human Type II Collagen", The Journal of Immunology, 168:253-259, (2002)
38. SAKURAI, Y. et al., "Analog Peptides of type II collagen can suppress arthritis in HLA-DR4 (DRB1*0401) transgenic mice", Arthritis Research & Therapy, 8:R150, (2006)
39. SCHWARZ, M., et al., "Antibodies to heat shock proteins in schizophrenic patients: Implications for the mechanism of the disease", Am J Psychiatry 156:7, 1103-1104 (1999).
40. SEKIGUCHI, M., et al., "Dominant Autoimmune Epitopes Recognized by Pemphigus Antibodies Map to the N-Terminal. Adhesive Region of Desmogleins", The Journal of Immunology, 167:5439-5448 (2001).
41. STERN, Joel N. H., et al., "Peptide 15-mers of defined sequence that substitute for random amino acid copolymers in amelioration of experimental autoimmune encephalomyelitis", PNAS, 102:5, (2005)
42. ULMANSKY, R., et al., "Resistance to adjuvant arthritis is due to protective antibodies against heat shock protein surface epitopes and the induction of IL-10 secretion", The Journal of Immunology, 168: 6463-6469 (2002).
43. VAN ROON, J., et al., "Stimulation of suppressive T cell responses by human but not bacterial 60-kD heat-shock protein in synovial fluid of patients with rheumatoid arthritis", J. Clin. Invest., Vol. 1100, No. 2, 459-463 (1997).
44. VELDMAN, C., et al., "Detection of Low Avidity Desmoglein 3-reactive T cells in pemphigus vulgaris using HLA-DR-beta*0402 tetramers", Clinical Immunology, 1-8 (2006)
45. VELDMAN, C., et al., "T Cell Recognition of Desmoglein 3 peptides in Patients with Pemphigus Vulgaris and Healthy Individuals", The Journal of Immunology, 172: 3883-3892 (2004).
46. WILSON, D., "GAD-about BDC2.5: Peptides that stimulate BDC2.5 T cells and inhibit IDDM", Journal of Autoimmunity 20, 199-201 (2003).
47. WILSON, D. et al, "Specificity and degeneracy of T cells", Molecular Immunology 40:1047-1055, (2004)
48. WUCHERPFENNIG, K., et al., "Structural basis for major histocompatibility complex (MHC)— linked susceptibility to autoimmunity: Charged residues of a single MHC binding pocket confer selective presentation of self-peptides in pemphigus vulgaris", Proc. Natl. Acad. Sci. USA, Vol. 92, 11935-11939 (1995).
49. WUCHERPFENNIG, K., et al., "Structural requirements for binding of an immunodominant myelin basic protein peptide to DR2 isotypes and for its recognition by human T cell clones" J. Exp. Med., Vol. 179, 279-290 (1994).
50. YURASOV, S., et al., "Persistent expression of autoantibodies in SLE patients in remission", The Journal of Experimental Medicine", Vol. 203, No. 10, 2255-2261 (2006).

The contents of any patents, patent applications, patent publications, or scientific articles referenced anywhere in this application are herein incorporated in their entirety.

```
Sequence Listings in addition to Table I

SEQ ID NO: 190
HSP-60 (human):
MLRLPTVFRQ MRPVSRVLAP HLTRAYAKDV KFGADARALM
LQGVDLLADA VAVTMGPKGR TVIIEQSWGS PKVTKDGVTV
AKSIDLKDKY KNIGAKLVQD VANNTNEEAG DGTTTATVLA
RSIAKEGFEK ISKGANPVEI RRGVMLAVDA VIAELKKQSK
PVTTPEEIAQ VATISANGDK EIGNIISDAM KKVGRKGVIT
VKDGKTLNDE LEIIEGMKFD RGYISPYFIN TSKGQKCEFQ
DAYVLLSEKK ISSIQSIVPA LEIANAHRKP LVIIAEDVDG
EALSTLVLNR LKVGLQVVAV KAPGFGDNRK NQLKDMAIAT
GGAVFGEEGL TLNLEDVQPH DLGKVGEVIV TKDDANLLKG
KGDKAQIEKR IQEIIEQLDV TTSEYEKEKL NERLAKLSDG
VAVLKVGGTS DVEVNEKKDR VTDALNATRA AVEEGIVLGG
GCALLRCIPA LDSLTPANED QKIGIEIIKR TLKIPAMTIA
KNAGVEGSLI VEKIMQSSSE VGYDAMAGDF VNMVEKGIID
PTKVVRTALL DAAGVASLLT TAEVVVTEIP KEEKDPGMGA
MGGMGGGMGG GMF SEQ ID NO: 191
HSP-70 (human):
MAKAAAIGID LGTTYSCVGV FQHGKVEIIA NDQGNRTTPS
YVAFTDTERL IGDAAKNQVA LNPQNTVFDA KRLIGRKFGD
PVVQSDMKHW PFQVINDGDK PKVQVSYKGE TKAFYPEEIS
SMVLTKMKEI AEAYLGYPVT NAVITVPAYF NDSQRQATKD
AGVIAGLNVL RIINEPTAAA IAYGLDRTGK GERNVLIFDL
GGGTFDVSIL TIDDGIFEVK ATAGDTHLGG EDFDNRLVNH
FVEEFKRKHK KDISQNKRAV RRLRTACERA KRTLSSSTQA
SLEIDSLFEG IDFYTSITRA RFEELCSDLF RSTLEPVEKA
LRDAKLDKAQ IHDLVLVGGS TRIPKVQKLL QDFFNGRDLN
KSINPDEAVA YGAAVQAAIL MGDKSENVQD LLLLDVAPLS
LGLETAGGVM TALIKRNSTI PTKQTQIFTT YSDNQPGVLI
QVYEGERAMT KDNNLLGRFE LSGIPPAPRG VPQIEVTFDI
DANGILNVTA TDKSTGKANK ITITNDKGRL SKEEIERMVQ
EAEKYKAEDE VQRERVSAKN ALESYAFNMK SAVEDEGLKG
KISEADKKKV LDKCQEVISW LDANTLAEKD EFEHKRKELE
QVCNPIISGL YQGAGGPGPG GFGAQGPKGG SGSGPTIEEV
D
```

Sequence Listings in addition to Table I

SEQ ID NO: 192
HSP-90 alpha (human):
PEETQTQDQP MEEEEVETFA FQAEIAQLMS LIINTFYSNK
EIFLRELISN SSDALDKIRY ESLTDPSKLD SGKELHINLI
PNKQDRTLTI VDTGIGMTKA DLINNLGTIA KSGTKAFMEA
LQAGADISMI GQFGVGFYSA YLVAEKVTVI TKHNDDEQYA
WESSAGGSFT VRTDTGEPMG RGTKVILHLK EDQTEYLEER
RIKEIVKKHS QFIGYPITLF VEKERDKEVS DDEAEEKEDK
EEEKEKEEKE SEDKPEIEDV GSDEEEEKKD GDKKKKKKIK
EKYIDQEELN KTKPIWTRNP DDITNEEYGE FYKSLTNDWE
DHLAVKHFSV EGQLEFRALL FVPRRAPFDL FENRKKKNNI
KLYVRRVFIM DNCEELIPEY LNFIRGVVDS EDLPLNISRE
MLQQSKILKV IRKNLVKKCL ELFTELAEDK ENYKKFYEQF
SKNIKLGIHE DSQNRKKLSE LLRYYTSASG DEMVSLKDYC
TRMKENQKHI YYITGETKDQ VANSAFVERL RKHGLEVIYM
IEPIDEYCVQ QLKEFEGKTL SVSVTKEGLEL PEDEEEKKKQ
EEKKTKFENL CKIMKDILEK KVEKVVVSNR LVTSPCCIVT
STYGWTANME RIMKAQALRD NSTMGYMAAK KHLEINPDHS
IIETLRQKAE ADKNDKSVKD LVILLYETAL LSSGFSLEDP
QTHANRIYRM IKLGLGIDED DPTADDTSAA VTEEMPPLEG
DDDTSRMEEV D SEQ ID NO: 193
HSP-90 beta (human):
PEEVHHGEEE VETFAFQAEI AQLMSLIINT FYSNKEIFLR
ELISNASDAL DKIRYESLTD PSKLDSGKEL KIDIIPNPQE
RTLTLVDTGI GMTKADLINN LGTIAKSGTK AFMEALQAGA
DISMIGQFGV GFYSAYLVAE KVVVITKHND DEQYAWESSA
GGSFTVRADH GEPIGRGTKV ILHLKEDQTE YLEERRVKEV
VKKHSQFIGY PITLYLEKER EKEISDDEAE EEKGEKEEED
KDDEEKPKIE DVGSDEEDDS GKDKKKKTKK IKEKYIDQEE
LNKTKPIWTR NPDDITQEEY GEFYKSLTND WEDHLAVKHF
SVEGQLEFRA LLFIPRRAPF DLFENKKKKN NIKLYVRRVF
IMDSCDELIP EYLNFIRGVV DSEDLPLNIS REMLQQSKIL
KVIRKNIVKK CLELFSELAE DKENYKKFYE AFSKNLKLGI
HEDSTNRRRL SELLRYHTSQ SGDEMTSLSE YVSRMKETQK
SIYYITGESK EQVANSAFVE RVRKRGFEVV YMTEPIDEYC
VQQLKEFDGK SLVSVTKEGL ELPEDEEEKK KMEESKAKFE
NLCKLMKEIL DKKVEKVTIS NRLVSSPCCI VTSTYGWTAN
MERIMKAQAL RDNSTMGYMM AKKHLEINPD HPIVETLRQK
AEADKNDKAV KDLVVLLFET ALLSSGFSLE DPQTHSNRIY
RMIKLGLGID EDEVAAEEPN AAVPDEIPPL EGDEDASRME
EVD SEQ ID NO: 194
GAD65 (human)
MASPGSGFWS FGSEDGSGDS ENPGTARAWC QVAQKFTGGI
GNKLCALLYG DAEKPAESGG SQPPRAAARK AACACDQKPC
SCSKVDVNYA FLHATDLLPA CDGERPTLAF LQDVMNILLQ
YVVKSFDRST KVIDFHYPNE LLQEYNWELA DQPQNLEEIL
MHCQTTLKYA IKTGHPRYFN QLSTGLDMVG LAADWLTSTA
NTNMFTYEIA PVFVLLEYVT LKKMRETTGW PGGSGDGIFS
PGGAISNMYA MMIARFKMFP EVKEKGMAAL PRLIAFTSEH
SHFSLKKGAA ALGIGTDSVI LIKCDERGKM IPSDLERRIL
EAKQKGFVPF LVSATAGTTV YGAFDPLLAV ADICKKYKIW
MHVDAAWGGG LLMSRKHKWK LSGVERANSV TWNPHKMMGV
PLQCSALLVR EEGLMQNCNQ MHASYLFQQD KHYDLSYDTG
DKALQCGRHV DVFKLWLMWR AKGTTGFEAH VDKCLELAEY
LYNIIKNREG YEMVFDGKPQ HTNVCFWYIP PSLRTLEDNE
ERMSRLSKVA PVIKARNMEY GTTMVSYQPL GDKVNFFRMV
ISNPAATHQD IDELIEEIER LGQDL SEQ ID NO: 195
Ro60 (human)
MEESVNQMQP LNEKQIANSQ DGYVWQVTDM NRLHRFLCFG
SEGGTYYIKE QKLGLENAEA LIRLIEDGRG CEVIQEIKSF
SQEGRTTKQE PMLFALAICS QCSDISTKQA AFKAVSEVCR
IPTHLFTFIQ FKKDLKESMK CGMWGRALRK AIADWYNEKG
GMALALAVTK YKQRNGWSHK DLLRLSHLKP SSEGLAIVTK
YITKGWKEVH ELYKEKALSV ETEKLLLKYL AVEKVKRTRD
ELEVIHLIEE HRLVREHLLT NHLKSKEVWK ALLQEMPLTA
LLRNLGKMTA NSVLEPGNSE VSLVCEKLCN EKLLKKARIH
PFHILTALET YKTGHGLRGK LKWRPDEEIL KALDAAFYKT
FKTVEPTGKR FLLAVDVSAS MNQRVLGSIL NASTVAAAMC
MVVTRTEKDS YVVAFSDEMV PCPVTDMTL QQVLMAMSQI PAGGTDCSLP MIWAQKTNTP ADVFIVFTDN ETFAGGVHPA
IALREYRKKM DIPAKLIVCG MTSNGFTIAD PDDRALQNTL
LNKSF SEQ ID NO: 196
HLA DQ2 ALPHA CHAIN
VADHVASYGV NLYQSYGPSG QYTHEFDGDE QFYVDLGRKE
TVWCLPELRQ FRGFDPQFAL TNIAVLKHNL NSLIKRSNST
AATNEVPEVT VFSKSPVTLG QPNTLICLVD NIFPPVVNIT
WLTNGHSVTE GVSETTFLSK SDHSFFKISY LTLLPSAEES
YDCKVEHWGL DKPLLKHWEP E SEQ ID NO: 197
HLA DQ2 BETA CHAIN
SPEDFVYQFK GMCYFTNGTE RVRLVSRSIY NREEIVRFDS
DVGEFRAVTL LGLPAAEYWN SQKDILERKR AAVDRVCRHN
YQLELRTTLQ RRVEPTVTIS PSRTEALNHH NLLVCSVTDF
YPAQIKVRWF RKDQEETAGV VSTPLIRNGD WTFQILVMLE
MTPQRGDVYT CHVEHPSLQS PITVEWRAQS SEQ ID NO: 198
HLA DQ7 ALPHA CHAIN
VADHVASYGV NLYQSYGPSG QYTHEFDGDE QFYVDLGRKE
TVWCLPELRQ FRGFDPQFAL TNIAVLKHNL NSLIKRSNST
AATNEVPEVT VFSKSPVTLG QPNTLICLVD NIFPPVVNIT
WLTNGHSVTE GVSETTFLSK SDHSFFKISY LTLLPSAEES
YDCKVEHWGL DKPLLKHWEP E SEQ ID NO: 199
HLA DQ7 BETA CHAIN
SPEDFVYQFK AMCYFTNGTE RVYVTRYIYN REEYARFDSD
VEVYRAVTPL GPPDAEYWNS QKEVLERTRA ELDTVCRHNY
QLELRTTLQR RVEPTVTISP SRTEALNHHN LLVCSVTDFY
PAQIKVRWFR NDQEETTGVV STPLIRNGDW TFQILVMLEM
TPQHGDVYTC HVEHPSLQNP ITVEWRAQS SEQ ID NO: 200
HLA DQ8 ALPHA CHAIN
VADHVASYGV NLYQSYGPSG QYSHEFDGDE EFYVDLERKE
TVWQLPLFRR FRRFDPQFAL TNIAVLKHNL NIVIKRSNST
AATNEVPEVT VFSKSPVTLG QPNTLICLVD NIFPPVVNIT
WLSNGHSVTE GVSETSFLSK SDHSFFKISY LTFLPSDDEI
YDCKVEHWGL DEPLLKHWEP E SEQ ID NO: 201
HLA DQ8 BETA CHAIN
SPEDFVYQFK GMCYFTNGTE RVRLVTRYIY NREEYARFDS
DVGVYRAVTP LGPPAAEYWN SQKEVLERTR AELDTVCRHN
YQLELRTTLQ RRVEPTVTIS PSRTEALNHH NLLVCSVTDF
YPAQIKVRWF RNDQEETTAG VVSTPLIRNG DWTFQILVML
EMTPQRGDVY TCHVEHPSLQ NPIIVEWRAQ S SEQ ID NO: 202
Human myelin oligodendrocyte glycoprotein (MOG)
QFRVIGPRHP IRALVGDEVE LPCRISPGKN ATGMEVGWYR
PPFSRVVHLY RNGKDQDGDQ APEYRGRTEL LKDAIGEGKV
TLRIRNVRFS DEGGFTCFFR DHSYQEEAAM ELKVEDPFYW
VSPGVLVLLA VLPVLLLQIT VGLVFLCLQY RLRGKLRAEI
ENLHRTFGQF LEELRNPF SEQ ID NO: 203
Human Myelin-associated oligodendrocyte basic
protein
MSQKPAKEGP RLSKNQKYSE HFSIHCCPPF TFLNSKKEIV
DRKYSICKSG CFYQKKEEDW ICCACQKTRL KRKIRPTPKK
K SEQ ID NO: 204
HUMAN DESMOGLEIN 3 PREPROPROTEIN
MMGLFPRTTG ALAIFVVVIL VHGELRIETK GQYDEEEMTM
QQAKRRQKRE WVKFAKPCRE GEDNSKRNPI AKITSDYQAT
QKITYRISGV GIDQPPFGIF VVDKNTGDIN ITAIVDREET
PSFLITCRAL NAQGLDVEKP LILTVKILDI NDNPPVFSQQ
IFMGEIEENS ASNSLVMILN ATDADEPNHL NSKIAFKIVS
QEPAGTPMFL LSRNTGEVRT LTNSLDREQA SSYRLVVSGA
DKDGEGLSTQ CECNIKVKDV NDNFPMFRDS QYSARIEENI
LSSELLRFQV TDLDEEYTDN WLAVYFFTSG NEGNWFEIQT
DPRTNEGILK VVKALDYEQL QSVKLSIAVK NKAEFHQSVI

Sequence Listings in addition to Table I

```
SRYRVQSTPV TIQVINVREG IAFRPASKTF TVQKGISSKK
LVDYILGTYQ AIDEDTNKAA SNVKYVMGRN DGGYLMIDSK
TAEIKFVKNM NRDSTFIVNK TITAEVLAID EYTGKTSTGT
VYVRVPDFND NCPTAVLEKD AVCSSSPSVV VSARTLNNRY
TGPYTFALED QPVKLPAVWS ITTLNATSAL LRAQEQIPPG
VYHISLVLTD SQNNRCEMPR SLTLEVCQCD NRGICGTSYP
TTSPGTRYGR PHSGRLGPAA IGLLLLGLLL LLLAPLLLLT
CDCGAGSTGG VTGGFIPVPD GSEGTIHQWG IEGAHPEDKE
ITNICVPPVT ANGADFMESS EVCTNTYARG TAVEGTSGME
```

Sequence Listings in addition to Table I

```
MTTKLGAATE SGGAAGFATG TVSGAASGFG AATGVGICSS
GQSGTMRTRH STGGTNKDYA DGAISMNFLD SYFSQKAFAC
AEEDDGQEAN DCLLIYDNEG ADATGSPVGS VGCCSFIADD
LDDSFLDSLG PKFKKLAEIS LGVDGEGKEV QPPSKDSGYG
IESCGHPIEV QQTGFVKCQT LSGSQGASAL STSGSVQPAV
SIPDPLQHGN YLVTETYSAS GSLVQPSTAG FDPLLTQNVI
VTERVICPIS SVPGNLAGPT QLRGSHTMLC TEDPCSRLI
```

What is claimed is:

1. A process for manufacturing a composition comprising directed sequence polymers (DSPs), comprising the steps of:
   (1) selecting a first base peptide sequence, wherein the sequence is an amino acid sequence of an epitope of an antigen associated with an autoimmune disease;
   (2) synthesizing by solid phase peptide synthesis a first cassette of the DSPs, each cassette having a sequence of amino acid positions corresponding to each amino acid of the base peptide sequence,
      wherein, for at least one amino acid position of the first cassette of the directed sequence polymers, an amino acid is added, said amino acid randomly selected from a mixture of amino acids comprising the original amino acid found at that amino acid position, alanine (A), and, optionally, at least one conserved substitution,
         wherein the amino acids in the mixture are present in a fixed molar input ratio relative to each other, determined prior to starting synthesis,
         wherein the relative molar amount of A is more than 10% and less than 90% of the total amino acid concentration of the DSPs;
   (3) optionally extending the length of the DSPs by at least one of
      (a) repeating step (2) for 2 to 15 cycles and elongating the DSP under the same condition; or
      (b) repeating step (2) for 2 to 15 cycles and elongating the DSP, for each cycle, using a different input ratio of amino acids in the mixture; or
      (c) repeating steps (1) and (2) for 2 to 15 cycles and elongating the DSP using cassettes based on more than one base peptide; or
      (d) assembling 2 to 15 cassettes synthesized in a single cycle of step (2); or
      (e) assembling 2 to 15 cassettes, the first cassette synthesized under one condition of step (2), and second and more cassettes synthesized under other conditions of step (2);
   (4) optionally further elongating the DSPs by repeating steps (2) and (3) for 2 to 15 cycles, wherein for each cycle a new cassette of the DSP is designed independently from any of the previous cassettes designated by previous cycles of step (2);
   wherein the number of cycles selected in steps (3) and (4) is selected so that the final length of the DSP is about 25 to 300 amino acid residues.

2. The process according to claim 1, wherein the amino acid sequence of the epitope is selected from SEQ ID NOS: 1 through 189 depicted in Table I.

3. The process according to claim 1, wherein the autoimmune disease is selected from multiple sclerosis, systemic lupus erythematosus, type I diabetes mellitus, myasthenia gravis, rheumatoid arthritis, and pemphigus vulgaris.

4. The process according to claim 3, wherein the autoimmune disease is multiple sclerosis.

5. The process according to claim 3, wherein the autoimmune disease is systemic lupus erythematosus.

6. The process according to claim 3, wherein the autoimmune disease is type I diabetes mellitus.

7. The process according to claim 3, wherein the autoimmune disease is myasthenia gravis.

8. The process according to claim 3, wherein the autoimmune disease is rheumatoid arthritis.

9. The process according to claim 3, wherein the autoimmune disease is pemphigus vulgaris.

10. The process according to claim 4, wherein the amino acid sequence of the epitope is a partial sequence of a protein selected from osteopontin, an HLA protein, myelin oligodendrite glycoprotein, myelin basic protein (MBP), proteolipid protein, and myelin associated glycoproteins, S100Beta, heat shock protein alpha, beta crystallin, myelin-associated oligodendrocytic basic protein (MOBP), and 2',3' cyclic nucleotide 3'-phosphodiesterase.

11. The process according to claim 4, wherein the amino acid sequence of the epitope is selected from SEQ ID NOS: 6-32.

12. The process according to claim 5, wherein the amino acid sequence of the epitope is a partial sequence of a protein selected from hsp60, hsp70, Ro60, La, SmD, and 70-kDa U1RNP.

13. The process according to claim 5, wherein the amino acid sequence of the epitope is selected from SEQ ID NOS: 92-140.

14. The process according to claim 6, wherein the amino acid sequence of the epitope is a partial sequence of a protein selected from hsp60, glutamic acid decarboxylase (GAD65), insulinoma-antigen 2 (IA-2), and insulin.

15. The process according to claim 6, wherein the amino acid sequence of the amino acid sequence of the epitope is selected from SEQ ID NOS: 44-91.

16. The process according to claim 7, wherein the amino acid sequence of the epitope is a partial sequence of a protein selected from acetylcholine receptor (AChR) α-subunit and muscle-specific receptor tyrosine kinase (MuSK).

17. The process according to claim 7, wherein the amino acid sequence of the epitope is selected from SEQ ID NOS: 1-2.

18. The process according to claim 8, wherein the amino acid sequence of the epitope is a partial sequence of a protein selected from type II collagen and hsp60.

19. The process according to claim 8, wherein the amino acid sequence of the epitope is selected from SEQ ID NOS: 3-5.

20. The process according to claim 9, wherein the amino acid sequence of the epitope is a partial sequence of a protein selected from desmoglein 3 (Dsg3).

21. The process according to claim 9, wherein the amino acid sequence of the epitope is selected from SEQ ID NOS: 33-43.

22. The process according to claim 1, wherein the amino acid similarity is defined according to the similarity table shown in FIG. 4.

23. The process of claim 1, wherein the conserved substitution is the most prevalent conserved substitution or a replacement defined according to amino acid similarity.

24. A process for manufacturing a composition comprising directed sequence polymers (DSPs), comprising the steps of:
   (1) selecting a first base peptide sequence, wherein the sequence is an amino acid sequence of an epitope of an antigen associated with an autoimmune disease;
   (2) synthesizing by solid phase peptide synthesis a first cassette of the DSPs, each cassette having a sequence of amino acid positions corresponding to each amino acid of the base peptide sequence,
      wherein, for each amino acid position of the first cassette of the directed sequence polymers, an amino acid is added, said amino acid randomly selected from a mixture of amino acids comprising the original amino acid found at that amino acid position, alanine (A), and, optionally, at least one conserved substitution,
         wherein the amino acids in the mixture are present in a fixed molar input ratio relative to each other, determined prior to starting synthesis, wherein the relative molar amount of A is more than 10% and less than 90% of the total amino acid concentration of the DSPs;
(3) optionally extending the length of the DSPs by at least one of:
  (a) repeating step (2) for 2 to 15 cycles and elongating the DSP under the same condition; or
  (b) repeating step (2) for 2 to 15 cycles and elongating the DSP, for each cycle, using a different input ratio of amino acids in the mixture; or
  (c) repeating steps (1) and (2) for 2 to 15 cycles and elongating the DSP using cassettes based on more than one base peptide; or
  (d) assembling 2 to 15 cassettes synthesized in a single cycle of step (2); or
  (e) assembling 2 to 15 cassettes, the first cassette synthesized under one condition of step (2), and second and more cassettes synthesized under other conditions of step (2);
(4) optionally further elongating the DSPs by repeating steps (2) and (3) for 2 to 15 cycles, wherein for each cycle a new cassette of the DSP is designed independently from any of the previous cassettes designated by previous cycles of step (2);
wherein the number of cycles selected in steps (3) and (4) is selected so that the final length of the DSP is about 25 to 300 amino acid residues.

* * * * *

SEQUENCE LISTING

```
<160> NUMBER OF SEQ ID NOS: 240

<210> SEQ ID NO 1
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Ser Tyr Cys Glu Ile Ile Val Thr His Phe Pro Phe Asp Glu Gln
1               5                   10                  15

Asn Cys Ser Met Lys Leu Gly Thr Trp Thr Tyr Asp Gly Ser Val Val
            20                  25                  30

Ala Thr Asn Pro Glu Ser Asp
        35

<210> SEQ ID NO 2
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Met Lys Ser Asp Gln Glu Ser Asn Asn Ala Ala Ala Glu Trp Lys Tyr
1               5                   10                  15

Val Ala Met Val Met Asp His Ile Leu Leu
            20                  25

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Phe Lys Gly Glu Gln Gly Pro Lys
1               5

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 4

Pro Lys Gly Gln Thr Gly Glu Asx Gly Ile Ala Gly Phe Lys Gly Glu
1               5                   10                  15

Gln Gly Pro Lys
            20

<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Glu Asx Gly Ile Ala Gly Phe Lys Gly Glu Gln Gly Pro Lys Gly
1               5                   10                  15

Glu Asx Gly Pro Ala
            20

<210> SEQ ID NO 6
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Glu Val Gly Glu Leu Ser Arg Gly Lys Leu Tyr Ser Leu Gly Asn Gly
1               5                   10                  15

Arg Trp Met Leu Thr Leu Ala Lys Asn Met Glu Val Arg Ala Ile
            20                  25                  30

<210> SEQ ID NO 7
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Asn Gly Arg Trp Met Leu Thr Leu Ala Lys Asn Met Glu Val Arg
1               5                   10                  15

Ala Ile Phe Thr Gly Tyr Tyr Gly Lys Gly Lys Pro Val Pro Thr Gln
            20                  25                  30

Gly

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Ser Gln Lys Arg Pro Ser Gln Arg His
1               5                   10

<210> SEQ ID NO 9
<211> LENGTH: 19
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 9

Leu Ser Arg Phe Ser Trp Gly Ala Glu Gly Gln Arg Pro Gly Phe Gly
1               5                   10                  15

Tyr Gly Gly

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Ser Asp Tyr Lys Ser Ala His Lys Gly Phe Lys Gly Val Asp
1               5                   10                  15

<210> SEQ ID NO 11
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Ser Asp Tyr Lys Ser Ala His Lys Gly Leu Lys Gly Val Asp Ala
1               5                   10                  15

Gln Gly Thr Leu Ser Lys Ile Phe Lys
            20                  25

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Tyr Leu Ala Thr Ala Ser Thr Met Asp His Ala Arg His Gly Phe
1               5                   10                  15

Leu Pro Arg His
            20

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Gly Phe Lys Gly Val Asp Ala Gln Gly Thr Leu Ser Lys Ile
1               5                   10                  15

<210> SEQ ID NO 14
<211> LENGTH: 25
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 14

Ala Gln Gly Thr Leu Ser Lys Ile Phe Lys Leu Gly Gly Arg Asp Ser
1               5                   10                  15

Arg Ser Gly Ser Pro Met Ala Arg Arg
            20                  25

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Thr Leu Ser Lys Ile Phe Lys Leu Gly Gly Arg Asp Ser Arg
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser His Gly Arg Thr Gln Asp Glu Asn Pro Val Val His Phe Phe Lys
1               5                   10                  15

<210> SEQ ID NO 17
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Tyr Gly Arg Thr Gln Asp Glu Asn Pro Val Val His Phe Phe Lys Asn
1               5                   10                  15

Ile Val Thr Pro Arg Thr Pro Pro Pro
            20                  25

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu Asn Pro Val Val His Phe Phe Lys Asn Ile Val Thr Pro Arg Thr
1               5                   10                  15

Pro

<210> SEQ ID NO 19
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 19

Asp Glu Asn Pro Val Val His Phe Phe Lys Asn Ile Val Thr Pro Arg
1               5                   10                  15

Thr Pro Pro

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Glu Asn Pro Val Val His Phe Phe Lys Asn Ile Val Thr Pro Arg
1               5                   10                  15

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Val Val His Phe Phe Lys Asn Ile Val Thr Pro Arg Thr Pro Pro
1               5                   10                  15

Ser Gln Gly Lys
            20

<210> SEQ ID NO 22
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Phe Ser Ile His Cys Cys Pro Pro Phe Thr Phe Asn Asn Ser Lys Lys
1               5                   10                  15

Glu Ile Val

<210> SEQ ID NO 23
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Phe Leu Asn Ser Lys Lys Glu Ile Val Asp Arg Lys Tyr Ser Ile Cys
1               5                   10                  15

Lys Ser Gly

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24
```

```
Cys Gln Phe Arg Val Ile Gly Pro Arg His Pro Ile Arg Ala Leu Val
1               5                   10                  15

Gly Asp Glu Val
            20

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Pro Ile Arg Ala Leu Val Gly Asp Glu Val Glu Leu Pro Cys Arg Ile
1               5                   10                  15

Ser Pro Gly Lys
            20

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Glu Leu Pro Cys Arg Ile Ser Pro Gly Lys Asn Ala Thr Gly Met Glu
1               5                   10                  15

Val Gly Trp Tyr
            20

<210> SEQ ID NO 27
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Met Glu Val Gly Trp Tyr Arg Pro Pro Phe Ser Arg Val Val His Leu
1               5                   10                  15

Tyr Arg Asn Gly Lys
            20

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

His Ser Leu Gly Lys Trp Leu Gly His Pro Asp Lys Phe
1               5                   10

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 29

His Cys Leu Gly Lys Trp Leu Gly His Pro Asp Lys Phe Val Gly Ile
1               5                   10                  15

<210> SEQ ID NO 30
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asn Thr Trp Thr Thr Cys Gln Ser Ile Ala Phe Pro Ser Lys Thr Ser
1               5                   10                  15

Ala Ser Ile Gly
            20

<210> SEQ ID NO 31
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Lys Thr Ser Ala Ser Ile Gly Ser Leu Cys Ala Asp Ala Arg Met
1               5                   10                  15

Tyr Gly Val Leu
            20

<210> SEQ ID NO 32
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Phe Tyr Thr Thr Gly Ala Val Arg Gln Ile Phe Gly Asp Tyr Lys
1               5                   10                  15

Thr Thr

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Glu Trp Val Lys Phe Ala Lys Pro Cys Arg Glu
1               5                   10

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Ala Thr Gln Lys Ile Thr Tyr Arg Ile Ser Gly Val Gly Ile Asp
1               5                   10                  15

Gln

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Pro Phe Gly Ile Phe Val Val Asp Lys Asn Thr Gly Asp Ile Asn Ile
1               5                   10                  15

Thr

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

His Leu Asn Ser Lys Ile Ala Phe Lys Ile Val Ser Gln Glu Pro Ala
1               5                   10                  15

Gly

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Thr Pro Met Phe Leu Leu Ser Arg Asn Thr Gly Glu Val Arg Thr
1               5                   10                  15

Leu

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Cys Glu Cys Asn Ile Lys Val Lys Asp Val Asn Asp Asn Phe Pro
1               5                   10                  15

Met

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
Ser Val Lys Leu Ser Ile Ala Val Lys Asn Lys Ala Glu Phe His Gln
1               5                   10                  15

Ser

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asn Val Arg Glu Gly Ile Ala Phe Arg Pro Ala Ser Lys Thr Phe Thr
1               5                   10                  15

Val

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Asp Ser Thr Phe Ile Val Asn Lys Thr Ile Thr Ala Glu Val Leu
1               5                   10                  15

Ala

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Ala Arg Thr Leu Asn Asn Arg Tyr Thr Gly Pro Tyr Thr Phe
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Ser Gly Thr Met Arg Thr Arg His Ser Thr Gly Gly Thr Asn
1               5                   10                  15

<210> SEQ ID NO 44
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ala Ala Leu Gly Ile Gly Thr Asp Ser Val Ile Leu Ile Lys Cys Asp
1               5                   10                  15
```

```
Glu Arg Gly Lys
            20

<210> SEQ ID NO 45
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Phe Thr Ser Glu His Ser His Phe Ser Leu Lys Lys Gly Ala Ala
1               5                  10                  15

Ala Leu Gly Ile
            20

<210> SEQ ID NO 46
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Thr His Gln Asp Ile Asp Phe Leu Ile Glu Glu Ile Glu Arg Leu
1               5                  10                  15

Gly Gln Asp Leu
            20

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Val Arg Pro Leu Trp Val Arg Met Glu
1               5                  10

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Tyr Val Arg Pro Leu Trp Val Arg Met Glu
1               5                  10

<210> SEQ ID NO 49
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Cys Gly Arg His Val Asp Val Phe Lys Leu Trp Leu Met Trp Arg Ala
1               5                  10                  15

Lys Gly Thr Thr Gly
```

-continued

```
                    20

<210> SEQ ID NO 50
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Asp Glu Arg Gly Lys Met Ile Pro Ser Asp Leu Glu Arg Arg Ile Leu
1               5                   10                  15

Glu Ala Lys Gln
            20

<210> SEQ ID NO 51
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asp Ile Cys Lys Lys Tyr Lys Ile Trp Met His Val Asp Ala Ala Trp
1               5                   10                  15

Gly Gly Gly Leu Leu Met Ser
            20

<210> SEQ ID NO 52
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Met Val Gly Leu Ala Ala Asp Trp Leu Thr Ser Thr Ala Asn Thr
1               5                   10                  15

Asn Met Phe Thr
            20

<210> SEQ ID NO 53
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Glu Glu Ile Leu Met His Cys Gln Thr Thr Leu Lys Tyr Ala Ile Lys
1               5                   10                  15

Thr Gly His Pro
            20

<210> SEQ ID NO 54
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54
```

```
Glu Leu Leu Gln Glu Tyr Asn Trp Glu Leu Ala Asp Gln Pro Gln Asn
1               5                   10                  15

Leu Glu Glu Ile Leu Met
            20
```

<210> SEQ ID NO 55
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

```
Glu Arg Ala Asn Ser Val Thr Trp Asn Pro His Lys Met Met Gly Val
1               5                   10                  15

Pro Leu Gln Cys
            20
```

<210> SEQ ID NO 56
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

```
Glu Tyr Gly Thr Thr Met Val Ser Tyr Gln Pro Leu Gly Asp Lys Val
1               5                   10                  15

Asn Phe Phe Arg
            20
```

<210> SEQ ID NO 57
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

```
Glu Tyr Leu Tyr Asn Ile Ile Lys Asn Arg Glu Gly Tyr Glu Met Val
1               5                   10                  15

Phe Asp Gly Lys
            20
```

<210> SEQ ID NO 58
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

```
Glu Tyr Val Thr Leu Lys Lys Met Arg Glu Ile Ile Gly Trp Pro Gly
1               5                   10                  15

Gly Ser Gly Asp
            20
```

<210> SEQ ID NO 59
<211> LENGTH: 20
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 59

Gly Gly Ser Gly Asp Gly Ile Phe Ser Pro Gly Gly Ala Ile Ser Asn
1               5                   10                  15

Met Tyr Ala Met
            20

<210> SEQ ID NO 60
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Leu Leu Met Ser Arg Lys His Lys Trp Lys Leu Ser Gly Val Glu
1               5                   10                  15

Arg Ala Asn Ser
            20

<210> SEQ ID NO 61
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Ser Gly Asp Ser Glu Asn Pro Gly Thr Ala Arg Ala Trp Cys Gln
1               5                   10                  15

Val Ala Gln Lys Phe Thr Gly
            20

<210> SEQ ID NO 62
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

His Ala Thr Asp Leu Leu Pro Ala Cys Asp Gly Glu Arg Pro Thr Leu
1               5                   10                  15

Ala Phe Leu Gln
            20

<210> SEQ ID NO 63
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ile Pro Pro Ser Leu Arg Thr Leu Glu Asp Asn Glu Glu Arg Met Ser
1               5                   10                  15

Arg Leu Ser Lys
            20
```

```
<210> SEQ ID NO 64
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Lys Gly Thr Thr Gly Phe Glu Ala His Val Asp Lys Cys Leu Glu Leu
1               5                   10                  15

Ala Glu Tyr Leu Tyr Asn
            20

<210> SEQ ID NO 65
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Lys His Tyr Asp Leu Ser Tyr Asp Thr Gly Asp Lys Ala Leu Gln Cys
1               5                   10                  15

Gly Arg His Val
            20

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Lys Pro Cys Ser Cys Ser Lys Val Asp Val Asn Tyr Ala Phe Leu His
1               5                   10                  15

Ala Thr Asp Leu
            20

<210> SEQ ID NO 67
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Lys Thr Gly His Pro Arg Tyr Phe Asn Gln Leu Ser Thr Gly Leu Asp
1               5                   10                  15

Met Val Gly Leu
            20

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Val Ala Pro Val Ile Lys Ala Arg Met Met Glu
```

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Lys Val Ala Pro Val Trp Val Ala Arg Met Met Glu
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Lys Val Ala Pro Val Trp Val Arg Met Glu
1               5                   10

<210> SEQ ID NO 71
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Leu Ala Phe Leu Gln Asp Val Met Asn Ile Leu Leu Gln Tyr Val Val
1               5                   10                  15

Lys Ser Phe Asp Arg Ser
            20

<210> SEQ ID NO 72
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Leu Glu Ala Lys Gln Lys Gly Phe Val Pro Phe Leu Val Ser Ala Thr
1               5                   10                  15

Ala Gly Thr Thr
            20

<210> SEQ ID NO 73
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Leu Leu Tyr Gly Asp Ala Glu Lys Pro Ala Glu Ser Gly Gly Ser Gln
1               5                   10                  15

Pro Pro Arg Ala
            20

<210> SEQ ID NO 74
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Leu Ser Lys Val Ala Pro Val Ile Lys Ala Arg Met Met Glu Tyr Gly
1               5                   10                  15

<210> SEQ ID NO 75
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Met Ala Ser Pro Gly Ser Gly Phe Trp Ser Phe Gly Ser Glu Asp Gly
1               5                   10                  15

Ser Gly Asp Ser
            20

<210> SEQ ID NO 76
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Asn Met Tyr Ala Met Met Ile Ala Arg Phe Lys Met Phe Pro Glu Val
1               5                   10                  15

Lys Glu Lys Gly
            20

<210> SEQ ID NO 77
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Pro Glu Val Lys Glu Lys Gly Met Ala Ala Leu Pro Arg Leu Ile Ala
1               5                   10                  15

Phe Thr Ser Glu
            20

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gln His Arg Pro Leu Trp Val Arg Met Glu
1               5                   10

```
<210> SEQ ID NO 79
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gln Lys Phe Thr Gly Gly Ile Gly Ile Gly Asn Lys Leu Cys Ala Leu
1               5                   10                  15

Leu Tyr Gly Asp
            20

<210> SEQ ID NO 80
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Asn Cys Asn Gln Met His Ala Ser Tyr Leu Phe Gln Gln Asp Lys
1               5                   10                  15

His Tyr Asp Leu
            20

<210> SEQ ID NO 81
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gln Pro Pro Arg Ala Ala Ala Arg Lys Ala Ala Cys Ala Cys Asp Gln
1               5                   10                  15

Lys Pro Cys Ser Cys
            20

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Thr Arg Pro Leu Trp Val Arg Met Glu
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Arg Val Leu Pro Leu Trp Val Arg Met Glu
1               5                   10
```

```
<210> SEQ ID NO 84
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ser Phe Asp Arg Ser Thr Lys Val Ile Asp Phe His Tyr Pro Asn Glu
1               5                   10                  15

Leu Leu Gln Glu
            20

<210> SEQ ID NO 85
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ser Arg Leu Ser Lys Val Ala Pro Val Ile Lys Ala Arg Met Met Glu
1               5                   10                  15

Tyr Gly Thr Thr
            20

<210> SEQ ID NO 86
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Thr Ala Gly Thr Thr Val Tyr Gly Ala Phe Asp Pro Leu Leu Ala Val
1               5                   10                  15

Ala Asp Ile Cys Lys Lys
            20

<210> SEQ ID NO 87
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Thr Asn Met Phe Thr Tyr Glu Ile Ala Pro Val Phe Val Leu Leu Glu
1               5                   10                  15

Tyr Val Thr Leu
            20

<210> SEQ ID NO 88
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Val Phe Asp Gly Lys Pro Gln His Thr Met Val Cys Lys Trp Tyr Ile
1               5                   10                  15
```

-continued

Pro Pro Ser Leu
            20

<210> SEQ ID NO 89
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Val Asn Phe Phe Arg Met Val Ile Ser Met Pro Ala Ala Thr His Gln
1               5                   10                  15

Asp Ile Asp Phe
            20

<210> SEQ ID NO 90
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Val Pro Leu Gln Cys Ser Ala Leu Leu Val Arg Glu Glu Gly Leu Met
1               5                   10                  15

Gln Asn Cys Asn Gln
            20

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Tyr Thr Leu Pro Leu Trp Val Arg Met Glu
1               5                   10

<210> SEQ ID NO 92
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Cys Ser Asp Ile Ser Thr Lys Gln Ala Ala Phe Lys Ala Val Ser
1               5                   10                  15

Glu Val Cys Arg Ile Pro Thr His Leu
            20                  25

<210> SEQ ID NO 93
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

```
Glu Thr Glu Lys Leu Leu Lys Tyr Leu Glu Ala Val Glu Lys Val Lys
1               5                   10                  15

Arg Thr Arg Asp Glu Leu Glu Val Ile
            20                  25

<210> SEQ ID NO 94
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Lys Ala Arg Ile His Pro Phe His Ile Leu Ile Ala Leu Glu Thr Tyr
1               5                   10                  15

Lys Thr Gly His
            20

<210> SEQ ID NO 95
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Phe Lys Thr Val Glu Pro Thr Gly Lys Arg Phe Leu Leu Ala Val Asp
1               5                   10                  15

Val Ser Ala Ser Met Asn Gln Arg Val
            20                  25

<210> SEQ ID NO 96
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Met Asn Gln Arg Val Leu Gly Ser Ile Leu Asn Ala Ser Thr Val Ala
1               5                   10                  15

Ala Ala Met Cys Ile Lys Ala Leu Asp Ala
            20                  25

<210> SEQ ID NO 97
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Pro Cys Pro Val Thr Thr Asp Met Thr Leu Gln Gln Val Leu Met Ala
1               5                   10                  15

Met Ser Gln Ile Pro Ala Gly Gly Thr
            20                  25

<210> SEQ ID NO 98
<211> LENGTH: 25
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 98

Pro Ala Gly Gly Thr Asp Cys Ser Leu Pro Met Ile Trp Ala Gln Lys
1               5                   10                  15

Thr Asn Thr Pro Ala Asp Val Phe Ile
            20                  25

<210> SEQ ID NO 99
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Lys Thr Asn Thr Pro Ala Asp Val Phe Ile Val Phe Thr Asp Asn Glu
1               5                   10                  15

Thr Phe Ala Gly
            20

<210> SEQ ID NO 100
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Met Ala Ala Leu Glu Ala Lys Ile Cys His Gln Ile Glu Tyr Tyr Phe
1               5                   10                  15

<210> SEQ ID NO 101
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Asp Glu Tyr Lys Asn Asp Val Lys Asn Arg Ser Val Tyr Ile Lys Gly
1               5                   10                  15

Phe Pro Thr Asp Ala Thr Leu Asp Asp Ile
            20                  25

<210> SEQ ID NO 102
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Arg Ser Val Tyr Ile Lys Gly Phe Pro Thr Asp Ala Thr Leu Asp Asp
1               5                   10                  15

<210> SEQ ID NO 103
<211> LENGTH: 16
<212> TYPE: PRT
<213> ORGANISM: Artificial Sequence
<220> FEATURE:
<223> OTHER INFORMATION: Description of Artificial Sequence: Synthetic

<400> SEQUENCE: 103

Thr Leu Asp Asp Ile Lys Glu Trp Leu Glu Asp Lys Gly Gln Val Leu
1               5                   10                  15

<210> SEQ ID NO 104
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Trp Leu Glu Asp Lys Gly Gln Val Leu Asn Ile Gln Met Arg Arg Thr
1               5                   10                  15

<210> SEQ ID NO 105
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Lys Gly Gln Val Leu Asn Ile Gln Met Arg Arg Thr Leu His Lys Ala
1               5                   10                  15

Phe Lys Gly Ser Ile Phe Val Val Phe Asp Ser Ile Glu Ser Ala Lys
            20                  25                  30

Lys Phe Val Glu
        35

<210> SEQ ID NO 106
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Met Arg Arg Thr Leu His Lys Ala Phe Lys Gly Ser Ile Phe Val Val
1               5                   10                  15

<210> SEQ ID NO 107
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ser Ile Phe Val Val Phe Asp Ser Ile Glu Ser Ala Lys Lys Phe Val
1               5                   10                  15

<210> SEQ ID NO 108
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Val Val Phe Asp Ser Ile Glu Ser Ala Lys Lys Phe Val Glu Thr Pro
1               5                   10                  15

<210> SEQ ID NO 109
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ser Ile Glu Ser Ala Lys Lys Phe Val Glu Thr Pro Gly Gln Lys Tyr
1               5                   10                  15

<210> SEQ ID NO 110
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Thr Asp Leu Leu Ile Leu Phe Lys Asp Asp Tyr Phe Ala Lys Lys Asn
1               5                   10                  15
Glu

<210> SEQ ID NO 111
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Ile Leu Phe Lys Asp Asp Tyr Phe Ala Lys Lys Asn Glu Glu Arg Lys
1               5                   10                  15

<210> SEQ ID NO 112
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Cys His Gln Ile Glu Tyr Tyr Phe Gly Asp Phe Asn Leu Pro Arg Asp
1               5                   10                  15
Lys Phe Leu Lys
            20

<210> SEQ ID NO 113
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Glu Glu Asp Ala Glu Met Lys Ser Leu Glu Lys Ile Gly Cys Leu
1               5                   10                  15

<210> SEQ ID NO 114

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Leu Glu Glu Lys Ile Gly Cys Leu Leu Lys Phe Ser Gly Asp Leu Asp
1               5                   10                  15

<210> SEQ ID NO 115
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Tyr Tyr Phe Gly Asp Phe Asn Leu Pro Arg Asp Lys Phe Leu Lys Glu
1               5                   10                  15

<210> SEQ ID NO 116
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ser Asn His Gly Glu Ile Lys Trp Ile Asp Phe Val Arg Gly Ala Lys
1               5                   10                  15

<210> SEQ ID NO 117
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gly Glu Ile Lys Trp Ile Asp Phe Val Arg Gly Ala Lys Glu Gly Ile
1               5                   10                  15

<210> SEQ ID NO 118
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ala Leu Lys Gly Lys Ala Lys Asp Ala Asn Asn Gly Leu Asn Gln Leu
1               5                   10                  15

Arg

<210> SEQ ID NO 119
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119
```

```
Phe Asn Leu Pro Arg Asp Lys Phe Leu Lys Glu Gln Ile Lys Leu Asp
1               5                   10                  15
```

<210> SEQ ID NO 120
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

```
Ala Lys Asp Ala Asn Asn Gly Asn Leu Gln Leu Arg Asn Lys Glu Val
1               5                   10                  15
```

<210> SEQ ID NO 121
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

```
Leu Gln Leu Arg Asn Lys Glu Val Thr Trp Glu Leu Val Glu Gly Glu
1               5                   10                  15
```

<210> SEQ ID NO 122
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

```
Asn Lys Glu Val Thr Trp Glu Leu Val Glu Gly Glu Val Glu Lys Glu
1               5                   10                  15
```

<210> SEQ ID NO 123
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

```
Glu Gly Glu Val Glu Lys Glu Ala Leu Lys Lys Ile Ile Glu Asp Gln
1               5                   10                  15
```

<210> SEQ ID NO 124
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

```
Glu Lys Glu Ala Leu Lys Lys Ile Ile Glu Asp Gln Gln Glu Ser Leu
1               5                   10                  15
```

<210> SEQ ID NO 125
<211> LENGTH: 16
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 125

Arg Asp Lys Phe Leu Lys Glu Gln Ile Lys Leu Asp Glu Gly Trp Val
1               5                   10                  15

<210> SEQ ID NO 126
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Lys Gly Lys Gly Asn Lys Ala Ala Gln Pro Gly Ser Gly Lys Gly
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gly Ser Lys Gly Lys Gly Lys Val Gln Phe Gln Gly Lys Lys Thr Lys
1               5                   10                  15

<210> SEQ ID NO 128
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Phe Gln Gly Lys Lys Thr Lys Phe Ala Ser Asp Asp Glu His Asp Glu
1               5                   10                  15

<210> SEQ ID NO 129
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Asp Glu Asn Gly Ala Thr Gly Pro Val Lys Arg Ala Arg Glu Glu Thr
1               5                   10                  15

<210> SEQ ID NO 130
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Glu Glu Thr Asp Lys Glu Glu Pro Ala Ser Lys Gln Gln Lys Thr Glu
1               5                   10                  15

<210> SEQ ID NO 131
```

```
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gly Trp Val Pro Leu Glu Ile Met Ile Lys Phe Asn Arg Leu Asn Arg
1               5                   10                  15

Leu Thr Thr Asp Phe Asn Val
            20

<210> SEQ ID NO 132
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Pro Leu Glu Ile Met Ile Lys Phe Asn Arg Leu Asn Arg Leu Thr Thr
1               5                   10                  15

<210> SEQ ID NO 133
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ile Met Ile Lys Phe Asn Arg Leu Asn Arg Leu Thr Thr Asp Phe Asn
1               5                   10                  15

<210> SEQ ID NO 134
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Lys Phe Asn Arg Leu Asn Arg Leu Thr Thr Asp Phe Asn Val Ile Val
1               5                   10                  15

<210> SEQ ID NO 135
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Asp Phe Asn Val Ile Val Glu Ala Leu Ser Lys Ser Lys Ala Glu Leu
1               5                   10                  15

<210> SEQ ID NO 136
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 136

Leu Ser Lys Ser Lys Ala Glu Leu Met Glu Ile Ser Glu Asp Lys Thr
1               5                   10                  15

<210> SEQ ID NO 137
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ser Lys Ala Glu Leu Met Glu Ile Ser Glu Asp Lys Thr Lys Ile Arg
1               5                   10                  15

<210> SEQ ID NO 138
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Arg Arg Ser Pro Ser Lys Pro Leu Pro Glu Val Thr Asp Glu Tyr
1               5                   10                  15

<210> SEQ ID NO 139
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Pro Ser Lys Pro Leu Pro Glu Val Thr Asp Glu Tyr Lys Asn Asp Val
1               5                   10                  15

<210> SEQ ID NO 140
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Lys Phe Gly Ala Asp Ala Arg Ala Leu Met Leu Gln Gly Val Asp Leu
1               5                   10                  15

Leu Ala Asp Ala
            20

<210> SEQ ID NO 141
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Leu Lys Val Gly Leu Gln Val Val Ala Val Lys Ala Pro Gly Phe
1               5                   10                  15

<210> SEQ ID NO 142
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gly Gly Ala Val Phe Gly Glu Glu Gly Leu Thr Leu Asn Leu Glu
1               5                   10                  15

<210> SEQ ID NO 143
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Thr Leu Asn Leu Glu Asp Val Gln Pro His Asp Leu Gly Lys Val
1               5                   10                  15

<210> SEQ ID NO 144
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Val Gly Ala Ala Thr Glu Ile Glu Met Lys Glu Lys Lys Asp Arg
1               5                   10                  15

<210> SEQ ID NO 145
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Val Gly Gly Thr Ser Asp Val Glu Val Asn Glu Lys Lys Asp Arg
1               5                   10                  15

<210> SEQ ID NO 146
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ile Val Leu Gly Gly Gly Cys Ala Leu Leu Arg Cys Ile Pro Ala
1               5                   10                  15

<210> SEQ ID NO 147
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Val Leu Gly Gly Gly Val Ala Leu Leu Arg Val Ile Pro Ala Leu Asp
```

```
                1               5                   10                  15
Ser Leu Thr Pro Ala Asn Glu Asp
            20

<210> SEQ ID NO 148
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Cys Ala Leu Leu Arg Cys Ile Pro Ala Leu Asp Ser Leu Thr
1               5                   10                  15

<210> SEQ ID NO 149
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Arg Cys Ile Pro Ala Leu Asp Ser Leu Thr Pro Ala Asn Glu Asp
1               5                   10                  15

<210> SEQ ID NO 150
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Glu Ile Ile Lys Arg Thr Leu Lys Ile Pro Ala Met Thr Ile Ala
1               5                   10                  15

<210> SEQ ID NO 151
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Val Glu Lys Ile Met Gln Ser Ser Glu Val Gly Tyr Asp Ala
1               5                   10                  15

<210> SEQ ID NO 152
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Met Ala Gly Asp Phe Val Asn Met Val Glu Lys Gly Ile Ile Asp
1               5                   10                  15

<210> SEQ ID NO 153
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 153

Val Asn Met Val Glu Lys Gly Ile Ile Asp Pro Thr Lys Val Val
1               5                   10                  15

<210> SEQ ID NO 154
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Val Ala Val Thr Met Gly Pro Lys Gly Arg Thr Val Ile Ile Glu
1               5                   10                  15

<210> SEQ ID NO 155
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Lys Gly Ile Ile Asp Pro Thr Lys Val Val Arg Thr Ala Leu Leu
1               5                   10                  15

<210> SEQ ID NO 156
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Pro Thr Lys Val Val Arg Thr Ala Leu Leu Asp Ala Ala Gly Val
1               5                   10                  15

<210> SEQ ID NO 157
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ala Ser Leu Leu Thr Thr Ala Glu Val Val Val Thr Glu Ile Pro
1               5                   10                  15

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gly Glu Thr Arg Lys Val Lys Ala His
1               5
```

```
<210> SEQ ID NO 159
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Arg Lys Val Lys Ala His Ser Gln Thr His Arg Val Asp Leu Gly
1               5                   10                  15

<210> SEQ ID NO 160
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Arg Val Asp Leu Gly Thr Leu Arg Gly Tyr Tyr Asn Gln Ser Glu
1               5                   10                  15

<210> SEQ ID NO 161
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Asp Gly Arg Leu Leu Arg Gly His Asp Gln Tyr Ala Tyr Asp Gly
1               5                   10                  15

<210> SEQ ID NO 162
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gly Pro Glu Tyr Trp Asp Arg Asn Thr Gln Ile Tyr Lys Ala
1               5                   10

<210> SEQ ID NO 163
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Trp Asp Arg Asn Thr Gln Ile Tyr Lys Ala Gln Ala Gln Thr Asp Arg
1               5                   10                  15

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164
```

Arg Asn Thr Gln Ile Tyr Lys Ala Gln
1               5

<210> SEQ ID NO 165
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Arg Glu Ser Leu Arg Asn Leu Arg Gly Tyr Tyr Asn Gln Ser Glu
1               5                   10                  15

<210> SEQ ID NO 166
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Gly Ser His Thr Leu Gln Ser Met Tyr Gly Cys Asp Val Gly Pro
1               5                   10                  15

<210> SEQ ID NO 167
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Leu Asn Glu Asp Leu Arg Ser Trp Thr Ala Ala Asp
1               5                   10

<210> SEQ ID NO 168
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Leu Asn Glu Asp Leu Arg Ser Trp Thr Ala Ala Asx Thr Ala Ala
1               5                   10                  15

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Asp Lys Gly Gln Val Leu Asn Ile Gln
1               5

<210> SEQ ID NO 170
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 170

Leu Glu Asp Lys Gly Gln Val Leu Asn Ile Gln Met Arg Arg
1               5                   10

<210> SEQ ID NO 171
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ala Phe Lys Gly Ser Ile Phe Val Val Phe Asp Ser Ile Glu
1               5                   10

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Glu Ser Ala Lys Lys Phe Val Glu Thr
1               5

<210> SEQ ID NO 173
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ile Glu Ser Ala Lys Lys Phe Val Glu Thr Pro Gly Gln Lys
1               5                   10

<210> SEQ ID NO 174
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ala Lys Asp Ala Asn Asn Gly Asn Leu Gln Leu Arg
1               5                   10

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Glu Ala Leu Lys Lys Ile Ile Glu Asp
1               5

<210> SEQ ID NO 176
<211> LENGTH: 9

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Glu Gln Ile Lys Leu Asp Glu Gly Trp
1               5

<210> SEQ ID NO 177
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Leu Lys Glu Gln Ile Lys Leu Asp Glu Gly Trp Val
1               5                   10

<210> SEQ ID NO 178
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ala Glu Leu Met Glu Ile Ser Glu Asp
1               5

<210> SEQ ID NO 179
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ser Lys Ala Glu Leu Met Glu Ile Ser Glu Asp Lys Thr
1               5                   10

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Lys Gly Ser Ile Phe Val Val Phe Asp
1               5

<210> SEQ ID NO 181
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ala Lys Asp Ala Asn Asn Gly Asn Leu Gln Leu Arg Asn Lys
1               5                   10
```

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Asp Ala Asn Asn Gly Asn Leu Gln Leu
1               5

<210> SEQ ID NO 183
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ile Val Glu Ala Leu Ser Lys Ser Lys Ala Glu Leu
1               5                   10

<210> SEQ ID NO 184
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ala Phe Lys Gly Ser Ile Phe Val Val Phe Asp Ser Ile
1               5                   10

<210> SEQ ID NO 185
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gly Ser Ile Phe Val Val Phe Asp Ser Ile Glu Ser Ala Lys
1               5                   10

<210> SEQ ID NO 186
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ile Phe Val Val Phe Asp Ser Ile Glu Ser Ala Lys Lys Phe
1               5                   10

<210> SEQ ID NO 187
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Val Val Phe Asp Ser Ile Glu Ser Ala
1               5

<210> SEQ ID NO 188
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Glu Leu Met Glu Ile Ser Glu Asp Lys Thr Lys Ile Arg
1               5                   10

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Glu Ala Leu Tyr Leu Val Cys Gly Glu
1               5

<210> SEQ ID NO 190
<211> LENGTH: 573
<212> TYPE: PRT
<213> ORGANISM: Homo sapiens

<400> SEQUENCE: 190

Met Leu Arg Leu Pro Thr Val Phe Arg Gln Met Arg Pro Val Ser Arg
1               5                   10                  15

Val Leu Ala Pro His Leu Thr Arg Ala Tyr Ala Lys Asp Val Lys Phe
                20                  25                  30

Gly Ala Asp Ala Arg Ala Leu Met Leu Gln Gly Val Asp Leu Leu Ala
            35                  40                  45

Asp Ala Val Ala Val Thr Met Gly Pro Lys Gly Arg Thr Val Ile Ile
        50                  55                  60

Glu Gln Ser Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ala Gly Asp Gly
            100                 105                 110

Thr Thr Thr Ala Thr Val Leu Ala Arg Ser Ile Ala Lys Glu Gly Phe
        115                 120                 125

Glu Lys Ile Ser Lys Gly Ala Asn Pro Val Glu Ile Arg Arg Gly Val
    130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
                165                 170                 175

Asn Gly Asp Lys Glu Ile Gly Asn Ile Ile Ser Asp Ala Met Lys Lys
            180                 185                 190

Val Gly Arg Lys Gly Val Ile Thr Val Lys Asp Gly Lys Thr Leu Asn
        195                 200                 205

```
Asp Glu Leu Glu Ile Ile Glu Gly Met Lys Phe Asp Arg Gly Tyr Ile
            210                 215                 220
Ser Pro Tyr Phe Ile Asn Thr Ser Lys Gly Gln Lys Cys Glu Phe Gln
225                 230                 235                 240
Asp Ala Tyr Val Leu Leu Ser Glu Lys Lys Ile Ser Ser Ile Gln Ser
                245                 250                 255
Ile Val Pro Ala Leu Glu Ile Ala Asn Ala His Arg Lys Pro Leu Val
            260                 265                 270
Ile Ile Ala Glu Asp Val Asp Gly Glu Ala Leu Ser Thr Leu Val Leu
        275                 280                 285
Asn Arg Leu Lys Val Gly Leu Gln Val Val Ala Val Lys Ala Pro Gly
        290                 295                 300
Phe Gly Asp Asn Arg Lys Asn Gln Leu Lys Asp Met Ala Ile Ala Thr
305                 310                 315                 320
Gly Gly Ala Val Phe Gly Glu Glu Gly Leu Thr Leu Asn Leu Glu Asp
                325                 330                 335
Val Gln Pro His Asp Leu Gly Lys Val Gly Glu Val Ile Val Thr Lys
                340                 345                 350
Asp Asp Ala Met Leu Leu Lys Gly Lys Gly Asp Lys Ala Gln Ile Glu
            355                 360                 365
Lys Arg Ile Gln Glu Ile Ile Glu Gln Leu Asp Val Thr Thr Ser Glu
        370                 375                 380
Tyr Glu Lys Glu Lys Leu Asn Glu Arg Leu Ala Lys Leu Ser Asp Gly
385                 390                 395                 400
Val Ala Val Leu Lys Val Gly Gly Thr Ser Asp Val Glu Val Asn Glu
                405                 410                 415
Lys Lys Asp Arg Val Thr Asp Ala Leu Asn Ala Thr Arg Ala Ala Val
            420                 425                 430
Glu Glu Gly Ile Val Leu Gly Gly Gly Cys Ala Leu Leu Arg Cys Ile
        435                 440                 445
Pro Ala Leu Asp Ser Leu Thr Pro Ala Asn Glu Asp Gln Lys Ile Gly
        450                 455                 460
Ile Glu Ile Ile Lys Arg Thr Leu Lys Ile Pro Ala Met Thr Ile Ala
465                 470                 475                 480
Lys Asn Ala Gly Val Glu Gly Ser Leu Ile Val Glu Lys Ile Met Gln
                485                 490                 495
Ser Ser Ser Glu Val Gly Tyr Asp Ala Met Ala Gly Asp Phe Val Asn
            500                 505                 510
Met Val Glu Lys Gly Ile Ile Asp Pro Thr Lys Val Val Arg Thr Ala
        515                 520                 525
Leu Leu Asp Ala Ala Gly Val Ala Ser Leu Leu Thr Thr Ala Glu Val
        530                 535                 540
Val Val Thr Glu Ile Pro Lys Glu Glu Lys Asp Pro Gly Met Gly Ala
545                 550                 555                 560
Met Gly Gly Met Gly Gly Gly Met Gly Gly Met Phe
                565                 570

<210> SEQ ID NO 191
<211> LENGTH: 641
<212> TYPE: PRT
<213> ORGANISM: Homo sapiens

<400> SEQUENCE: 191

Met Ala Lys Ala Ala Ala Ile Gly Ile Asp Leu Gly Thr Thr Tyr Ser
1               5                   10                  15
```

-continued

```
Cys Val Gly Val Phe Gln His Gly Lys Val Glu Ile Ile Ala Asn Asp
             20                  25                  30

Gln Gly Asn Arg Thr Thr Pro Ser Tyr Val Ala Phe Thr Asp Thr Glu
         35                  40                  45

Arg Leu Ile Gly Asp Ala Ala Lys Asn Gln Val Ala Leu Asn Pro Gln
 50                  55                  60

Asn Thr Val Phe Asp Ala Lys Arg Leu Ile Gly Arg Lys Phe Gly Asp
 65                  70                  75                  80

Pro Val Val Gln Ser Asp Met Lys His Trp Pro Phe Gln Val Ile Asn
                 85                  90                  95

Asp Gly Asp Lys Pro Lys Val Gln Val Ser Tyr Lys Gly Glu Thr Lys
             100                 105                 110

Ala Phe Tyr Pro Glu Glu Ile Ser Ser Met Val Leu Thr Lys Met Lys
         115                 120                 125

Glu Ile Ala Glu Ala Tyr Leu Gly Tyr Pro Val Thr Asn Ala Val Ile
     130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                 165                 170                 175

Thr Ala Ala Ala Ile Ala Tyr Gly Leu Asp Arg Thr Gly Lys Gly Glu
             180                 185                 190

Arg Asn Val Leu Ile Phe Asp Leu Gly Gly Gly Thr Phe Asp Val Ser
         195                 200                 205

Ile Leu Thr Ile Asp Asp Gly Ile Phe Glu Val Lys Ala Thr Ala Gly
 210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                 245                 250                 255

Lys Arg Ala Val Arg Arg Leu Arg Thr Ala Cys Glu Arg Ala Lys Arg
             260                 265                 270

Thr Leu Ser Ser Ser Thr Gln Ala Ser Leu Glu Ile Asp Ser Leu Phe
         275                 280                 285

Glu Gly Ile Asp Phe Tyr Thr Ser Ile Thr Arg Ala Arg Phe Glu Glu
 290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                 325                 330                 335

Val Gly Gly Ser Thr Arg Ile Pro Lys Val Gln Lys Leu Leu Gln Asp
             340                 345                 350

Phe Phe Asn Gly Arg Asp Leu Asn Lys Ser Ile Asn Pro Asp Glu Ala
         355                 360                 365

Val Ala Tyr Gly Ala Ala Val Gln Ala Ala Ile Leu Met Gly Asp Lys
 370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                 405                 410                 415

Asn Ser Thr Ile Pro Thr Lys Gln Thr Gln Ile Phe Thr Thr Tyr Ser
             420                 425                 430

Asp Asn Gln Pro Gly Val Leu Ile Gln Val Tyr Glu Gly Glu Arg Ala
         435                 440                 445
```

```
Met Thr Lys Asp Asn Asn Leu Leu Gly Arg Phe Glu Leu Ser Gly Ile
            450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
            500                 505                 510

Glu Glu Ile Glu Arg Met Val Gln Glu Ala Glu Lys Tyr Lys Ala Glu
        515                 520                 525

Asp Glu Val Gln Arg Glu Arg Val Ser Ala Lys Asn Ala Leu Glu Ser
530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Lys Val Leu Asp Lys Cys Gln Glu
                565                 570                 575

Val Ile Ser Trp Leu Asp Ala Asn Thr Leu Ala Glu Lys Asp Glu Phe
            580                 585                 590

Glu His Lys Arg Lys Glu Leu Glu Gln Val Cys Asn Pro Ile Ile Ser
        595                 600                 605

Gly Leu Tyr Gln Gly Ala Gly Gly Pro Gly Pro Gly Gly Phe Gly Ala
    610                 615                 620

Gln Gly Pro Lys Gly Gly Ser Gly Ser Gly Pro Thr Ile Glu Glu Val
625                 630                 635                 640

Asp

<210> SEQ ID NO 192
<211> LENGTH: 731
<212> TYPE: PRT
<213> ORGANISM: Homo sapiens

<400> SEQUENCE: 192

Pro Glu Glu Thr Gln Thr Gln Asp Gln Pro Met Glu Glu Glu Glu Val
1               5                   10                  15

Glu Thr Phe Ala Phe Gln Ala Glu Ile Ala Gln Leu Met Ser Leu Ile
            20                  25                  30

Ile Asn Thr Phe Tyr Ser Asn Lys Glu Ile Phe Leu Arg Glu Leu Ile
        35                  40                  45

Ser Asn Ser Ser Asp Ala Leu Asp Lys Ile Arg Tyr Glu Ser Leu Thr
    50                  55                  60

Asp Pro Ser Lys Leu Asp Ser Gly Lys Glu Leu His Ile Asn Leu Ile
65                  70                  75                  80

Pro Asn Lys Gln Asp Arg Thr Leu Thr Ile Val Asp Thr Gly Ile Gly
                85                  90                  95

Met Thr Lys Ala Asp Leu Ile Asn Asn Leu Gly Thr Ile Ala Lys Ser
            100                 105                 110

Gly Thr Lys Ala Phe Met Glu Ala Leu Gln Ala Gly Ala Asp Ile Ser
        115                 120                 125

Met Ile Gly Gln Phe Gly Val Gly Phe Tyr Ser Ala Tyr Leu Val Ala
    130                 135                 140

Glu Lys Val Thr Val Ile Thr Lys His Asn Asp Asp Glu Gln Tyr Ala
145                 150                 155                 160

Trp Glu Ser Ser Ala Gly Gly Ser Phe Thr Val Arg Thr Asp Thr Gly
                165                 170                 175
```

-continued

```
Glu Pro Met Gly Arg Gly Thr Lys Val Ile Leu His Leu Lys Glu Asp
                180                 185                 190
Gln Thr Glu Tyr Leu Glu Glu Arg Ile Lys Glu Ile Val Lys Lys
            195                 200                 205
His Ser Gln Phe Ile Gly Tyr Pro Ile Thr Leu Phe Val Glu Lys Glu
        210                 215                 220
Arg Asp Lys Glu Val Ser Asp Glu Ala Glu Glu Lys Glu Asp Lys
225                 230                 235                 240
Glu Glu Glu Lys Glu Lys Glu Lys Glu Ser Glu Asp Lys Pro Glu
                245                 250                 255
Ile Glu Asp Val Gly Ser Asp Glu Glu Glu Lys Lys Asp Gly Asp
            260                 265                 270
Lys Lys Lys Lys Lys Lys Ile Lys Glu Lys Tyr Ile Asp Gln Glu Glu
        275                 280                 285
Leu Asn Lys Thr Lys Pro Ile Trp Thr Arg Asn Pro Asp Asp Ile Thr
        290                 295                 300
Asn Glu Glu Tyr Gly Glu Phe Tyr Lys Ser Leu Thr Asn Asp Trp Glu
305                 310                 315                 320
Asp His Leu Ala Val Lys His Phe Ser Val Glu Gly Gln Leu Glu Phe
                325                 330                 335
Arg Ala Leu Leu Phe Val Pro Arg Arg Ala Pro Phe Asp Leu Phe Glu
                340                 345                 350
Asn Arg Lys Lys Lys Asn Asn Ile Lys Leu Tyr Val Arg Arg Val Phe
            355                 360                 365
Ile Met Asp Asn Cys Glu Glu Leu Ile Pro Glu Tyr Leu Asn Phe Ile
        370                 375                 380
Arg Gly Val Val Asp Ser Glu Asp Leu Pro Leu Asn Ile Ser Arg Glu
385                 390                 395                 400
Met Leu Gln Gln Ser Lys Ile Leu Lys Val Ile Arg Lys Asn Leu Val
                405                 410                 415
Lys Lys Cys Leu Glu Leu Phe Thr Glu Leu Ala Glu Asp Lys Glu Asn
                420                 425                 430
Tyr Lys Lys Phe Tyr Glu Gln Phe Ser Lys Asn Ile Lys Leu Gly Ile
            435                 440                 445
His Glu Asp Ser Gln Asn Arg Lys Lys Leu Ser Glu Leu Leu Arg Tyr
        450                 455                 460
Tyr Thr Ser Ala Ser Gly Asp Glu Met Val Ser Leu Lys Asp Tyr Cys
465                 470                 475                 480
Thr Arg Met Lys Glu Asn Gln Lys His Ile Tyr Tyr Ile Thr Gly Glu
                485                 490                 495
Thr Lys Asp Gln Val Ala Asn Ser Ala Phe Val Glu Arg Leu Arg Lys
            500                 505                 510
His Gly Leu Glu Val Ile Tyr Met Ile Glu Pro Ile Asp Glu Tyr Cys
        515                 520                 525
Val Gln Gln Leu Lys Glu Phe Glu Gly Lys Thr Leu Val Ser Val Thr
        530                 535                 540
Lys Glu Gly Leu Glu Leu Pro Glu Asp Glu Glu Glu Lys Lys Lys Gln
545                 550                 555                 560
Glu Glu Lys Lys Thr Lys Phe Glu Asn Leu Cys Lys Ile Met Lys Asp
                565                 570                 575
Ile Leu Glu Lys Lys Val Glu Lys Val Val Ser Asn Arg Leu Val
            580                 585                 590
Thr Ser Pro Cys Cys Ile Val Thr Ser Thr Tyr Gly Trp Thr Ala Asn
        595                 600                 605
```

```
Met Glu Arg Ile Met Lys Ala Gln Ala Leu Arg Asp Asn Ser Thr Met
    610                 615                 620
Gly Tyr Met Ala Ala Lys Lys His Leu Glu Ile Asn Pro Asp His Ser
625                 630                 635                 640
Ile Ile Glu Thr Leu Arg Gln Lys Ala Glu Ala Asp Lys Asn Asp Lys
                645                 650                 655
Ser Val Lys Asp Leu Val Ile Leu Leu Tyr Glu Thr Ala Leu Leu Ser
            660                 665                 670
Ser Gly Phe Ser Leu Glu Asp Pro Gln Thr His Ala Asn Arg Ile Tyr
        675                 680                 685
Arg Met Ile Lys Leu Gly Leu Gly Ile Asp Glu Asp Asp Pro Thr Ala
690                 695                 700
Asp Asp Thr Ser Ala Ala Val Thr Glu Glu Met Pro Pro Leu Glu Gly
705                 710                 715                 720
Asp Asp Asp Thr Ser Arg Met Glu Glu Val Asp
                725                 730

<210> SEQ ID NO 193
<211> LENGTH: 723
<212> TYPE: PRT
<213> ORGANISM: Homo sapiens

<400> SEQUENCE: 193

Pro Glu Glu Val His His Gly Glu Glu Val Glu Thr Phe Ala Phe
1               5                   10                  15
Gln Ala Glu Ile Ala Gln Leu Met Ser Leu Ile Ile Asn Thr Phe Tyr
            20                  25                  30
Ser Asn Lys Glu Ile Phe Leu Arg Glu Leu Ile Ser Asn Ala Ser Asp
        35                  40                  45
Ala Leu Asp Lys Ile Arg Tyr Glu Ser Leu Thr Asp Pro Ser Lys Leu
    50                  55                  60
Asp Ser Gly Lys Glu Leu Lys Ile Asp Ile Ile Pro Asn Pro Gln Glu
65                  70                  75                  80
Arg Thr Leu Thr Leu Val Asp Thr Gly Ile Gly Met Thr Lys Ala Asp
                85                  90                  95
Leu Ile Asn Asn Leu Gly Thr Ile Ala Lys Ser Gly Thr Lys Ala Phe
            100                 105                 110
Met Glu Ala Leu Gln Ala Gly Ala Asp Ile Ser Met Ile Gly Gln Phe
        115                 120                 125
Gly Val Gly Phe Tyr Ser Ala Tyr Leu Val Ala Glu Lys Val Val Val
    130                 135                 140
Ile Thr Lys His Asn Asp Asp Glu Gln Tyr Ala Trp Glu Ser Ser Ala
145                 150                 155                 160
Gly Gly Ser Phe Thr Val Arg Ala Asp His Gly Glu Pro Ile Gly Arg
                165                 170                 175
Gly Thr Lys Val Ile Leu His Leu Lys Glu Asp Gln Thr Glu Tyr Leu
            180                 185                 190
Glu Glu Arg Arg Val Lys Glu Val Val Lys Lys His Ser Gln Phe Ile
        195                 200                 205
Gly Tyr Pro Ile Thr Leu Tyr Leu Glu Lys Glu Arg Glu Lys Glu Ile
    210                 215                 220
Ser Asp Asp Glu Ala Glu Glu Lys Glu Asp Lys Glu Glu Glu Glu Asp
225                 230                 235                 240
Lys Asp Asp Glu Glu Lys Pro Lys Ile Glu Asp Val Gly Ser Asp Glu
                245                 250                 255
```

```
Glu Asp Asp Ser Gly Lys Asp Lys Lys Lys Thr Lys Lys Ile Lys
            260                 265                 270

Glu Lys Tyr Ile Asp Gln Glu Leu Asn Lys Thr Lys Pro Ile Trp
        275                 280                 285

Thr Arg Asn Pro Asp Asp Ile Thr Gln Glu Glu Tyr Gly Glu Phe Tyr
    290                 295                 300

Lys Ser Leu Thr Asn Asp Trp Glu Asp His Leu Ala Val Lys His Phe
305                 310                 315                 320

Ser Val Glu Gly Gln Leu Glu Phe Arg Ala Leu Leu Phe Ile Pro Arg
                325                 330                 335

Arg Ala Pro Phe Asp Leu Phe Glu Asn Lys Lys Lys Lys Asn Asn Ile
                340                 345                 350

Lys Leu Tyr Val Arg Arg Val Phe Ile Met Asp Ser Cys Asp Glu Leu
            355                 360                 365

Ile Pro Glu Tyr Leu Asn Phe Ile Arg Gly Val Val Asp Ser Glu Asp
    370                 375                 380

Leu Pro Leu Asn Ile Ser Arg Glu Met Leu Gln Gln Ser Lys Ile Leu
385                 390                 395                 400

Lys Val Ile Arg Lys Asn Ile Val Lys Lys Cys Leu Glu Leu Phe Ser
                405                 410                 415

Glu Leu Ala Glu Asp Lys Glu Asn Tyr Lys Lys Phe Tyr Glu Ala Phe
                420                 425                 430

Ser Lys Asn Leu Lys Leu Gly Ile His Glu Asp Ser Thr Asn Arg Arg
        435                 440                 445

Arg Leu Ser Glu Leu Leu Arg Tyr His Thr Ser Gln Ser Gly Asp Glu
    450                 455                 460

Met Thr Ser Leu Ser Glu Tyr Val Ser Arg Met Lys Glu Thr Gln Lys
465                 470                 475                 480

Ser Ile Tyr Tyr Ile Thr Gly Glu Ser Lys Glu Gln Val Ala Asn Ser
                485                 490                 495

Ala Phe Val Glu Arg Val Arg Lys Arg Gly Phe Glu Val Val Tyr Met
                500                 505                 510

Thr Glu Pro Ile Asp Glu Tyr Cys Val Gln Gln Leu Lys Glu Phe Asp
        515                 520                 525

Gly Lys Ser Leu Val Ser Val Thr Lys Glu Gly Leu Glu Leu Pro Glu
530                 535                 540

Asp Glu Glu Glu Lys Lys Lys Met Glu Glu Ser Lys Ala Lys Phe Glu
545                 550                 555                 560

Asn Leu Cys Lys Leu Met Lys Glu Ile Leu Asp Lys Lys Val Glu Lys
                565                 570                 575

Val Thr Ile Ser Asn Arg Leu Val Ser Ser Pro Cys Cys Ile Val Thr
                580                 585                 590

Ser Thr Tyr Gly Trp Thr Ala Asn Met Glu Arg Ile Met Lys Ala Gln
            595                 600                 605

Ala Leu Arg Asp Asn Ser Thr Met Gly Tyr Met Met Ala Lys Lys His
        610                 615                 620

Leu Glu Ile Asn Pro Asp His Pro Ile Val Glu Thr Leu Arg Gln Lys
625                 630                 635                 640

Ala Glu Ala Asp Lys Asn Asp Lys Ala Val Lys Asp Leu Val Val Leu
                645                 650                 655

Leu Phe Glu Thr Ala Leu Leu Ser Ser Gly Phe Ser Leu Glu Asp Pro
            660                 665                 670

Gln Thr His Ser Asn Arg Ile Tyr Arg Met Ile Lys Leu Gly Leu Gly
```

```
                675                 680                 685
Ile Asp Glu Asp Glu Val Ala Ala Glu Glu Pro Asn Ala Ala Val Pro
690                 695                 700

Asp Glu Ile Pro Pro Leu Glu Gly Asp Glu Asp Ala Ser Arg Met Glu
705                 710                 715                 720

Glu Val Asp

<210> SEQ ID NO 194
<211> LENGTH: 585
<212> TYPE: PRT
<213> ORGANISM: Homo sapiens

<400> SEQUENCE: 194

Met Ala Ser Pro Gly Ser Gly Phe Trp Ser Phe Gly Ser Glu Asp Gly
1               5                   10                  15

Ser Gly Asp Ser Glu Asn Pro Gly Thr Ala Arg Ala Trp Cys Gln Val
                20                  25                  30

Ala Gln Lys Phe Thr Gly Gly Ile Gly Asn Lys Leu Cys Ala Leu Leu
            35                  40                  45

Tyr Gly Asp Ala Glu Lys Pro Ala Glu Ser Gly Gly Ser Gln Pro Pro
50                  55                  60

Arg Ala Ala Ala Arg Lys Ala Ala Cys Ala Cys Asp Gln Lys Pro Cys
65                  70                  75                  80

Ser Cys Ser Lys Val Asp Val Asn Tyr Ala Phe Leu His Ala Thr Asp
                85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
        115                 120                 125

Ser Thr Lys Val Ile Asp Phe His Tyr Pro Asn Glu Leu Leu Gln Glu
130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
        195                 200                 205

Ile Ala Pro Val Phe Val Leu Leu Glu Tyr Val Thr Leu Lys Lys Met
210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
                245                 250                 255

Lys Met Phe Pro Glu Val Lys Glu Lys Gly Met Ala Ala Leu Pro Arg
            260                 265                 270

Leu Ile Ala Phe Thr Ser Glu His Ser His Phe Ser Leu Lys Lys Gly
        275                 280                 285

Ala Ala Ala Leu Gly Ile Gly Thr Asp Ser Val Ile Leu Ile Lys Cys
290                 295                 300

Asp Glu Arg Gly Lys Met Ile Pro Ser Asp Leu Glu Arg Arg Ile Leu
305                 310                 315                 320

Glu Ala Lys Gln Lys Gly Phe Val Pro Phe Leu Val Ser Ala Thr Ala
                325                 330                 335
```

```
Gly Thr Thr Val Tyr Gly Ala Phe Asp Pro Leu Leu Ala Val Ala Asp
                340                 345                 350

Ile Cys Lys Lys Tyr Lys Ile Trp Met His Val Asp Ala Ala Trp Gly
            355                 360                 365

Gly Gly Leu Leu Met Ser Arg Lys His Lys Trp Lys Leu Ser Gly Val
370                 375                 380

Glu Arg Ala Asn Ser Val Thr Trp Asn Pro His Lys Met Met Gly Val
385                 390                 395                 400

Pro Leu Gln Cys Ser Ala Leu Leu Val Arg Glu Gly Leu Met Gln
                405                 410                 415

Asn Cys Asn Gln Met His Ala Ser Tyr Leu Phe Gln Gln Asp Lys His
                420                 425                 430

Tyr Asp Leu Ser Tyr Asp Thr Gly Asp Lys Ala Leu Gln Cys Gly Arg
                435                 440                 445

His Val Asp Val Phe Lys Leu Trp Leu Met Trp Arg Ala Lys Gly Thr
                450                 455                 460

Thr Gly Phe Glu Ala His Val Asp Lys Cys Leu Glu Leu Ala Glu Tyr
465                 470                 475                 480

Leu Tyr Asn Ile Ile Lys Asn Arg Glu Gly Tyr Glu Met Val Phe Asp
                485                 490                 495

Gly Lys Pro Gln His Thr Asn Val Cys Phe Trp Tyr Ile Pro Pro Ser
                500                 505                 510

Leu Arg Thr Leu Glu Asp Asn Glu Glu Arg Met Ser Arg Leu Ser Lys
                515                 520                 525

Val Ala Pro Val Ile Lys Ala Arg Met Met Glu Tyr Gly Thr Thr Met
                530                 535                 540

Val Ser Tyr Gln Pro Leu Gly Asp Lys Val Asn Phe Phe Arg Met Val
545                 550                 555                 560

Ile Ser Asn Pro Ala Ala Thr His Gln Asp Ile Asp Phe Leu Ile Glu
                565                 570                 575

Glu Ile Glu Arg Leu Gly Gln Asp Leu
                580                 585

<210> SEQ ID NO 195
<211> LENGTH: 525
<212> TYPE: PRT
<213> ORGANISM: Homo sapiens

<400> SEQUENCE: 195

Met Glu Glu Ser Val Asn Gln Met Gln Pro Leu Asn Glu Lys Gln Ile
1               5                   10                  15

Ala Asn Ser Gln Asp Gly Tyr Val Trp Gln Val Thr Asp Met Asn Arg
                20                  25                  30

Leu His Arg Phe Leu Cys Phe Gly Ser Glu Gly Gly Thr Tyr Tyr Ile
            35                  40                  45

Lys Glu Gln Lys Leu Gly Leu Glu Asn Ala Glu Ala Leu Ile Arg Leu
        50                  55                  60

Ile Glu Asp Gly Arg Gly Cys Glu Val Ile Gln Glu Ile Lys Ser Phe
65                  70                  75                  80

Ser Gln Glu Gly Arg Thr Thr Lys Gln Glu Pro Met Leu Phe Ala Leu
                85                  90                  95

Ala Ile Cys Ser Gln Cys Ser Asp Ile Ser Thr Lys Gln Ala Ala Phe
            100                 105                 110

Lys Ala Val Ser Glu Val Cys Arg Ile Pro Thr His Leu Phe Thr Phe
        115                 120                 125
```

```
Ile Gln Phe Lys Lys Asp Leu Lys Glu Ser Met Lys Cys Gly Met Trp
    130                 135                 140

Gly Arg Ala Leu Arg Lys Ala Ile Ala Asp Trp Tyr Asn Glu Lys Gly
145                 150                 155                 160

Gly Met Ala Leu Ala Leu Ala Val Thr Lys Tyr Lys Gln Arg Asn Gly
                165                 170                 175

Trp Ser His Lys Asp Leu Leu Arg Leu Ser His Leu Lys Pro Ser Ser
            180                 185                 190

Glu Gly Leu Ala Ile Val Thr Lys Tyr Ile Thr Lys Gly Trp Lys Glu
        195                 200                 205

Val His Glu Leu Tyr Lys Glu Lys Ala Leu Ser Val Glu Thr Glu Lys
    210                 215                 220

Leu Leu Lys Tyr Leu Glu Ala Val Glu Lys Val Lys Arg Thr Arg Asp
225                 230                 235                 240

Glu Leu Glu Val Ile His Leu Ile Glu Glu His Arg Leu Val Arg Glu
                245                 250                 255

His Leu Leu Thr Asn His Leu Lys Ser Lys Glu Val Trp Lys Ala Leu
            260                 265                 270

Leu Gln Glu Met Pro Leu Thr Ala Leu Leu Arg Asn Leu Gly Lys Met
        275                 280                 285

Thr Ala Asn Ser Val Leu Glu Pro Gly Asn Ser Glu Val Ser Leu Val
290                 295                 300

Cys Glu Lys Leu Cys Asn Glu Lys Leu Leu Lys Lys Ala Arg Ile His
305                 310                 315                 320

Pro Phe His Ile Leu Ile Ala Leu Glu Thr Tyr Lys Thr Gly His Gly
                325                 330                 335

Leu Arg Gly Lys Leu Lys Trp Arg Pro Asp Glu Glu Ile Leu Lys Ala
            340                 345                 350

Leu Asp Ala Ala Phe Tyr Lys Thr Phe Lys Thr Val Glu Pro Thr Gly
        355                 360                 365

Lys Arg Phe Leu Leu Ala Val Asp Val Ser Ala Ser Met Asn Gln Arg
370                 375                 380

Val Leu Gly Ser Ile Leu Asn Ala Ser Thr Val Ala Ala Ala Met Cys
385                 390                 395                 400

Met Val Val Thr Arg Thr Glu Lys Asp Ser Tyr Val Val Ala Phe Ser
                405                 410                 415

Asp Glu Met Val Pro Cys Pro Val Thr Thr Asp Met Thr Leu Gln Gln
            420                 425                 430

Val Leu Met Ala Met Ser Gln Ile Pro Ala Gly Gly Thr Asp Cys Ser
        435                 440                 445

Leu Pro Met Ile Trp Ala Gln Lys Thr Asn Thr Pro Ala Asp Val Phe
450                 455                 460

Ile Val Phe Thr Asp Asn Glu Thr Phe Ala Gly Gly Val His Pro Ala
465                 470                 475                 480

Ile Ala Leu Arg Glu Tyr Arg Lys Lys Met Asp Ile Pro Ala Lys Leu
                485                 490                 495

Ile Val Cys Gly Met Thr Ser Asn Gly Phe Thr Ile Ala Asp Pro Asp
            500                 505                 510

Asp Arg Ala Leu Gln Asn Thr Leu Leu Asn Lys Ser Phe
        515                 520                 525

<210> SEQ ID NO 196
<211> LENGTH: 181
<212> TYPE: PRT
```

<213> ORGANISM: Homo sapiens

<400> SEQUENCE: 196

Val Ala Asp His Val Ala Ser Tyr Gly Val Asn Leu Tyr Gln Ser Tyr
1               5                   10                  15

Gly Pro Ser Gly Gln Tyr Thr His Glu Phe Asp Gly Asp Glu Gln Phe
            20                  25                  30

Tyr Val Asp Leu Gly Arg Lys Glu Thr Val Trp Cys Leu Pro Glu Leu
        35                  40                  45

Arg Gln Phe Arg Gly Phe Asp Pro Gln Phe Ala Leu Thr Asn Ile Ala
    50                  55                  60

Val Leu Lys His Asn Leu Asn Ser Leu Ile Lys Arg Ser Asn Ser Thr
65                  70                  75                  80

Ala Ala Thr Asn Glu Val Pro Glu Val Thr Val Phe Ser Lys Ser Pro
                85                  90                  95

Val Thr Leu Gly Gln Pro Asn Thr Leu Ile Cys Leu Val Asp Asn Ile
            100                 105                 110

Phe Pro Pro Val Val Asn Ile Thr Trp Leu Thr Asn Gly His Ser Val
        115                 120                 125

Thr Glu Gly Val Ser Glu Thr Thr Phe Leu Ser Lys Ser Asp His Ser
    130                 135                 140

Phe Phe Lys Ile Ser Tyr Leu Thr Leu Leu Pro Ser Ala Glu Glu Ser
145                 150                 155                 160

Tyr Asp Cys Lys Val Glu His Trp Gly Leu Asp Lys Pro Leu Leu Lys
                165                 170                 175

His Trp Glu Pro Glu
            180

<210> SEQ ID NO 197
<211> LENGTH: 190
<212> TYPE: PRT
<213> ORGANISM: Homo sapiens

<400> SEQUENCE: 197

Ser Pro Glu Asp Phe Val Tyr Gln Phe Lys Gly Met Cys Tyr Phe Thr
1               5                   10                  15

Asn Gly Thr Glu Arg Val Arg Leu Val Ser Arg Ser Ile Tyr Asn Arg
            20                  25                  30

Glu Glu Ile Val Arg Phe Asp Ser Asp Val Gly Glu Phe Arg Ala Val
        35                  40                  45

Thr Leu Leu Gly Leu Pro Ala Ala Glu Tyr Trp Asn Ser Gln Lys Asp
    50                  55                  60

Ile Leu Glu Arg Lys Arg Ala Ala Val Asp Arg Val Cys Arg His Asn
65                  70                  75                  80

Tyr Gln Leu Glu Leu Arg Thr Thr Leu Gln Arg Arg Val Glu Pro Thr
                85                  90                  95

Val Thr Ile Ser Pro Ser Arg Thr Glu Ala Leu Asn His His Asn Leu
            100                 105                 110

Leu Val Cys Ser Val Thr Asp Phe Tyr Pro Ala Gln Ile Lys Val Arg
        115                 120                 125

Trp Phe Arg Asn Asp Gln Glu Glu Thr Ala Gly Val Val Ser Thr Pro
    130                 135                 140

Leu Ile Arg Asn Gly Asp Trp Thr Phe Gln Ile Leu Val Met Leu Glu
145                 150                 155                 160

Met Thr Pro Gln Arg Gly Asp Val Tyr Thr Cys His Val Glu His Pro
                165                 170                 175

Ser Leu Gln Ser Pro Ile Thr Val Glu Trp Arg Ala Gln Ser
        180             185             190

<210> SEQ ID NO 198
<211> LENGTH: 181
<212> TYPE: PRT
<213> ORGANISM: Homo sapiens

<400> SEQUENCE: 198

Val Ala Asp His Val Ala Ser Tyr Gly Val Asn Leu Tyr Gln Ser Tyr
1               5                   10                  15

Gly Pro Ser Gly Gln Tyr Thr His Glu Phe Asp Gly Asp Glu Gln Phe
            20                  25                  30

Tyr Val Asp Leu Gly Arg Lys Glu Thr Val Trp Cys Leu Pro Glu Leu
        35                  40                  45

Arg Gln Phe Arg Gly Phe Asp Pro Gln Phe Ala Leu Thr Asn Ile Ala
    50                  55                  60

Val Leu Lys His Asn Leu Asn Ser Leu Ile Lys Arg Ser Asn Ser Thr
65                  70                  75                  80

Ala Ala Thr Asn Glu Val Pro Glu Val Thr Val Phe Ser Lys Ser Pro
                85                  90                  95

Val Thr Leu Gly Gln Pro Asn Thr Leu Ile Cys Leu Val Asp Asn Ile
            100                 105                 110

Phe Pro Pro Val Val Asn Ile Thr Trp Leu Thr Asn Gly His Ser Val
        115                 120                 125

Thr Glu Gly Val Ser Glu Thr Thr Phe Leu Ser Lys Ser Asp His Ser
    130                 135                 140

Phe Phe Lys Ile Ser Tyr Leu Thr Leu Leu Pro Ser Ala Glu Glu Ser
145                 150                 155                 160

Tyr Asp Cys Lys Val Glu His Trp Gly Leu Asp Lys Pro Leu Leu Lys
                165                 170                 175

His Trp Glu Pro Glu
            180

<210> SEQ ID NO 199
<211> LENGTH: 189
<212> TYPE: PRT
<213> ORGANISM: Homo sapiens

<400> SEQUENCE: 199

Ser Pro Glu Asp Phe Val Tyr Gln Phe Lys Ala Met Cys Tyr Phe Thr
1               5                   10                  15

Asn Gly Thr Glu Arg Val Tyr Val Thr Arg Tyr Ile Tyr Asn Arg Glu
            20                  25                  30

Glu Tyr Ala Arg Phe Asp Ser Asp Val Glu Val Tyr Arg Ala Val Thr
        35                  40                  45

Pro Leu Gly Pro Pro Asp Ala Glu Tyr Trp Asn Ser Gln Lys Glu Val
    50                  55                  60

Leu Glu Arg Thr Arg Ala Glu Leu Asp Thr Val Cys Arg His Asn Tyr
65                  70                  75                  80

Gln Leu Glu Leu Arg Thr Thr Leu Gln Arg Arg Val Glu Pro Thr Val
                85                  90                  95

Thr Ile Ser Pro Ser Arg Thr Glu Ala Leu Asn His His Asn Leu Leu
            100                 105                 110

Val Cys Ser Val Thr Asp Phe Tyr Pro Ala Gln Ile Lys Val Arg Trp
        115                 120                 125

```
Phe Arg Asn Asp Gln Glu Thr Thr Gly Val Val Ser Thr Pro Leu
    130                 135                 140

Ile Arg Asn Gly Asp Trp Thr Phe Gln Ile Leu Val Met Leu Glu Met
145                 150                 155                 160

Thr Pro Gln His Gly Asp Val Tyr Thr Cys His Val Glu His Pro Ser
                165                 170                 175

Leu Gln Asn Pro Ile Thr Val Glu Trp Arg Ala Gln Ser
                180                 185

<210> SEQ ID NO 200
<211> LENGTH: 181
<212> TYPE: PRT
<213> ORGANISM: Homo sapiens

<400> SEQUENCE: 200

Val Ala Asp His Val Ala Ser Tyr Gly Val Asn Leu Tyr Gln Ser Tyr
1               5                   10                  15

Gly Pro Ser Gly Gln Tyr Ser His Glu Phe Asp Gly Asp Glu Glu Phe
            20                  25                  30

Tyr Val Asp Leu Glu Arg Lys Glu Thr Val Trp Gln Leu Pro Leu Phe
        35                  40                  45

Arg Arg Phe Arg Arg Phe Asp Pro Gln Phe Ala Leu Thr Asn Ile Ala
    50                  55                  60

Val Leu Lys His Asn Leu Asn Ile Val Ile Lys Arg Ser Asn Ser Thr
65                  70                  75                  80

Ala Ala Thr Asn Glu Val Pro Glu Val Thr Val Phe Ser Lys Ser Pro
                85                  90                  95

Val Thr Leu Gly Gln Pro Asn Thr Leu Ile Cys Leu Val Asp Asn Ile
            100                 105                 110

Phe Pro Pro Val Val Asn Ile Thr Trp Leu Ser Asn Gly His Ser Val
        115                 120                 125

Thr Glu Gly Val Ser Glu Thr Ser Phe Leu Ser Lys Ser Asp His Ser
    130                 135                 140

Phe Phe Lys Ile Ser Tyr Leu Thr Phe Leu Pro Ser Asp Asp Glu Ile
145                 150                 155                 160

Tyr Asp Cys Lys Val Glu His Trp Gly Leu Asp Glu Pro Leu Leu Lys
                165                 170                 175

His Trp Glu Pro Glu
            180

<210> SEQ ID NO 201
<211> LENGTH: 191
<212> TYPE: PRT
<213> ORGANISM: Homo sapiens

<400> SEQUENCE: 201

Ser Pro Glu Asp Phe Val Tyr Gln Phe Lys Gly Met Cys Tyr Phe Thr
1               5                   10                  15

Asn Gly Thr Glu Arg Val Arg Leu Val Thr Arg Tyr Ile Tyr Asn Arg
            20                  25                  30

Glu Glu Tyr Ala Arg Phe Asp Ser Asp Val Gly Val Tyr Arg Ala Val
        35                  40                  45

Thr Pro Leu Gly Pro Pro Ala Ala Glu Tyr Trp Asn Ser Gln Lys Glu
    50                  55                  60

Val Leu Glu Arg Thr Arg Ala Glu Leu Asp Thr Val Cys Arg His Asn
65                  70                  75                  80

Tyr Gln Leu Glu Leu Arg Thr Thr Leu Gln Arg Arg Val Glu Pro Thr
```

```
                    85                  90                  95
Val Thr Ile Ser Pro Ser Arg Thr Glu Ala Leu Asn His His Asn Leu
                100                 105                 110

Leu Val Cys Ser Val Thr Asp Phe Tyr Pro Ala Gln Ile Lys Val Arg
                115                 120                 125

Trp Phe Arg Asn Asp Gln Glu Glu Thr Thr Ala Gly Val Val Ser Thr
        130                 135                 140

Pro Leu Ile Arg Asn Gly Asp Trp Thr Phe Gln Ile Leu Val Met Leu
145                 150                 155                 160

Glu Met Thr Pro Gln Arg Gly Asp Val Tyr Thr Cys His Val Glu His
                    165                 170                 175

Pro Ser Leu Gln Asn Pro Ile Ile Val Glu Trp Arg Ala Gln Ser
                180                 185                 190

<210> SEQ ID NO 202
<211> LENGTH: 178
<212> TYPE: PRT
<213> ORGANISM: Homo sapiens

<400> SEQUENCE: 202

Gln Phe Arg Val Ile Gly Pro Arg His Pro Ile Arg Ala Leu Val Gly
1               5                   10                  15

Asp Glu Val Glu Leu Pro Cys Arg Ile Ser Pro Gly Lys Asn Ala Thr
            20                  25                  30

Gly Met Glu Val Gly Trp Tyr Arg Pro Pro Phe Ser Arg Val Val His
        35                  40                  45

Leu Tyr Arg Asn Gly Lys Asp Gln Asp Gly Asp Gln Ala Pro Glu Tyr
    50                  55                  60

Arg Gly Arg Thr Glu Leu Leu Lys Asp Ala Ile Gly Glu Gly Lys Val
65                  70                  75                  80

Thr Leu Arg Ile Arg Asn Val Arg Phe Ser Asp Glu Gly Gly Phe Thr
                85                  90                  95

Cys Phe Phe Arg Asp His Ser Tyr Gln Glu Glu Ala Ala Met Glu Leu
                100                 105                 110

Lys Val Glu Asp Pro Phe Tyr Trp Val Ser Pro Gly Val Leu Val Leu
            115                 120                 125

Leu Ala Val Leu Pro Val Leu Leu Leu Gln Ile Thr Val Gly Leu Val
        130                 135                 140

Phe Leu Cys Leu Gln Tyr Arg Leu Arg Gly Lys Leu Arg Ala Glu Ile
145                 150                 155                 160

Glu Asn Leu His Arg Thr Phe Gly Gln Phe Leu Glu Glu Leu Arg Asn
                165                 170                 175

Pro Phe

<210> SEQ ID NO 203
<211> LENGTH: 81
<212> TYPE: PRT
<213> ORGANISM: Homo sapiens

<400> SEQUENCE: 203

Met Ser Gln Lys Pro Ala Lys Glu Gly Pro Arg Leu Ser Lys Asn Gln
1               5                   10                  15

Lys Tyr Ser Glu His Phe Ser Ile His Cys Cys Pro Pro Phe Thr Phe
            20                  25                  30

Leu Asn Ser Lys Lys Glu Ile Val Asp Arg Lys Tyr Ser Ile Cys Lys
        35                  40                  45
```

```
Ser Gly Cys Phe Tyr Gln Lys Lys Glu Glu Asp Trp Ile Cys Cys Ala
    50                  55                  60

Cys Gln Lys Thr Arg Leu Lys Arg Lys Ile Arg Pro Thr Pro Lys Lys
65                  70                  75                  80

Lys

<210> SEQ ID NO 204
<211> LENGTH: 999
<212> TYPE: PRT
<213> ORGANISM: Homo sapiens

<400> SEQUENCE: 204

Met Met Gly Leu Phe Pro Arg Thr Thr Gly Ala Leu Ala Ile Phe Val
1               5                   10                  15

Val Val Ile Leu Val His Gly Glu Leu Arg Ile Glu Thr Lys Gly Gln
                20                  25                  30

Tyr Asp Glu Glu Glu Met Thr Met Gln Gln Ala Lys Arg Arg Gln Lys
            35                  40                  45

Arg Glu Trp Val Lys Phe Ala Lys Pro Cys Arg Glu Gly Glu Asp Asn
    50                  55                  60

Ser Lys Arg Asn Pro Ile Ala Lys Ile Thr Ser Asp Tyr Gln Ala Thr
65                  70                  75                  80

Gln Lys Ile Thr Tyr Arg Ile Ser Gly Val Gly Ile Asp Gln Pro Pro
                85                  90                  95

Phe Gly Ile Phe Val Val Asp Lys Asn Thr Gly Asp Ile Asn Ile Thr
            100                 105                 110

Ala Ile Val Asp Arg Glu Glu Thr Pro Ser Phe Leu Ile Thr Cys Arg
        115                 120                 125

Ala Leu Asn Ala Gln Gly Leu Asp Val Glu Lys Pro Leu Ile Leu Thr
    130                 135                 140

Val Lys Ile Leu Asp Ile Asn Asp Asn Pro Pro Val Phe Ser Gln Gln
145                 150                 155                 160

Ile Phe Met Gly Glu Ile Glu Glu Asn Ser Ala Ser Asn Ser Leu Val
                165                 170                 175

Met Ile Leu Asn Ala Thr Asp Ala Asp Glu Pro Asn His Leu Asn Ser
            180                 185                 190

Lys Ile Ala Phe Lys Ile Val Ser Gln Glu Pro Ala Gly Thr Pro Met
        195                 200                 205

Phe Leu Leu Ser Arg Asn Thr Gly Glu Val Arg Thr Leu Thr Asn Ser
    210                 215                 220

Leu Asp Arg Glu Gln Ala Ser Ser Tyr Arg Leu Val Val Ser Gly Ala
225                 230                 235                 240

Asp Lys Asp Gly Glu Gly Leu Ser Thr Gln Cys Glu Cys Asn Ile Lys
                245                 250                 255

Val Lys Asp Val Asn Asp Asn Phe Pro Met Phe Arg Asp Ser Gln Tyr
            260                 265                 270

Ser Ala Arg Ile Glu Glu Asn Ile Leu Ser Ser Glu Leu Leu Arg Phe
        275                 280                 285

Gln Val Thr Asp Leu Asp Glu Glu Tyr Thr Asp Asn Trp Leu Ala Val
    290                 295                 300

Tyr Phe Phe Thr Ser Gly Asn Glu Gly Asn Trp Phe Glu Ile Gln Thr
305                 310                 315                 320

Asp Pro Arg Thr Asn Glu Gly Ile Leu Lys Val Val Lys Ala Leu Asp
                325                 330                 335

Tyr Glu Gln Leu Gln Ser Val Lys Leu Ser Ile Ala Val Lys Asn Lys
```

```
                    340                 345                 350
Ala Glu Phe His Gln Ser Val Ile Ser Arg Tyr Arg Val Gln Ser Thr
                355                 360                 365
Pro Val Thr Ile Gln Val Ile Asn Val Arg Glu Gly Ile Ala Phe Arg
370                 375                 380
Pro Ala Ser Lys Thr Phe Thr Val Gln Lys Gly Ile Ser Ser Lys Lys
385                 390                 395                 400
Leu Val Asp Tyr Ile Leu Gly Thr Tyr Gln Ala Ile Asp Glu Asp Thr
                405                 410                 415
Asn Lys Ala Ala Ser Asn Val Lys Tyr Val Met Gly Arg Asn Asp Gly
                420                 425                 430
Gly Tyr Leu Met Ile Asp Ser Lys Thr Ala Glu Ile Lys Phe Val Lys
                435                 440                 445
Asn Met Asn Arg Asp Ser Thr Phe Ile Val Asn Lys Thr Ile Thr Ala
                450                 455                 460
Glu Val Leu Ala Ile Asp Glu Tyr Thr Gly Lys Thr Ser Thr Gly Thr
465                 470                 475                 480
Val Tyr Val Arg Val Pro Asp Phe Asn Asp Asn Cys Pro Thr Ala Val
                485                 490                 495
Leu Glu Lys Asp Ala Val Cys Ser Ser Ser Pro Ser Val Val Val Ser
                500                 505                 510
Ala Arg Thr Leu Asn Asn Arg Tyr Thr Gly Pro Tyr Thr Phe Ala Leu
                515                 520                 525
Glu Asp Gln Pro Val Lys Leu Pro Ala Val Trp Ser Ile Thr Thr Leu
                530                 535                 540
Asn Ala Thr Ser Ala Leu Leu Arg Ala Gln Glu Gln Ile Pro Pro Gly
545                 550                 555                 560
Val Tyr His Ile Ser Leu Val Leu Thr Asp Ser Gln Asn Asn Arg Cys
                565                 570                 575
Glu Met Pro Arg Ser Leu Thr Leu Glu Val Cys Gln Cys Asp Asn Arg
                580                 585                 590
Gly Ile Cys Gly Thr Ser Tyr Pro Thr Thr Ser Pro Gly Thr Arg Tyr
                595                 600                 605
Gly Arg Pro His Ser Gly Arg Leu Gly Pro Ala Ala Ile Gly Leu Leu
                610                 615                 620
Leu Leu Gly Leu Leu Leu Leu Leu Ala Pro Leu Leu Leu Leu Thr
625                 630                 635                 640
Cys Asp Cys Gly Ala Gly Ser Thr Gly Gly Val Thr Gly Gly Phe Ile
                645                 650                 655
Pro Val Pro Asp Gly Ser Glu Gly Thr Ile His Gln Trp Gly Ile Glu
                660                 665                 670
Gly Ala His Pro Glu Asp Lys Glu Ile Thr Asn Ile Cys Val Pro Pro
                675                 680                 685
Val Thr Ala Asn Gly Ala Asp Phe Met Glu Ser Glu Val Cys Thr
                690                 695                 700
Asn Thr Tyr Ala Arg Gly Thr Ala Val Glu Gly Thr Ser Gly Met Glu
705                 710                 715                 720
Met Thr Thr Lys Leu Gly Ala Ala Thr Glu Ser Gly Ala Ala Gly
                725                 730                 735
Phe Ala Thr Gly Thr Val Ser Gly Ala Ala Ser Gly Phe Gly Ala Ala
                740                 745                 750
Thr Gly Val Gly Ile Cys Ser Ser Gly Gln Ser Gly Thr Met Arg Thr
                755                 760                 765
```

```
Arg His Ser Thr Gly Gly Thr Asn Lys Asp Tyr Ala Asp Gly Ala Ile
    770                 775                 780

Ser Met Asn Phe Leu Asp Ser Tyr Phe Ser Gln Lys Ala Phe Ala Cys
785                 790                 795                 800

Ala Glu Glu Asp Asp Gly Gln Glu Ala Asn Asp Cys Leu Leu Ile Tyr
                805                 810                 815

Asp Asn Glu Gly Ala Asp Ala Thr Gly Ser Pro Val Gly Ser Val Gly
            820                 825                 830

Cys Cys Ser Phe Ile Ala Asp Asp Leu Asp Asp Ser Phe Leu Asp Ser
            835                 840                 845

Leu Gly Pro Lys Phe Lys Lys Leu Ala Glu Ile Ser Leu Gly Val Asp
        850                 855                 860

Gly Glu Gly Lys Glu Val Gln Pro Pro Ser Lys Asp Ser Gly Tyr Gly
865                 870                 875                 880

Ile Glu Ser Cys Gly His Pro Ile Glu Val Gln Gln Thr Gly Phe Val
                885                 890                 895

Lys Cys Gln Thr Leu Ser Gly Ser Gln Gly Ala Ser Ala Leu Ser Thr
                900                 905                 910

Ser Gly Ser Val Gln Pro Ala Val Ser Ile Pro Asp Pro Leu Gln His
            915                 920                 925

Gly Asn Tyr Leu Val Thr Glu Thr Tyr Ser Ala Ser Gly Ser Leu Val
        930                 935                 940

Gln Pro Ser Thr Ala Gly Phe Asp Pro Leu Leu Thr Gln Asn Val Ile
945                 950                 955                 960

Val Thr Glu Arg Val Ile Cys Pro Ile Ser Ser Val Pro Gly Asn Leu
                965                 970                 975

Ala Gly Pro Thr Gln Leu Arg Gly Ser His Thr Met Leu Cys Thr Glu
            980                 985                 990

Asp Pro Cys Ser Arg Leu Ile
            995

<210> SEQ ID NO 205
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Glu Lys Ala Lys Tyr Glu Ala Tyr Lys Ala Ala Ala Ala Ala Ala
1               5                   10                  15

<210> SEQ ID NO 206
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Lys Asp Ile Leu Glu Asp Glu Arg Ala Ala Val Asp Thr Tyr Cys
1               5                   10                  15

<210> SEQ ID NO 207
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
                                   -continued peptide

<400> SEQUENCE: 207

Asp Glu Arg Ala Ala
1               5

<210> SEQ ID NO 208
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Gln Lys Arg Ala Ala
1               5

<210> SEQ ID NO 209
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gln Lys Arg Ala Ala Tyr Asp Gln Tyr Gly His Ala Ala Phe Glu
1               5                   10                  15

<210> SEQ ID NO 210
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Gly Asp Leu Gln Val Leu
1               5

<210> SEQ ID NO 211
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Tyr Pro Tyr Asp Val Pro Asp Tyr Ala Ser Leu Arg Ser
1               5                   10

<210> SEQ ID NO 212
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Asp Val Pro Asp Tyr Ala
1               5

<210> SEQ ID NO 213
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Glu Asn Pro Val Val His Glu Phe Lys Asn Ile Val Thr Pro Arg Thr
1               5                   10                  15
Pro

<210> SEQ ID NO 214
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Ala Lys Pro Val Val His Leu Phe Ala Asn Ile Val Thr Pro Arg Thr
1               5                   10                  15
Pro

<210> SEQ ID NO 215
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Tyr Phe Ala Lys
1

<210> SEQ ID NO 216
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Glu Tyr Tyr Lys
1

<210> SEQ ID NO 217
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Tyr Glu Ala Lys
1

<210> SEQ ID NO 218
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 218

Ala Glu Lys Tyr
1

<210> SEQ ID NO 219
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Phe Leu Met Tyr
1

<210> SEQ ID NO 220
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Ile Met Gln Val
1

<210> SEQ ID NO 221
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Lys Arg Ile Leu Val
1               5

<210> SEQ ID NO 222
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Phe Ile Leu Met Val
1               5

<210> SEQ ID NO 223
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Phe Trp Glu Phe
1

<210> SEQ ID NO 224
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 224

Ala Ile Asn Val
1

<210> SEQ ID NO 225
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Tyr Glu Phe Trp
1

<210> SEQ ID NO 226
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Glu Phe Ile Val Trp Tyr
1               5

<210> SEQ ID NO 227
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Glu Phe Lys Gln
1

<210> SEQ ID NO 228
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Ala Glu Lys Gln
1

<210> SEQ ID NO 229
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Ala Lys Gln Tyr
1
```

-continued

<210> SEQ ID NO 230
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Ala Asn Gln Tyr
1

<210> SEQ ID NO 231
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Ala Gly Asn Ser Tyr
1               5

<210> SEQ ID NO 232
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Ala Gly Ile Asn Ser Val
1               5

<210> SEQ ID NO 233
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ala Ile Gln Ser Val
1               5

<210> SEQ ID NO 234
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Ile Lys Arg Ser Val Tyr
1               5

<210> SEQ ID NO 235
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Lys His Arg Val
1

<210> SEQ ID NO 236
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Ala Lys Ala Val Ala Ala Trp Thr Leu Lys Ala Ala Ala
1               5                   10

<210> SEQ ID NO 237
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Thr His Met Cys Glu
1               5

<210> SEQ ID NO 238
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Pro Trp Lys Asn Ala
1               5

<210> SEQ ID NO 239
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Arg Gly Asp Ser
1

<210> SEQ ID NO 240
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Tyr Val Arg Pro Leu Trp Val Arg Met Glu
1               5                   10